US006403638B1

(12) United States Patent
Vuligonda et al.

(10) Patent No.: US 6,403,638 B1
(45) Date of Patent: *Jun. 11, 2002

(54) 2,4-PENTADIENOIC ACID DERIVATIVES HAVING SELECTIVE ACTIVITY FOR RETINOID X (RXR) RECEPTORS

(75) Inventors: Vidyasagar Vuligonda; Kwok Yin Tsang; Jayasree Vasudevan, all of Irvine; Roshantha A. Chandraratna, Mission Viejo, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/532,677

(22) Filed: Mar. 21, 2000

Related U.S. Application Data

(63) Continuation-in-part of application No. 09/164,950, filed on Oct. 1, 1998, now Pat. No. 6,147,224.

(51) Int. Cl.[7] .................... A61K 31/21; A61K 31/19; C07D 319/14; C07D 303/38; C07C 65/34

(52) U.S. Cl. .................. 514/457; 514/531; 514/557; 514/569; 514/570; 514/510; 549/102; 549/124; 549/362; 549/407; 549/408; 549/548; 549/549; 549/551; 560/20; 560/21; 560/23; 560/102; 560/124; 562/433; 562/434; 562/462; 562/466; 562/469; 562/492

(58) Field of Search .................. 514/509, 557, 514/531, 570, 510, 457; 549/362, 551, 407, 408, 409, 548, 549; 560/20, 21, 23, 124, 102; 562/433, 434, 462, 466, 469, 492

(56) References Cited

U.S. PATENT DOCUMENTS

| | | | |
|---|---|---|---|
| 5,455,265 A | 10/1995 | Chandraratna | 514/448 |
| 5,543,534 A | 8/1996 | Vuligonda et al. | 549/421 |
| 5,648,514 A | 7/1997 | Johnson et al. | 560/102 |
| 5,663,367 A | 9/1997 | Vuligonda et al. | 549/4 |
| 5,675,033 A | 10/1997 | Vuligonda et al. | 560/100 |
| 5,723,666 A | 3/1998 | Vuligonda et al. | 564/253 |
| 5,728,846 A | 3/1998 | Vuligonda et al. | 549/16 |

FOREIGN PATENT DOCUMENTS

| | | | |
|---|---|---|---|
| EP | 0369762 | 5/1990 | C07C/233/11 |
| EP | 0718285 | 6/1996 | C07C/403/20 |
| WO | 93/11755 | 6/1993 | A61K/31/07 |
| WO | 93/21146 | 10/1993 | C07C/69/76 |
| WO | 95/04036 | 2/1995 | C07C/403/20 |
| WO | 96/05165 | 2/1996 | C07C/57/50 |
| WO | 96/39374 | 12/1996 | C07C/69/618 |
| WO | 97/09297 | 3/1997 | C07C/69/78 |
| WO | 97/12853 | 4/1997 | C07C/59/72 |

OTHER PUBLICATIONS

Verma & Boutwell, Cancer Research, (1977), 37 2196–2201.
Feigner P. L. and Holm M. (1989) Focus, 112.
Heyman et al., Cell 68, 397–406, (1992).
Allegretto et al., J. Biol. Chem. 268, 26625–26633.
Mangelsdorf et al., The Retinoids: Biology, Chemistry and Medicine, pp. 319–349, Raven Press Ltd., New York.
Cheng et al., Biochemical Pharmacology vol. 22 pp. 3099–3108.
Klein et al., J. Biol. Chem. 271, 22692–22696 (1996).
Chen et al. (1987) Mol. Cell. Biol. 7, 2745–2752.
de Wet (1987) Mol. Cell. Biol. 7, 725–737.
Nagpal et al., Embo J. 12, 2349–2360 (1993).
Corey, E. J., Schmidt, G., *Tet. Lett.*, 399, (1979).
Omura, K., Swern, D., *Tetrahedron*, 1978, 34, 1651.
Journal of Organic Chemistry (1995) 60, 1081–1083.
Journal of Organic Chemistry (1974) vol. 39, p. 821.
Johnson et al., J. Med. Chem. (1995), 38, 4764–4767.
Mathur et al., Tetrahedron, 41, 1509–1516 (1985).

(List continued on next page.)

*Primary Examiner*—Alan L. Rotman
*Assistant Examiner*—Raymond Covington
(74) *Attorney, Agent, or Firm*—Gabor L. Szekeres; Robert J. Baran; Martin A. Voet

(57) ABSTRACT

Compounds having the formulas below, where R is H, lower alkyl, or a pharmaceutically acceptable salt, and where $R_1$ represents i-propyl, t-butyl or n-butyl groups, have selective RXR retionoid agonist activity.

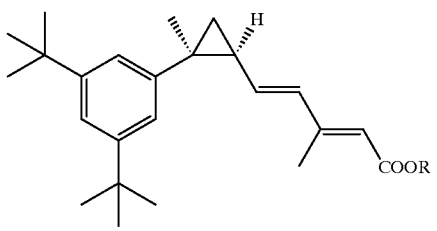

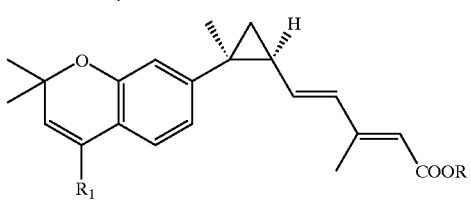

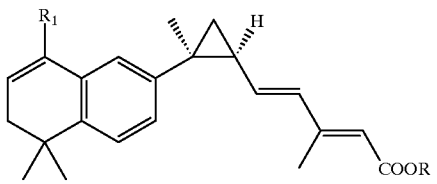

20 Claims, No Drawings

OTHER PUBLICATIONS

Kagechika et al., J. Med. Chem. (1988), 31, 2182.
J. Org. Chem. 14 (1949), 509, 512.
Helv. Chim. Acta 39 (1956), 505–511.
J. Ind. Chem. Soc. (1940), 17, 65–67.
Bull. Chem. Soc. Jap. (1980), 53, 2046–2049.
Le Noble, W. J. et al., J. Org. Chem. 36 (1971) 193–196.
J. Med. Chem., (1990), 33, 3028–3034.
Eberbach W et al: "6–und 8–Pi–Ringschlussreaktionen von 2–Oxaheptatrienyl–Dipolen: Synthese von 3–Vinyl–2, 3–dihydrofuranen und 2, 3(6,7)–Dihydrooxepinen" Chemische Berichte, vol. 114, No. 8, Aug. 3, 1981, pp. 2979–3003, XP002126876 the whole document, particularly p. 2981, compounds 11c, 11h, 12c and 12h.
Dussault P H et al: "Auxiliary–directed peroxidation of 1,4–dienes" Tetrahedron, vol. 52, No. 38, Sep. 16, 1996, pp. 12381–12398, XP002126877 the whole document, particularly p. 12383, compounds 3 and 6.

Database Crossfire Online! Beilstein Institut fuer Literatur der organischen Chemie XP002126879 Beilstein Registry No. 6382860 & Aust. J. Chem., vol. 40, No. 9, 1987 pp. 1499–1509.

Schneider M et al: "Facile synthesis of cyclopropylalkadienes" Angewandte Chemie, International Edition, vol. 18, No. 3, Mar. 1979, pp. 231–233, XP002126878 the whole document, particularly compound 4e.

Wilson R M et al: "Orbital symmetry governed reactions under high–intensity argon laser–jet conditions: the involvement of 1,5s! sigmatropic shift in the photocyclization of an o–alkenylbenzaldehyde to a benzocyclobutenone" Journal of the American Chemical Society, vol. 117, No. 29, p. 7820–7821 XP000517236 ISSN: 0002–7863 the whole document, particularly p. 7820, compound 5.

2,4-PENTADIENOIC ACID DERIVATIVES HAVING SELECTIVE ACTIVITY FOR RETINOID X (RXR) RECEPTORS

CROSS-REFERENCE TO RELATED APPLICATION

The present application is a continuation-in-part of application Ser. No. 09/164,950, filed on Oct. 1, 1998 now U.S. Pat. No. 6,147,229.

BACKGROUND OF THE INVENTION

1. Field of the Invention

The present invention relates to novel compounds having retinoid-like biological activity. More specifically, the present invention relates to 2,4-pentadienoic acid derivatives having selective activity for retinoid X (RXR) receptors.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptorsexist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists.

Published PCT application WO 97/09297, assigned to the same assignee as the present application, describes several compounds having retinoid antagonist and retinoid inverse agonist type biological activity, and discloses that the above mentioned retinoid antagonist and/or inverse agonist-like activity of a compound is also a useful property, in that such antagonist or inverse agonist-like compounds can be utilized to block certain undesired side effects of retinoids, to serve as antidotes to retinoid overdose or poisoning, and may lend themselves to other pharmaceutical applications as well.

Numerous compounds having selective agonist-like activity for RXR retinoid receptors are described in published PCT applications WO 93/21146, WO 95/04036 and WO 97/12853. In these PCT publications specific compounds of particular interest as background to the present invention are, in the WO 93/21146 reference: 4-[1-(3,5,5,8,8-pentamethyl-5,6,7,8-tetrahydro-2-naphthyl)epoxy]benzoic acid, 4-[1-(3,5,5,8,8-pentamethyl-5,6,7,8-tetrahydro-2-naphthyl)cyclopropyl]benzoic acid, 2-[1-(3,5,5,8,8-pentamethyl-5,6,7,8-tetrahydro-2-naphthyl)cyclopropyl] pyridine-5-carboxylic acid and methyl 2-[1-(3,5,5,8,8-pentamethyl-5,6,7,8-tetrahydro-2-naphthyl)cyclopropyl] pyridine-5-carboxylate (Compounds 47, 48, 62 and Me-62 on pages 15 and 17 of WO 93/21146);

in the WO 95/04036 reference: (2E,4E)-3-methyl-5-[1-(3,5,8,8-pentamethyl-5,6,7,8-tetrahydro-2-naphthyl) cyclopropyl]penta-2,4-dienoic acid (Compound 104 on page 23 of WO 95/04036).

In the WO 97/12853 reference: tetramethyl-3-propyloxy-5,6,7,8-tetrahydronaphthalen-2-yl)cyclopropan-1-yl]-3-methyl hexadienoic acid (Compound 152); (2E,4E)-6-[2-(5,5,8,8-tetramethyl-3-heptyloxy-5,6,7,8-tetrahydronaphthalen-2-yl)cyclopropan-1-yl]-3-methyl hexadienoic acid (Compound 153); (2E,4E)-6-[2-(5,5,8,8-tetramethyl-3-benzyloxy-5,6,7,8-tetrahydronaphthalen-2-yl)cyclopropan-1-yl]-3-methyl hexadienoic acid (Compound 154); (2E,4E)-7-[(5,5,8,8-tetramethyl-3-propyloxy-5,6,7,8-tetrahydronaphthalen-2-yl)cyclopropan-1-yl]-3-methyl heptadienoic acid (Compound 155); (2E,4E)-7-[(5,5,8,8-tetramethyl-3-heptyloxy-5,6,7,8-tetrahydronaphthalen-2-yl)cyclopropan-1-yl]-3-methyl heptadienoic acid (Compound 156); (2E,4E)-7-[(5,5,8,8-tetramethyl-3-benzyloxy-5,6,7,8-tetrahydronaphtha-1en-2-yl)cyclopropan-1-yl]-3-methyl heptadienoic acid (Compound 157); (2E,4E)-5-[2-(5,5,8,8-tetramethyl-3-propyloxy-5,6,7,8-tetrahydronaphthalen-2-yl)cyclopent-1-en-1-yl]-3-methyl pentadienoic acid (Compound 158); cis (2E,4E)-5-[2-(5,5,8,8-tetramethyl-3-propyloxy-5,6,7,8-tetrahydro-2-naphthyl)cyclopentan-1-yl]-3-methyl pentadienoic acid (Compound 159).

The following prior art compounds are also of interest to the present invention:

(2E,4E)-6-[1-(5,5,8,8-tetramethyl-5,6,7,8-tetrahydronaphthalen-2-yl)cyclopropan-1-yl]-3-methyl hexadienoic acid (Compound 101); (2E,4E)-6-[(3,5,5,8,8-pentamethyl-5,6,7,8-tetrahydronaphthalen-2-yl) cyclopropan- 1-yl]-3-methyl hexadienoic acid (Compound 102); (2E,4E)-6-[(5,5,8,8-tetramethyl-3-methoxy-5,6,7,8-tetrahydronaphthalen-2-yl) cyclopropan-1-yl]-3-methyl hexadienoic acid (Compound 103); (2E,4E)-6-[(5,5,8,8-tetramethyl-3-ethoxy-5,6,7,8-tetrahydronaphthalen-2-yl) cyclopropan-1-yl]-3-methyl hexadienoic acid (Compound 104); (2E,4E)-6-[(3,5-di-t-butyl phenyl) cyclopropan-1-yl]-3-methyl hexadienoic acid (Compound 105); (2E,4E)-6-[(3,4-diethyl phenyl) cyclopropan-1-yl]-3-methyl hexadienoic acid (Compound 106); (2E,4E)-6-[1-(6-t-butyl-1,1-dimethyl-indan-4-yl)-cyclopropyl]-3-methyl hexadienoic acid (Compound 107); and (2E,4E)-6-[(5,5,8,8-tetramethyl-5,6,7,8-tetrahydronaphthalen-2-yl) cyclopentane-1-yl]-3-methyl hexadienoic acid (Compound 108).

The publication WO 96/39374 published on Dec. 12, 1996 (corresponding to U.S. Pat. Nos. 5,663,367 and 5,675,033) describes 2,4-pentadienoic acid derivatives having selective activity for retinoid RXR receptors. The compounds of this reference include a condensed cyclic (tetrahydronaphthyl, chromanyl or thiochromanyl) moiety, and a cycloalkyl (primarily cyclopropyl) or phenyl or heteroaryl moiety linking the pentadienoic acid moiety to the condensed cyclic moiety.

U.S. Pat. No. 5,648,514 discloses phenylethynyl or heteroarylethynyl dihydronaphthalene derivatives where the 5 or 8 position (depending on the system of numbering) of the dihydronaphthalene nucleus is substituted with an alicyclic, aryl or heteroaryl group. U.S. Pat. No. 5,723,666 (formula 6 in Column 9) discloses further dihydronaphthalene derivatives where the 5 or 8 position (depending on the system of numbering) of the dihydronaphthalene nucleus is substituted with an alicyclic, aryl or heteroaryl group. The compounds of this reference have retinoid-like or retinoid antagonist-like biological activity.

SUMMARY OF THE INVENTION

The present invention relates to compounds of Formula 1, Formula 2 or Formula 3

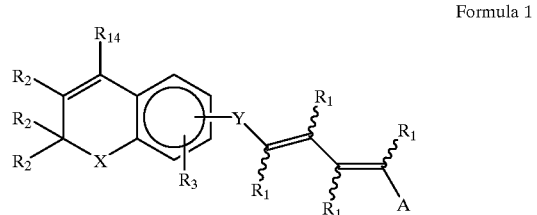

Formula 1

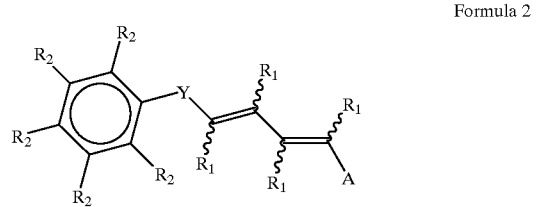

Formula 2

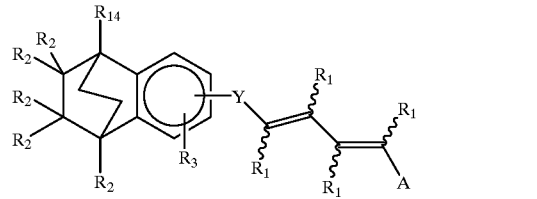

Formula 3 where X is O, S, or $(CR_1R_1)_n$ where n is 0, 1 or 2;

Y is a bivalent radical having Formula 4 or Formula 5 where O is an integer from 1 to 4

Formula 4

Formula 5 or Y is a bivalent aryl or 5 or 6 membered heteroaryl radical having 1 to 3 heteroatoms selected from N, S and O, said aryl or heteroaryl groups being unsubstituted, or substituted with 1 to 3 $C_{1-6}$alkyl or with 1 to 3 $C_{1-6}$fluoroalkyl groups;

$X_1$ is O, S or NH;

$R_1$ is independently H, lower alkyl of 1 to 6 carbons, or lower fluoroalkyl of 1 to 6 carbons;

$R_2$ is independently H, lower alkyl of 1 to 6 carbons, $OR_1$, 1-adamantyl, or lower fluoroalkyl of 1 to 6 carbons, or the two $R_2$ groups jointly represent an oxo (=O) group;

$R_3$ is hydrogen, lower alkyl of 1 to 6 carbons, $OR_1$, fluoro substituted lower alkyl of 1 to 6 carbons or halogen, $NO_2$, $NH_2$, $NHCO(C_1-C_6)$alkyl, or $NHCO(C_1-C_6)$alkenyl;

A is hydrogen, COOH or a pharmaceutically acceptable salt thereof, $COOR_8$, $CONR_{9R10}$, $-CH_2OH$, $CH_2OR_{11}$, $CH_2OCOR_{11}$, CHO, $CH(OR_{12})_2$, $CH(OR_{13}O)$, $-COR_7$, $CR_7(OR_{12})_2$, $CR_7(OR_{13}O)$, or $Si(C_{1-6}alkyl)_3$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, and $R_{14}$ is alkyl of 1 to 10 carbons, fluoro-substituted alkyl of 1 to 10 carbons, alkenyl of 2 to 10 carbons and having 1 to 3 double bonds, alkynyl having 2 to 10 carbons and 1 to 3 triple bonds, carbocyclic aryl selected from the group consisting of phenyl, $C_1-C_{10}$-alkylphenyl, naphthyl, $C_1-C_{10}$-alkylnaphthyl, phenyl-$C_1-C_{10}$alkyl, naphthyl-$C_1-C_{10}$alkyl, $C_1-C_{10}$-alkenylphenyl having 1 to 3 double bonds, $C_1-C_{10}$-alkynylphenyl having 1 to 3 triple bonds, phenyl-$C_1-C_{10}$alkenyl having 1 to 3 double bonds, phenyl-$C_1-C_{10}$alkynyl having 1 to 3 triple bonds, hydroxy alkyl of 1 to 10 carbons, hydroxyalkenyl having 2 to 10 carbons and 1 to 3 double bonds, hydroxyalkynyl having 2 to 10 carbons and 1 to 3 triple bonds, acyloxyalkyl of 1 to 10 carbons, acyloxyalkenyl having 2 to 10 carbons and 1 to 3 double bonds, or acyloxyalkynyl of 2 to 10 carbons and 1 to 3 triple bonds where the acyl group is represented by $COR_8$, or $R_{14}$ is a 5 or 6 membered heteroaryl group having 1 to 3 heteroatoms, said heteroatoms being selected from a group consisting of O, S, and N, said heteroaryl group being unsubstituted or substituted with a $C_1$ to $C_{10}$alkyl group, with a $C_1$ to $C_{10}$fluoroalkyl group, or with halogen, and the dashed line in Formula 4 represents a bond or absence of a bond.

In a second aspect, this invention relates to the use of the compounds of Formula 1, Formula 2, and Formula 3 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other comeopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be coadministered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formulas 1, 2 or 3 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and decrease in cell proliferation was done by Verma & Boutwell, Cancer Research, 1977, 37, 2196–2201. That reference discloses that omithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670, 1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$ and $RXR_\gamma$ receptors, and the ability or inability of the compounds to activate transcription of a reporter gene through these receptor subtypes can be tested. These assays are expected to demonstrate that the compounds of the present invention are primarily selective agonists of RXR receptors in preferance over RAR receptors. However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly usefull therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et as. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

RAR-P-GR holoreceptor Transactivation Assay

CV-1 cells ($4 \times 10^5$ cells/well) were transiently transfected with the luciferase reporter plasmid MTV-4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol, Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the PAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except 115 of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. J. Biol. Chem. 271, 22692–22696 (1996) which is expressly incorporated herein by reference.

In this assay, retinoid inverse agonists are able to repress the basal activity of a RARγ-VP-16 chimeric receptor where the constituitively active domain of the herpes simplex virus (HSV) VP-16 is fused to the N-terminus of RARγ. CV-1 cells are cotransfected with RARγ-VP-16, an ER-RXRα chimeric receptor and an ERE-tk-Luc chimeric reporter gene to produce a basal level of luciferase activity, as shown by Nagpal et al. EMBO J. 12, 2349–2360 (1993) expressly incorporated herein by reference. Retinoid inverse agonists are able to inhibit the basal luciferase activity in these cells in a dose dependent manner and $IC_{50}$s measured.

Table 1 discloses data demonstrating the ability of exemplary compounds of the invention to bind to and transactivate through RXR receptors.

TABLE 1

RXR RECEPTOR TRANSACTIVATION AND BINDING DATA:

| Compound # | | RXR α | RXR β | RXR γ |
|---|---|---|---|---|
| 7 | $EC_{50}$nM | 0.0003 | 0.06 | 0.0006 |
|   | % Eff | 147 | 152 | 156 |
|   | $K_d$nM | 0.05 | $ND^1$ | 7.3 |
| 14 | $EC_{50}$nM | 09 | 4.3 | 1.3 |
|   | % Eff | 93 | 80 | 86 |
|   | $K_d$nM | 0.03 | $ND^1$ | 3.7 |
| 22 | $EC_{50}$nM | 0.3 | 1.8 | 0.8 |
|   | % Eff | 94 | 88 | 110 |
|   | $K_d$nM | 0.027 | $ND^1$ | 0.58 |
| 28 | $EC_{50}$nM | 0.05 | 0.46 | 0.14 |
|   | % Eff | 103 | 111 | 96 |
|   | $K_d$nM | 0.21 | $ND^1$ | 3.1 |
| 34 | $EC_{50}$nM | 0.05 | 0.9 | 0.1 |
|   | % Eff | 105 | 98 | 115 |
|   | $K_d$nM | 0.01 | $ND^1$ | 1.4 |
| 87 | $EC_{50}$(nM) | 0.1 | 0.3 | 0.1 |
|   | % Eff. | 102 | 107 | 116 |
|   | Kd (nM) | 0.05 | 2.9 | 0.32 |
| 88 | $EC_{50}$(nM) | 0.1 | 0.1 | 0.1 |
|   | % Eff. | 106 | 107 | 105 |
|   | KD (nM) | 0.17 | 1.6 | 1.4 |
| 89 | $EC_{50}$(nM) | 0.1 | 0.1 | 0.1 |
|   | % Eff. | 110 | 99 | 112 |
|   | Kd (nM) | 0.19 | 0.60 | 1.4 |
| 96 | $EC_{50}$(nM) | 1 | 9 | 2 |
|   | % Eff | 87 | 85 | 112 |
|   | Kd (nM) | 0.6 | 1.7 | 2.8 |
| 57 | $EC_{50}$(nM) | 0.1 | 0.7 | 0.1 |
|   | % Eff | 95 | 95 | 89 |
|   | Kd (nM) | 0.01 | 0.8 | 4.2 |
| 64 | $EC_{50}$(nM) | 0.1 | 0.3 | 0.1 |
|   | %Eff | 109 | 109 | 108 |
|   | Kd(nM) | 0.7 | 6 | 3 |

[1]ND - not determined

Modes of Administration

The compounds of this invention may be administered systemically or topically, depending on such considerations as the condition to be treated, need for site-specific treatment, quantity of drug to be administered, and numerous other considerations. Inasmuch as the preferred compounds of the invention are primarily RXR selective agonists, the preferred compounds are administered as retinoids.

Thus, in the treatment of dematoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dematoses; medicaments for preventing infection, reducing irritation, inflammation and the like.

Treatment of dematoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patients susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dematoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be usefull to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patients susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where A of Formula 1, 2 or 3 is —COOH, this term covers the products derived from treatment of this function with alcohols or thiols preferably with aliphatic alcohols having 1–6 carbons. Where the ester is derived from compounds where A is —$CH_2OH$, this term covers compounds derived from organic acids capable of forming esters including phosphorous based and sulfur based acids, or compounds of the formula —$CH_2OCOR_{11}$ where $R_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred. Acetals and ketals include the radicals of the formula-CK where K is (—OR)$_2$. Here, R is lower alkyl. Also, K may be —OR$_7$O— where $R_7$ is lower alkyl of 2–5 carbon atoms, straight chain or branched.

A pharmaceutically acceptable salt may be prepared for any compounds in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

Many compounds of the present invention have trans and cis (E and Z) isomers. Specific orientation of substituents relative to a double bond is indicated in the name of the respective compound, and/or by specifically showing in the structural formula the orientation of the substituents relative to the double bond.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

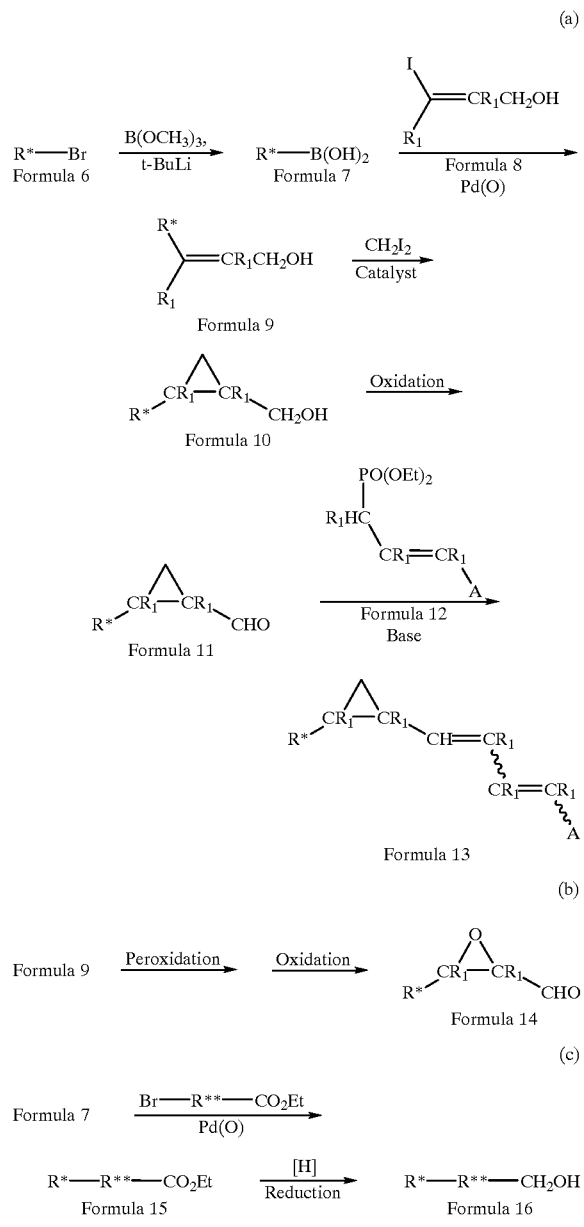

Reaction Scheme 1

A generalized methodology for obtaining the compounds of the invention is illustrated in Reaction Scheme 1. As is shown in section (a) of this scheme, compounds of the invention where Z is a cyclopropyl function within the definitions of Formulas 1, 2 and 3 are generally obtained in a sequence of reactions which initially involves a multi-step synthesis of a halogen substituted compound (Formula 6) where the halogen atom, preferably bromine, is positioned on the aromatic nucleus of dihydronaphthalene, indene, chrom-3-en, thiochrom-3-en (Formula 1), 2,3-benzobicyclooctane moiety (Formula 3) or on the phenyl group (compounds of Formula 2). In compounds of Formula 1 the 8 position of the dihydronaphtalene nucleus or the 4position of the chrom-3-en or thiochrom-3-en nucleus bear a substituent designated $R_{14}$. Generally speaking the $R_{14}$ group and the 7,8 or 3,4 double bond, as applicable, are obtained in these compounds by reacting the corresponding tetrahydronaphthalene-8-one or the corresponding chroman-4-one or thiochroman-4-one with a Grignard ($R_{14}$—Mg—Br) or like organometallic reagent, followed by dehydration of the intermediary tertiary alcohol. Introduction of the $R_{14}$ group and formation of the double bond are not shown in Reaction Scheme 1.

In accordance with the general synthetic methodology the above-noted halogen, preferably bromine, substituted compound of Formula 6 is reacted with trimethoxy boron ($(CH_3O)_3B$) in the presence of tertiary butyl lithium. The resulting dihydronaphtalen-2-yl, chromen-6-yl, thiochromen-6-yl, [2,3]benzo-4-ylbicyclooctan, or phenyl boronic acid (as applicable, Formula 7) is therafter reacted in the presence of palladium catalyst (Pd(0)) with a 3-iodo-allyl alcohol derivative (Formula 8) to yield a prop-2-en-1-ol derivative (Formula 9) that is substituted in the 3 position of the propene moiety with the dihydronaphtalen-2-yl, chrom-3-en-6-yl, thiochrom-3-en-6-yl, [2,3]benzo-4-ylbicyclooctan, or phenyl derivative, as applicable. The cyclopropane ring is introduced into the prop-2-en-1-ol derivative of Formula 9 in a cyclopropylation reaction with diiodomethane in the presence of appropriate catalyst to yield a cyclopropyl derivative of Formula 10. Thereafter, the primary alcohol function of the compound of Formula 10 is oxidized to the aldehyde stage (Formula 11), and the aldehyde compound of Formula 11 is reacted in a Horner Emmons reaction with a diethylphosphono reagent (Formula 12) that has a double bond on a carbon adjacent to the carbon bearing the diethylphosphono group. Consequently, as a result of the Horner Emmons reaction, the conjugated diene moiety of the compounds of the invention (Formula 13) is formed. In as much as the diethylphosphono reagent (Formula 12) also bears the A function (as defined above) of the compounds of the invention, or such precursors of the A function that can be readily converted to the A group by reactions well known in the art, the above-described Horner-Emmons reaction provides compounds of the invention where the Y group of Formulas 1, 2 and 3 represent cyclopropyl.

Section (b) of Reaction Scheme 1 shows that compounds of the invention where Y represents an oxiranyl (epoxide) ring instead of cyclopropyl, can be made by methods similar to the above described methodology except that instead of cyclopropylating, the compounds of Formula 9 are epoxidized using reagents well known in the art, for example with meta-chloroperoxybenzoic acid. The resulting oxiranyl (epoxide) compound that has a primary alcohol is oxidized to the aldehyde stage (Formula 14) with state-of-the-art reagents, and the aldehyde is subjected to a Horner Emmons reaction, as shown above, to yield the oxiranyl (epoxide) compounds of the invention. The Horner Emmons reaction that is performed on the oxiranyl compounds of Formula 14 is not shown in the reaction scheme.

Compounds of the invention where the Y group is aryl, heteroaryl or cycloalkyl other then cyclopropyl can, generally speaking, be obtained from the boronic acid derivatives as shown in section (c) of Reaction Scheme 1. In this scheme R** represents a bivalent aryl, heteroaryl or cycloalkyl, other than cyclopropyl, radical as these are defined in connection with Formulas 1, 2 and 3. In accordance with this generalized scheme, the boronic acid derivative of Formula 7 is coupled in the presence of palladium (Pd(0)) catalyst with a halogenated, preferably brominated, cycloalkyl, aryl or heteroaryl carboxylic acid ester. The carboxylic acid ester function of the resulting compound (Formula 15) is reduced to the primary alcohol stage (Formula 16). The primary alcohol of Formula 16 is thereafter treated in the same reaction sequence (oxidation followed by Horner Emmons reaction) as described above, to provide compounds of the invention.

Details of the above-outlined generalized synthetic schemes are provided below in connection with the description of the specific embodiments.

The synthetic methodology employed for the synthesis of the compounds of the present invention may also include transformations of the group designated A in Formulas 1, 2 and 3. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., Tet. Lett., 399, 1979), or dimethyl sulfoxide/oxalyl chloride in methylene chloride (Omura, K., Swern, D., Tetrahedron, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

SPECIFIC EMBODIMENTS

With reference to the symbol X in the Formula 1, preferred compounds of the invention are those where X is O (chromen derivatives), S (thiochromen derivatives) and where X is $(CR_1R_1)_n$ and n is 1 (dihydronaphthalene derivatives). 5,5-Dimethyldihydronaphthalene derivatives where $R_1$ of $CR_1R_1$ is $CH_3$ are particularly preferred. The $R_2$ groups of the compounds of Formula 1 and of Formula 3 preferably and independently from one another are H or lower alkyl, and even more preferably and independently from one another H and methyl. When X is S or O, then the $R_2$ groups in the 2 position of the chromen or thichromen nucleus are preferably $CH_3$. The $R_3$ groups of the preferred compounds of the invention are H or lower alkyl; among lower alkyl methyl is preferred.

The $R_2$ groups of the preferred compounds of Formula 2 are H or lower alkyl. Those $R_2$ groups which are in meta position relative to the Y group in the compounds of Formula 2 preferably are lower branch-chained alkyl. The $R_1$ groups of the cycloalkyl and of the oxiranyl rings, as shown in Formulas 4 and 5 are preferably H or lower alkyl, even more preferably H, methyl, ethyl or n-propyl. The $R_1$ groups attached to the diene moiety are also preferably H or lower alkyl, even more preferably H or methyl.

The Y group is preferably cyclopropyl, as represented by Formula 4 where o is 1 and the dashed line represents absence of a bond, or Y is oxiranyl as represented by Formula 5. Alternatively the Y group is preferably cyclohexyl, cyclopentyl, phenyl, pyridyl, thienyl, faryl or thiazolyl.

When the Y group is cycloalkyl, as represented by Formula 4, then the diene moiety and the aromatic residue of the condensed cyclic group or the phenyl group, as applicable, are preferably in cis orientation relative to the cycloalkyl ring. When the Y group is aryl or heteroaryl then the diene moiety and the aromatic residue of the condensed cyclic group or the phenyl group, as applicable, are preferably in ortho or 1,2 orientation relative to the aryl or heteroaryl ring, as applicable.

The A group is preferably COOH, a pharmaceutically acceptable salt of the carboxylic acid, $COOR_8$ or $CONR_9R_{10}$ where $R_8$ are preferably lower alkyl, even more preferably methyl or ethyl.

The double bonds of the diene moiety preferably are in trans orientation.

Attachment of the Y moiety to the aromatic residue of the condensed cyclic group is preferably to the 2 or 3 position of dihydronaphthalene, to the 6 or 7 position of chromene or thiochromene, and to the 4 or 5 position of the bicyclooctane moiety, as applicable. Even more preferred is attachment of the Y group to the 2 position of dihydronaphthalene and to the 6 position of chromene or thiochromene.

Preferred $R_{14}$ groups are lower alkyl, particularly methyl and ethyl, and branched chain lower alkyl, particularly i-propyl and t-butyl groups.

In a highly preferred class of compounds of the invention the moiety that is attached to the condensed cyclic group as shown in Formulas 1 and 3, or to the phenyl group, as shown in Formula 2, is the group that is depicted below in Formula 17. $R_1^*$ is methyl, ethyl or n-propyl. It can be seen that in this moiety the orientation about the cyclopropane ring is cis, and the orientation of both double bonds of the diene moiety is trans. Formula 17 also shows the numbering of the cyclopropane ring and of the pentadienoic acid moiety.

Formula 17

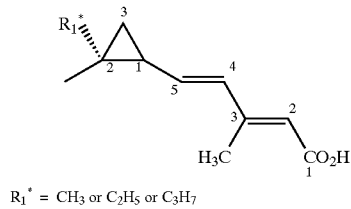

$R_1^* = CH_3$ or $C_2H_5$ or $C_3H_7$

The most preferred class of compounds of the invention are shown below in Formulas 18, 19, 20 and 21 where the $R_{14}^*$ group represents lower alkyl, $X^*$ represents O or S and $R_8^*$ represents H, a salt of the carboxylic acid, or lower alkyl, and $R^*_1$ is methyl, ethyl or n-propyl. Formulas 18, 19, and 21 also show the numbering of the condensed cyclic moieties of these formulas, which numbering is used consistently for the description of the compounds of the invention.

Formula 18

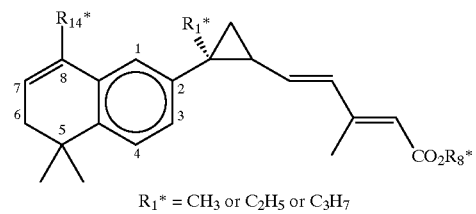

$R_1^* = CH_3$ or $C_2H_5$ or $C_3H_7$

Formula 19

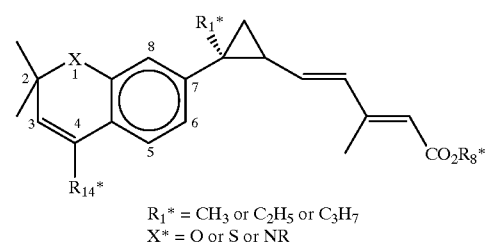

$R_1^* = CH_3$ or $C_2H_5$ or $C_3H_7$
$X^* = O$ or S or NR

Formula 20

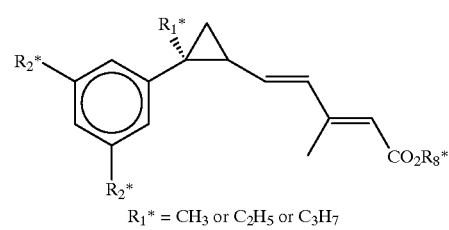

$R_1^* = CH_3$ or $C_2H_5$ or $C_3H_7$

Formula 21

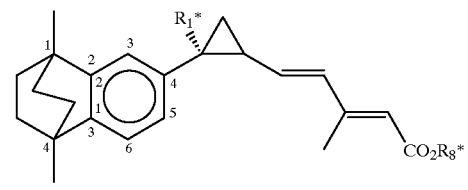

$R_1^* = CH_3$ or $C_2H_5$ or $C_3H_7$
$R_2^* =$ iso-propyl, t-butyl, H and 1-adamantyl The presently most preferred examplary compounds of the invention are designated Compounds 6, 7, 13, 14, 21, 22, 27, 28, 33, 34, 43 and 44. The chemical names are described and the respective structures are shown in the experimental section.

Still more particularly preferred compounds are shown below with reference to formulas 18A, 19A and 20A. The most preferred among these are the acids ($R_8^*$=H), compound 57 (Formula 18A $R_{14}^*$=t-butyl); compound 64 (Formula 18A $R_{14}^*$=i-propyl); compound 87 (Formula 19A $R_{14}^*$=i-propyl); compound 88 (Formula 19A $R_{14}^*$=t-butyl); compound 89 (Formula 19A $R_{14}^*$=n-butyl), and compound 96 (Formula 20A).

Formula 18A

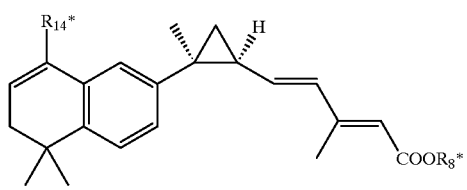

R$_{14}$* = i-propyl or t-butyl
R$_8$* = H or C$_2$H$_5$

Formula 19A

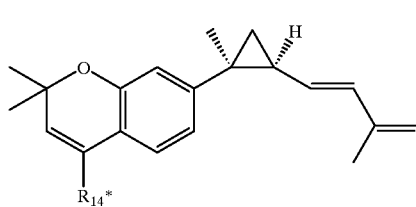

R$_{14}$* = i-propyl, n-butyl or t-butyl
R$_8$* = H or C$_2$H$_5$

Formula 20A

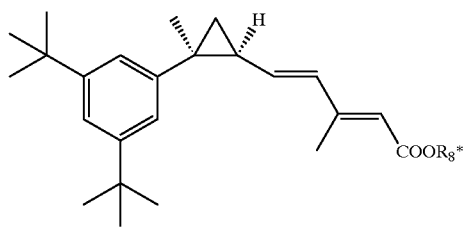

R$_8$* = H or C$_2$H$_5$

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all compounds of the invention.

Reaction Scheme 2

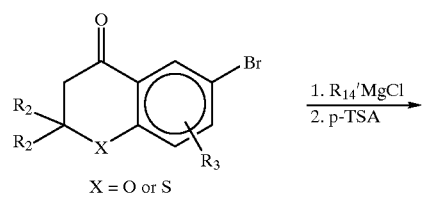

X = O or S
Formula 22

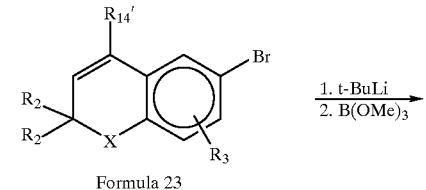

Formula 23

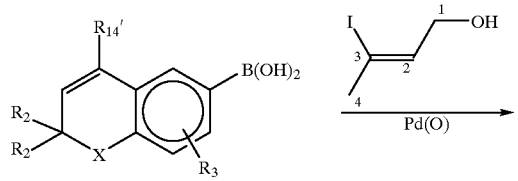

Formula 24

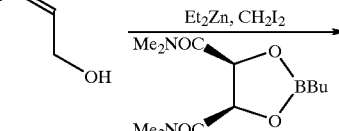

Formula 25

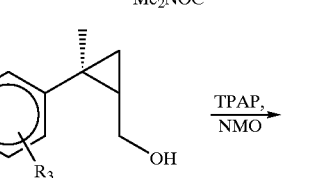

Formula 26

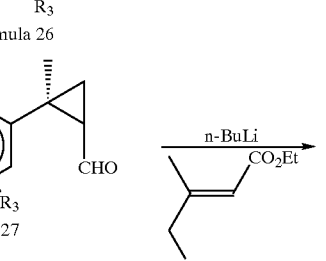

Formula 27

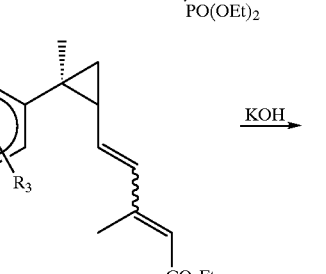

Formula 28

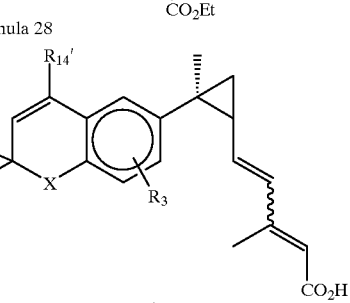

Formula 29

Referring now to Reaction Scheme 2, the synthesis of a preferred class of compounds of the present invention is shown, which fall within the general definition of Formula 1, and where the X* group in Formula 19 represents O or S, R$_2$ and R$_3$ are defined as in connection with Formula 1 above, and R'$_{14}$ is alkyl, aryl or heteroaryl. The starting compound (Formula 22) in this scheme is generally speaking available in accordance with the chemical scientific and patent literature, and/or can be obtained in synthetic steps within the skill of the practicing organic chemist. Examples of the starting compounds of Formula 22 are 2,2-dimethyl-6-bromochroman-4-one and 2,2-dimethyl-6- bromothiochroman-4-one or their 7-bromo positional isomers. The starting compounds can be obtained in accordance with the chemical scientific and patent literature, particularly the teachings of U.S. Pat. No. 5,728,846 the specification of which is expressly incorporated by reference. Other examples for the starting compounds of Formula 22 are 6-bromochroman-4-one and 6-bromothiochroman-4-one.

In accordance with Reaction Scheme 2, the compound of Formula 22 is reacted with a Grignard reagent of the Formula $R'_{14}$—MgBr to provide an intermediate tertiary alcohol that is not shown in the reaction scheme. The tertiary alcohol can also be obtained by reaction of the compound of Formula 22 with a reagent of the formula $R'_{14}$—$X_2$, where $X_2$ is halogen, preferably bromine, in the presence of strong base, such as tertiary-butyl lithium or normal-butyl lithium, as is described in U.S. Pat. No. 5,728,846. The $R'_{14}$ group in the herein described example is lower alkyl, aryl, or heteroaryl but in other examples its scope can be as wide as the definition of the $R_{14}$ group in connection with Formula 1. The Grignard reaction or the reaction with the reagent $R'_{14}$—$X_2$ is typically conducted in an aprotic inert solvent, such as diethylether or tetrahydrofuran (THF). Specific examples for obtaining preferred compounds of the invention with the reagent $R'_{14}$—MgBr are the Grignards obtained from iodomethane or bromoethane, iodoethane or bromoethane, t-butylchloride and i-propylchloride.

The tertiary alcohol is thereafter dehydrated, typically without having been first isolated, by heating with acid such as para toluene sulfonic acid (p-TsA) to yield the 4-alkyl or 4-aryl-6-bromo-chrom-3-ene derivative or its thiochrom-3-ene analog (Formula 23).

The compounds of Formula 23 can also be obtained from the 4-trifluoromethylsulfonyloxy (triflate) derivatives obtained from the ketone compounds of Formula 22 by reacting the latter with sodium bis(trimethylsilyl)amide and 2-[N,N-bis(trifluoromethylsulfonyl)amino]-5-chloropyridine in an inert ether type solvent such as tetrahydrofuran at low temperatures (–78° C. and 0° C.). This reaction is followed by treating the resulting trifluoromethylsulfonyloxy (triflate) derivatives with an organometal derivative obtained from the alkyl, aryl or heteroaryl compound $R'_{14}$—$X_2$ ($X_2$ is halogen) or $R'_{14}$H such that the formula of the organometal derivative is $R'_{14}$—Met (Met stands for metal), preferably Li, as is described in U.S. Pat. No. 5,648,514. The specification of U.S. Pat. No. 5,648,514 is incorporated herein by reference. The reactions leading from compounds of Formula 22 to compounds of Formula 23 through the triflate derivative are not shown in Reaction Scheme 2.

The compounds of Formula 23 are thereafter reacted with trimethoxyboron $(CH_3O)_3B$ to provide the (2,2-dialkyl-4-alkyl, aryl or heteroaryl-2H-chromen-6-yl) boronic acid compounds of Formula 24. Alternatively, when the starting compound of Formula 22 is a thiochroman-4-one then the analogous thiochromene compounds of Formula 24 are obtained. In the ensuing description, in this and other reaction schemes, as applicable, the disclosure is primarily directed to the synthesis of chromene derivatives. However it should be understood that these reaction steps are equally applicable to thiochroman analogs as well. The reaction with trimethoxyboron is typically conducted in an aprotic ether type solvent, preferably diethyl ether or THF at low (–78° C.) temperature. The boronic acid derivatives of Formula 24 are thereafter reacted in an inert solvent, or solvent mixture, such as 10:1 mixture of toluene and methanol, with a 3-iodo-allyl alcohol derivative in the presence of palladium (Pd(0)) catalyst at elevated (approx. 95° C.) temperature, in the presence of some water and an acid acceptor. Reaction Scheme 2 discloses the specific example where the 3-iodo allylic alcohol derivative is 3-iodo-but-2-ene-1-ol and the ensuing description of the scheme is directed to the use of this specific reagent, although it should be understood that homologs and analogs of this reagent can be utilized in reactions which will be apparent to those skilled in the art in light of the present disclosure. The products of the coupling reaction with 3-iodo-but-2-ene-1-ol are 3-(2,2-dialkyl-4-alkyl, aryl or heteroaryl-2H-chromen-6-yl)-but-2(Z)-en-1-ol of Formula 25. The double bond in the buten moiety is in the cis orientation when the 3-iodo allylic alcohol derivative has the cis orientation as shown in the reaction scheme. Compounds of trans orientation can also be obtained provided the orientation of the 3-iodo allilic alcohol reagent is trans.

The 3-(2,2-dialkyl-4-alkyl, aryl or heteroaryl-2H-chromen-6-yl)-but-2(Z)-en-1-ol derivatives of Formula 25 are then converted to the corresponding cyclopropyl derivatives, [2-methyl-2-(2,2-dialkyl-4-alkyl, aryl or heteroaryl-2H-chromen-6-yl)-cyclopropyl]methanol of Formula 26. This "cyclopropylation" reaction employs the reagent diiodomethane in the presence of a suitable catalyst. The cyclopropylation reaction is usually conducted at cold temperature (–25° C.), in an inert solvent such as tetrahydrofuran in an inert (argon) gas atmosphere. In the cyclopropylation reaction the orientation (cis or trans) of the double bond to which the methylene group is attached, is maintained, so that from a cis allylic alcohol of Formula 25 a cis cyclopropyl derivative of Formula 26 is obtained, whereas a trans allylic alcohol of Formula 25 would yield a trans cyclopropyl derivative. A suitable catalyst for the cyclopropylation reaction is the presence of both mercury (II)chloride, and samarium. However, the presence of this catalytic mixture does not provide enantio selectivity for the resulting cyclopropyl derivatives. When enantio selectivity is desired, an optically active tartrate catalyst, specifically N,N-tetramethyl-tartramide borolidine, shown in Reaction Scheme 2, and diethyl zinc ($Et_2Zn$) are used as catalysts. This cyclopropylation reaction using optically active tartrate catalyst is in analogy to a similar reaction (performed on different materials) described in *Journal of Organic Chemistry* (1995) 60 1081–1083.

In the next reaction step the [2-methyl-2-(2,2-dialkyl-4-alkyl, aryl or heteroaryl-2H-chromen-6-yl)-cyclopropyl] methanol derivatives of Formula 26 are oxidized to the "aldehyde stage" to yield [2-methyl-2-(2,2-dialkyl-4-alkyl, aryl or heteroaryl-2H-chromen-6-yl)-cyclopropyl] carbaldehyde derivatives of Formula 27. It will be recognized by those skilled in the art that several reagents are suitable for this oxidation step. The presently preferred reagents and conditions for this reaction include the use of methylene chloride as the solvent, and tetrapropyl ammonium perrnthenate and N-methyl morpholine N-oxide as reagent and catalyst. The oxidation reaction is typically conducted at room temperature. Other suitable reagents for this oxidation reaction include, as it will be readily understood by those skilled in the art, pyridinium dichromate, oxalyl chloride and dimethylsulfoxide or trifluoroacetic anhydride and dimethylsulfoxide. The [2-methyl-2-(2,2-dialkyl-4-alkyl, aryl or heteroaryl-2H-chromen-6-yl)-cyclopropyl]carbaldehyde derivatives of Formula 27 are subsequently reacted with a diethylphosphono reagent. The diethylphosphono reagent shown in the reaction scheme for the present examples is ethyl diethylphosphono-3-methyl-2 (E)-butenoate which can be obtained in accordance with the chemical literature (J. Org. Chem. 1974 Volume 39 p. 821). The reaction with the diethylphosphono reagent is known in the art as the Horner Emmons reaction. It is conducted in the presence of strong base (such as n-butyl lithium) in an inert solvent, such as tetrahydrofuran, usually at low temperature (typically −78° C.) and results in the formation of a double bond to replace the oxo function of the reagent of Formula 27. The resulting products in this example are 3-methyl-5-[2-methyl-2-(2,2-dialkyl-4-alkyl, aryl or heteroaryl-2H-chromen-6-yl)-cyclopropyl]-2,4-dienoic acid ester derivatives of Formula 28. Instead of the diethylphosphono Horner Emmons reagent an analogous Wittig reagent can also be utilized in the coupling reaction. The structure of such a Wittig reagent will be readily apparent to those skilled in the art in light of the present disclosure. The herein described Horner Emmons coupling reaction typically provides as predominant product the isomer where the orientation about the newly formed double bond ($\blacktriangle^4$ of the pentadienoic acid) is trans, and normally only this trans isomer, or predominantly the trans isomer is isolated from the reaction mixture. However, it is also possible to obtain a greater proportion of the corresponding cis isomer by adjusting conditions of the Horner Emmons reaction. The ester compounds of Formula 28 are readily saponified to give the free carboxylic acid derivatives of Formula 29. Other transformations readily apparent to those skilled in the art in light of the present disclosure can also be made on the carboxylic acid ester or carboxylic acid functions of the compounds of Formula 28 and Formula 29, as applicable, and as is described in connection with Formula 13 of Reaction Scheme 1.

oxiranyl]methanol derivatives, or their thiochromen analogs of Formula 30. The allyl alcohol compounds of Formula 25 can be obtained as described in connection with Reaction Scheme 2. The epoxidation reaction can be performed with reagents and under conditions normally used for this purpose in the art, for example with meta-chloroperoxybenzoic acid in methylene chloride solution. There are other epoxidizing agents well known in the art and available to the practicing organic chemist, which are also well suited for the epoxidation reactions of this invention. Some of the known epoxidizing agents are enantio-selective.

The resulting epoxidized primary alcohols of Formula 30 are then subjected to the same sequence of reactions as the cyclopropylmethanol derivatives of Formula 26 are subjected in accordance with Reaction Scheme 2, to provide the 3-methyl-5-[2-methyl-2-(2,2-dialkyl-4-alkyl, aryl or heteroaryl-2H-chromen-6-yl)-oxiranyl]-2,4-dienoic acid derivatives of Formula 31.

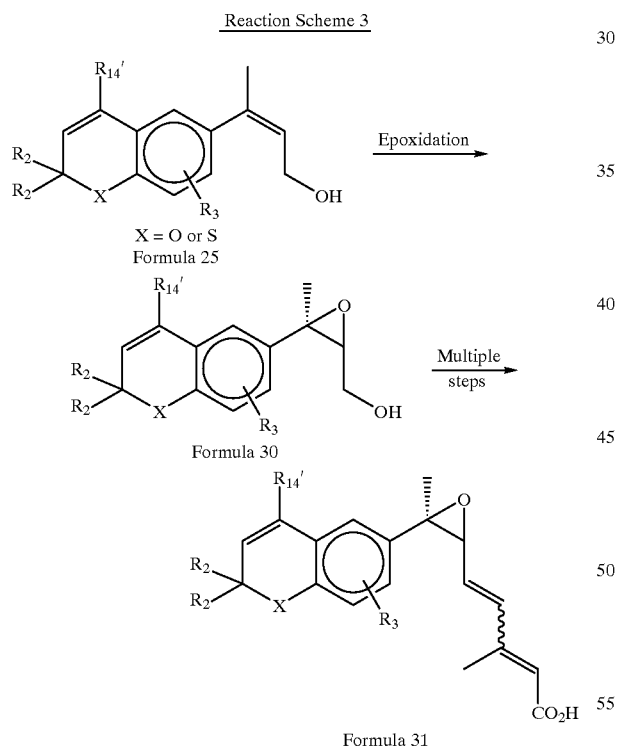

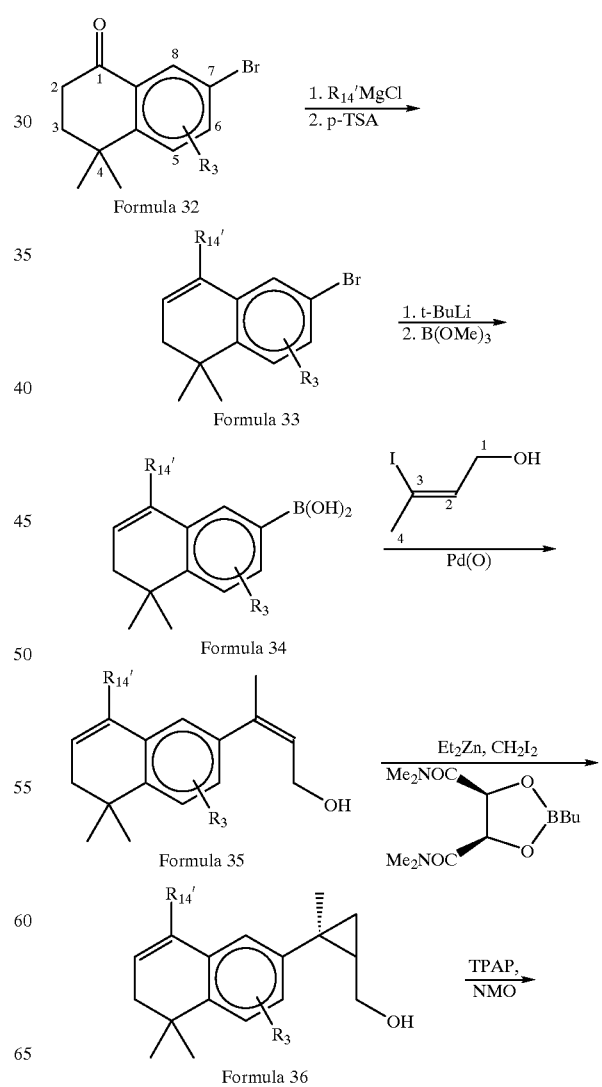

Referring now to Reaction Scheme 3 the reaction step which is important in the preparation of oxiranyl derivatives of the compounds of the invention is shown, for the exemplary compounds which are chromene or thiochrome derivatives. In this reaction the 3-(2,2-dialkyl-4-alkyl, aryl or heteroaryl-2H-chromen-6-yl)-but-2(Z)-en-1-ol derivatives, or the corresponding thiochromen analogs of Formula 25 are subjected to an epoxidation reaction to provide [2-methyl-2-(2,2-dialkyl-4-alkyl, aryl or heteroaryl-2H-chromen-6-yl)-

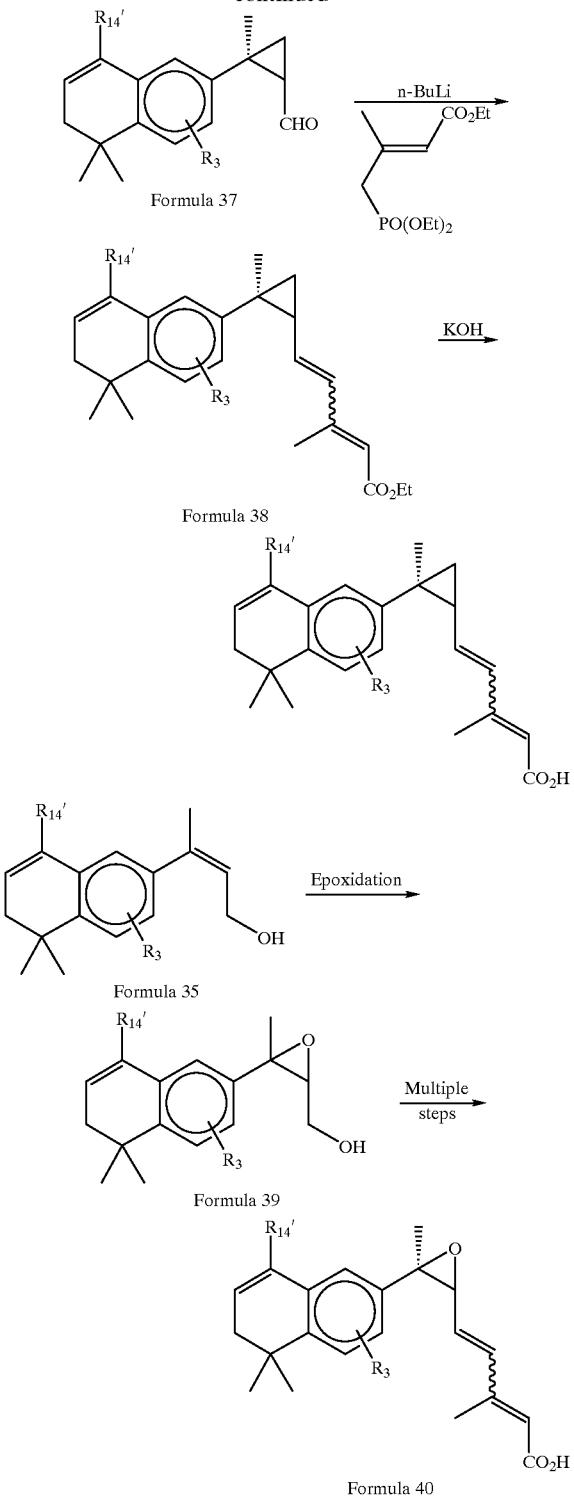

Formula 37
Formula 38
Formula 35
Formula 39
Formula 40

Reaction Scheme 4 discloses the presently preferred process for the synthesis of a preferred class of compounds of the present invention which are 8-alkyl, aryl or heteroaryl 5,5-dimethyl-5,6-dihydronaphtalene derivatives. The starting compounds of this reaction sequence are 6 or 7-bromo (or like halogeno) substituted 1-(2H)-naphthalenones. Of these only the 7 bromo derivative is shown in the scheme by Formula 32. It will be readily understood in this regard by those skilled in the art that compounds used as starting materials in this scheme where the bromo substituent is in the 6-position of the 1-(2H)-naphthalenone gives rise to positional isomers of the presently preferred compounds of the invention.

In the exemplary synthetic route illustrated in Reaction Scheme 4 a preferred starting material in accordance with Formula 32 is 3,4-dihydro-4,4-dimethyl-7-bromo-1(2H)-naphthalenone. The latter compound can be obtained in accordance with the chemical scientific (Johnson et al., J. Med. Chem. 1995, 38, 4764–4767) and patent (U.S. Pat. No. 5,543,534) literature. The Johnson et al. publication and the specification of U.S. Pat. No. 5,543,534 are expressly incorporated herein by reference. The isomeric compound 3,4-dihydro-4,4-dimethyl-6-bromo-1(2H)-naphthalenone can also be obtained in accordance with the chemical scientific (Mathur et al. Tetrahedron, 41, 1509 1516 (1985)) and patent (U.S. Pat. No. 5,543,534) literature. The numbering system employed for these simple naphthalenone derivatives is shown in Formula 32.

As is shown in Reaction Scheme 4, the bromonaphthalenone compounds of Formula 32 are subjected to substantially the same sequence of reactions, under substantially similar conditions, as the chroman-4-one or thiochroman-4-one derivatives in accordance with Reaction Scheme 2. Adaptation of the reaction sequence disclosed in connection with Reaction Scheme 2 to the compounds shown in Reaction Scheme 4 is well within the skill of the artisan in synthetic organic chemistry. For these reasons the reaction sequence shown in Reaction Scheme 4 is described here only briefly. Thus, the 3-(5,5-dimethyl-8-alkyl, aryl or heteroaryl-5,6-dihydronaphthalen-2-yl)-but-2(Z)-en-1-ol compounds of Formula 35 are obtained through the intermediates 7-bromo-3,4-dihydro-4,4-dimethyl-1-alkyl-aryl or heteroaryl)-naphthalene (Formula 33) and (3,4-dihydro-4,4-dimethyl-1-alkyl, aryl or heteroaryl)-naphthalen-7-yl) boronic acid (Formula 34) derivatives. The allyl alcohol derivatives of Formula 35 are subjected to cyclopropylation reaction, as in Reaction Scheme 2, to give rise to [2-methyl-2-(5,5-dimethyl-8-alkyl, aryl or heteroaryl-5,6-dihydro-naphthalen-2-yl)-cyclopropyl]-methanol derivatives of Formula 36. The methanol compounds of Formula 36 are then subsequently oxidized to the aldehyde stage (Formula 37) and then reacted in a Horner Emmons reaction with the reagent ethyl diethylphosphono-3-methyl-2(E)-butenoate to provide 3-methyl-5-[2-methyl-2-(5,5-dimethyl-8-alkyl, aryl or heteroaryl-5,6-dihydro-naphthalen-2-yl)-cyclopropyl]-pentadienoic acid ester derivatives of Formula 38. As is disclosed above, the esters of Formula 38 can be saponified or converted to other derivatives, such as amides or alcohols, within the scope of the invention.

As is still shown in Reaction Scheme 4, the intermediate 3-(5,5-dimethyl-8-alkyl, aryl or heteroaryl-5,6-dihydronaphthalen-2-yl)-but-2(Z)-en-1-ol of Formula 35 is epoxidized in accordance with the present invention to provide [2-methyl-2-(5,5-dimethyl-8-alkyl, aryl or heteroaryl-5,6-dihydro-naphthalen-2-yl)-oxiranyl]-methanol derivatives of Formula 39. As in Reaction Scheme 3, the latter are converted in several steps, to the 3-methyl-5-[2-methyl-2-(5,5-dimethyl-8-alkyl, aryl or heteroaryl-5,6-dihydro-naphthalen-2-yl)-oxiranyl]-pentadienoic acid derivatives of Formula 40.

Reaction Scheme 5

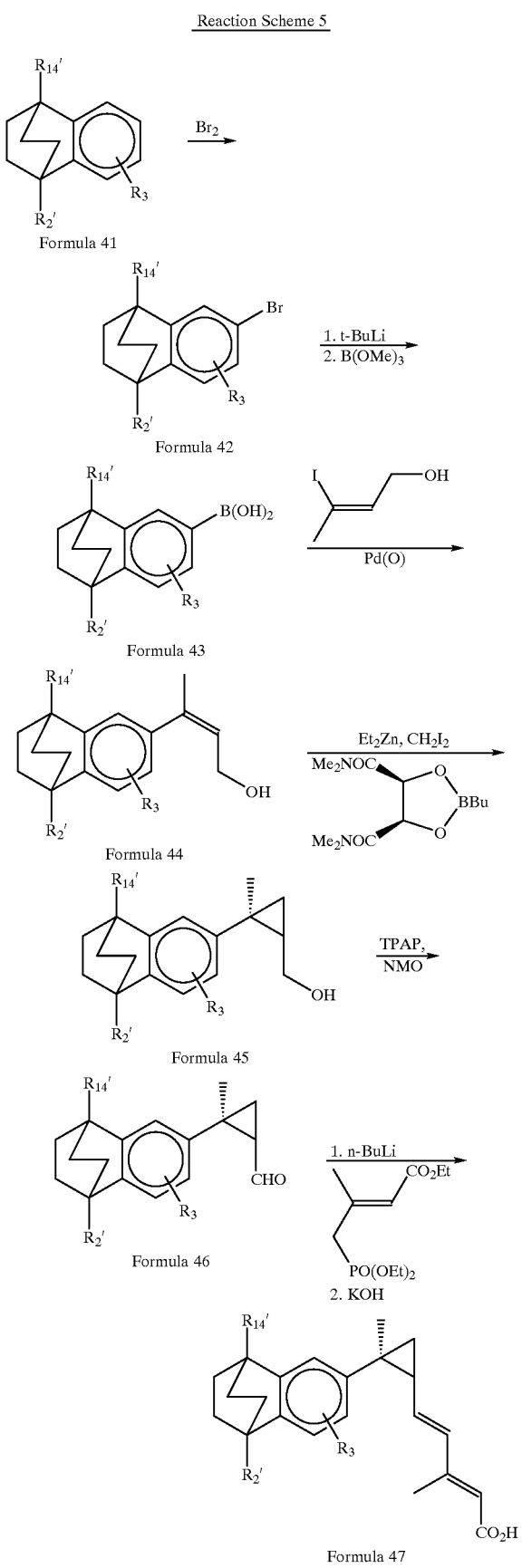

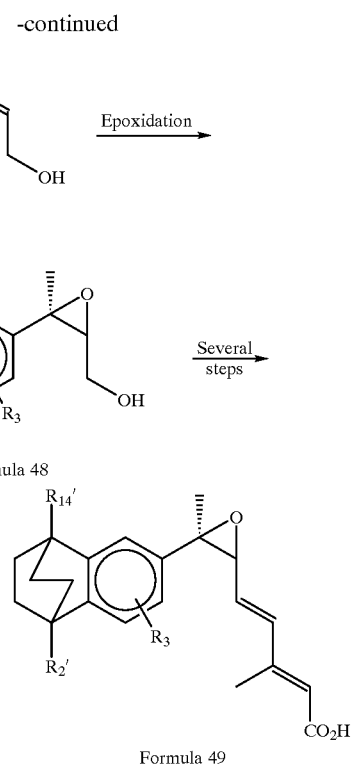

Reaction Scheme 5 discloses a synthetic route to the preparation of a preferred class of compounds of the invention which are [2,3]benzobicyclooctane derivatives. The starting compounds for the syntheses of these exemplary preferred compounds of the invention are [2,3] benzobicyclooctane derivatives where the 1 and 4 positions of the saturated ring are unsubstituted or substituted with a lower alkyl group. In addition, one of these two positions may be substituted with an aryl or heteroaryl group. This is symbolized in the reaction scheme by $R'_{14}$ which is thus designated as lower alkyl, aryl or heteroaryl. However, in the more preferred examples the 1 and 4 positions are both substituted with a lower alkyl group, preferably by a methyl group. An example for a starting material in accordance with Formula 41 is 1,4-dimethyl-[2,3]benzobicyclooctane. The latter compound can be prepared in accordance with the chemical literature, as is described for example by Kagechika et al. J. Med. Chem. 1988 31, 2182, wherein it is named 1,4-ethano-1,2,3,4-tetrahydro-1,4-dimethylnaphthalene (see page 2190 of the Kagechika et al. reference).

The disubstituted [2,3]benzobicyclooctane compounds of Formula 41 are brominated in accordance with Reaction Scheme 5. The bromination can be conducted in any number of solvents suitable for bromination of aromatic compounds, for example in acetic acid. Depending on the nature of the $R'_{14}$ $R'_2$ and $R_3$ substituents the bromination reaction may give rise to a mixture of poistional isomers, of which only one is shown in Formula 42. It will be readily understood by those skilled in the art that in these and the other herein described reaction schemes positional isomers on the aromatic (benzene ring) moiety of the the chromen, thiochromen, dihydronaphthalene and benzobicyclooctane compounds will give rise to the corresponding positional isomers of the herein described prefered compounds of the invention. As is shown in Formulas 1, 2, and 3 these isomers are still within the scope of the invention.

The 1,4-disubstituted-4-bromo-[2,3]benzobicyclooctane compounds of Formula 42 are then subjected to subtantially the same sequence of reactions which is described in connection with Reaction Schemes 2 and 4, to yield the 1,4-disubstituted [2,3][(benzo-4-yl)-2-methyl-cyclopropyl]pentadienoic acid]bicyclooctane and 1,4-disubstituted [2,3][(benzo-4-yl)-2-methyl-oxiranyl-pentadienoic acid]bicyclooctane derivatives of Formulas 47 and 49, respectively.

Reaction Scheme 6

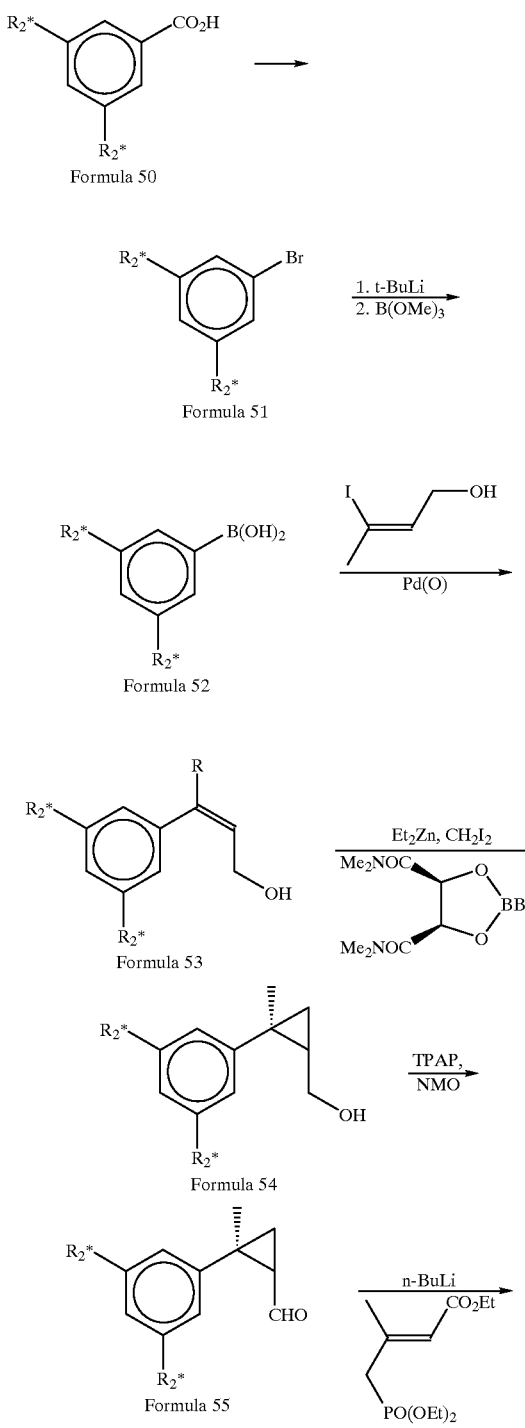

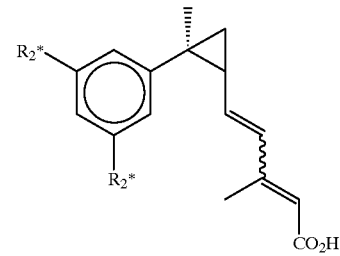

Reaction Scheme 6 discloses a presently preferred synthetic route to a preferred class of compounds of the invention which are disubstituted phenyl-cyclopropyl-pentadienoic acid derivatives. Suitable starting materials for the synthesis are 3,5 disubstituted benzoic acid derivatives shown in the reaction scheme by Formula 50, where the $R^*_2$ group may represent any group defined as $R_2$ in connection with Formula 2, but is preferably an alkyl group, and most preferably tertiary butyl, iso-propyl or 1-adamantyl. The compounds of Formula 50 are generally speaking available in accordance with the chemical literature. 3,5-Di-t-butylbenzoic acid and 3,5-di-i-propylbenzoic acid serve as preferred examples; these compounds are commercially available from Aldrich Chemical Company.

As is shown in Reaction Scheme 6, the 3,5-disubstituted benzoic acids of Formula 50 are subjected to a Hunsdiecker or analogous reaction wherein the carboxylic acid function is replaced by a halogen, preferably bromine. The Hunsdiecker reaction (or like reactions) per se are well known in the art. The product of the Hunsdiecker or like reaction is a 3,5-disubstituted bromobenzene shown by Formula 51. As is well known in the art, the 3,5-disubstituted bromobenzenes of Formula 51 can also be obtained by other than the herein-described chemical reactions, and some may be available commercially as well. The 3,5-disubstituted bromobenzenes of Formula 51 are converted to the corresponding boronic acid derivatives of Formula 52 as in the previously described reaction schemes. The boronic acid derivatives of Formula 52 are subjected to the same sequence of reactions which are described in connection with Reaction Schemes 2, 4, and 5. The end products of these reactions, shown in Reaction Scheme 6 by Formulas 56 and 58, respectively, are 5-[2-(3,5-dialkyl-phenyl)-2-methyl-cyclopropyl)-3-methyl-penta-2,4-dienoic acid] and 5-[2-(3,5-dialkyl-phenyl)-2-methyl-oxiranyl)-3-methyl-penta-2,4-dienoic acid] derivatives. As noted above, preferred compounds in accordance with this reaction scheme are those where both $R^*_2$ groups represent tertiary butyl, or both $R^*_2$ groups are iso-propyl, or where one of the two $R_2^*$ groups is H and other is 1-adamantyl. The adamantyl derivative is presently preferably made in an analogous but somewhat different reaction sequence that involves a coupling reaction between 4-(1-adamantyl) phenyltrifluoromethanesulfonate and 3-iodo-O-triisopropylsilyl-but-2(Z)-ene-ol-3-boronic acid. This sequence of reactions is described in detail in the experimental section.

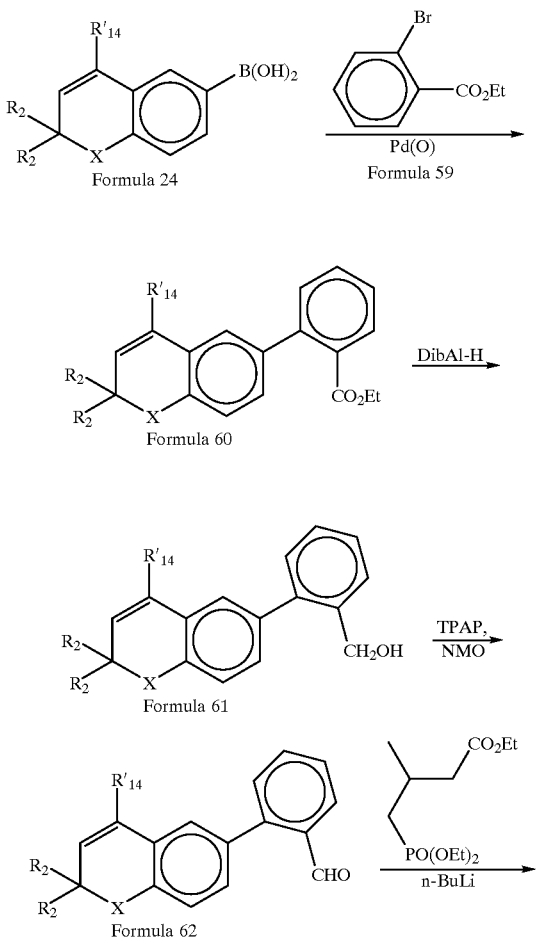

Reaction Scheme 7

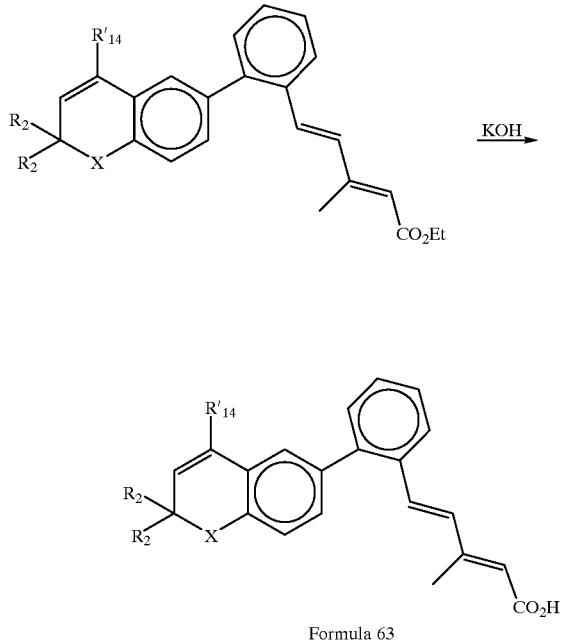

Formula 63

Reaction Scheme 7 discloses the presently preferred synthesis of a class of preferred compounds of the invention which include an aryl, heteroaryl or cycloalkyl group (other than cyclopropyl) covalently linked to the pentadienoic acid moiety. The reaction scheme specifically shows this synthetic route as applied to chrom-3-ene and thiochrom-3-ene derivatives in the situation where the aryl group is 1,2-substituted phenyl. Those having skill in the art will however readily understand that by analogy this synthetic scheme is applicable to the synthesis of numerous other compounds of the invention.

As is shown in the reaction scheme, the (2,2-dialkyl-4-alkyl, aryl or heteroaryl-2H-chromen-6-yl) boronic acid compounds of Formula 24 (or their corresponding thiochrom-3-ene analogs) are reacted with ethyl 2-bromobenzoate in the presence of Pd(0) catalyst in an inert solvent or solvent mixture, such as toluene and methanol, to provide 2-(2,2-dialkyl-4-alkyl, aryl or heteroaryl-2H-chromen-6-yl)benzoic acid ethyl ester compounds of Formula 60. The reagent ethyl 2-bromobenzoate is available in accordance with the chemical literature, see for example J. Org. Chem. 14 (1949) 509, 512 and Helv. Chim. Acta 39 (1956) 505–511. Other examples of reagents which can be used in this reaction instead of ethyl 2-bromobenzoate are: ethyl 2-bromopyridine-3-carboxylate, ethyl 4-bromopyridine-3-carboxylate, ethyl 3-bromothiophene-2-carboxylate, ethyl 2-bromothiophene-3-carboxylate, ethyl 3-bromofuran-2-carboxylate, ethyl 2-bromofuran-3-carboxylate, ethyl cis 2-bromo-cyclopentanecarboxylate and ethyl cis 2-bromo-cyclohexanecarboxylate. However, in the ensuing desription the primary emphasis remains on the 1,2 substituted phenylene derivative actually shown in the reaction scheme.

The carboxylic acid ester function of the 2-(2,2-dialkyl-4-alkyl, aryl or heteroaryl-2H-chromen-6-yl)benzoic acid ethyl ester compounds of Formula 60 is then reduced with a suitable reducing agent, such as di-iso-butyl aluminum hydride (diBAl H) in an ether-like solvent, to provide the corresponding 2-(2,2-dialkyl-4-alkyl, aryl or heteroaryl-2H- chromen-6-yl)-phenylmethanols (primary alcohols) of Formula 61. The primary alcohols of Formula 61 are thereafter oxidized to the corresponding 2-(2,2-dialkyl-4-alkyl, aryl or heteroaryl-2H-chromen-6-yl)benzaldehydes of Formula 62 in an oxidation reaction that is analogous to the oxidation of the methanol derivatives of Formula 26 in Reaction Scheme 2. The benzaldehyde derivatives of Formula 62 are thereafter subjected to a Horner Emmons reaction with the reagent ethyl diethylphosphono-3-methyl-2(E)-butenoate in analogy to the related reaction described in Reaction Scheme 2. The resulting 3-methyl-5-[2-(2,2-dialkyl-4-alkyl, aryl or heteroaryl-2H-chromen-6-yl)-phenyl]-penta-2,4-dienoic acid ethyl esters are a preferred class of compounds of the present invention. The ester function of these compounds is saponified to provide the corresponding carboxylic acids, or their salts. The carboxylic acid ester or acid functions can also be subjected to other transformations well known in the art to provide still further compounds of the invention.

It will be readily recognized by those skilled in the art that the reactions described in connection with Reaction Scheme 7 can also be performed starting with the (3,4-dihydro-4,4-dimethyl-8-alkyl, aryl or heteroaryl)-naphthalen-7-yl) boronic acid derivatives of Formula 34, with the [2,3] benzobicyclooctan boronic acid derivatives of Formula 43, and with the 3,5-disubstituted-phenyl boronic acid derivatives of Formula 52, to yield the corresponding preferred compounds of the invention.

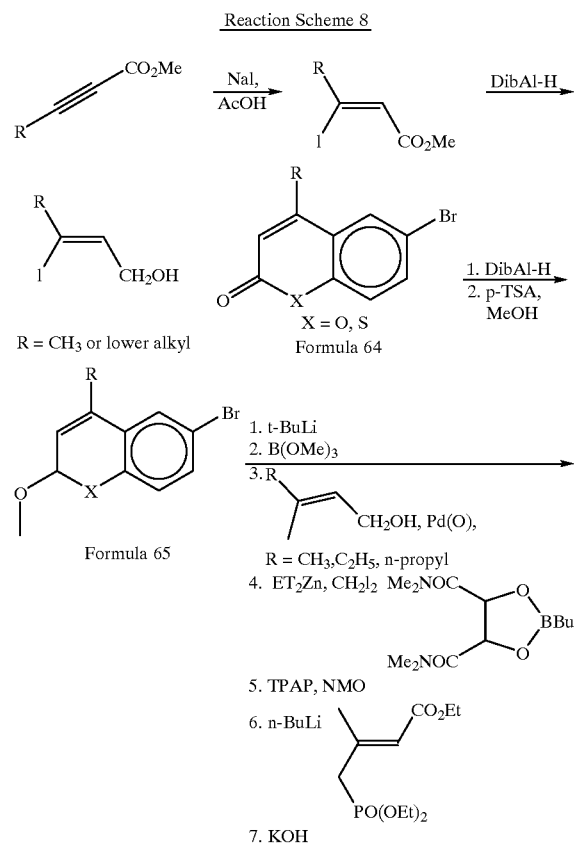

Reaction Scheme 8

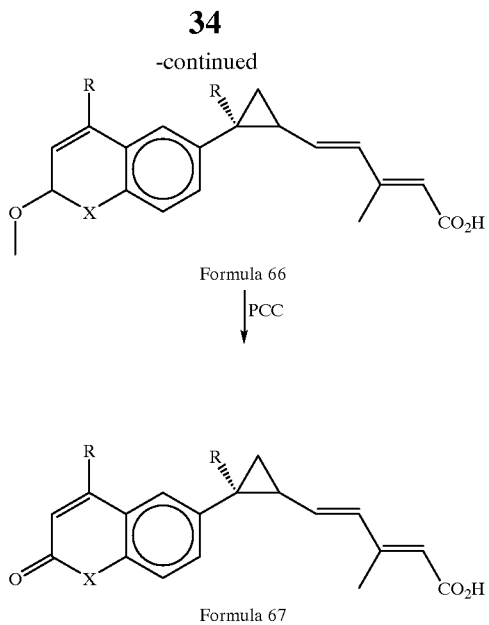

Reaction Scheme 8 discloses an example for preparing a compound of the invention where, with reference to Formula 1, the two $R_2$ groups jointly comprise an oxo (O=) group, and where X is O or S (chromene, or thiochromene derivatives). The examplary starting material in this scheme is a compound of Formula 64 which is a 4-methyl-6-bromo-3-chromene-2-one or its thio analog. Both of these compounds are available in accordance with the chemical literature; for 4-methyl-6-bromo-3-chromene-2-one see J. Ind. Chem. Soc. (1940) 17 65–67, and for its thio analog see Bull. Chem. Soc. Jap. (1986) 53 2046–2049. These two publications are expressly incorporated herein by reference.

In the first reaction shown in the scheme, the ketone function of the compounds of Formula 64 is reduced with a suitable reducing agent, (such as DIBAL-H) and a methyl ether is formed with methanol in the presence of acid, such aspara-toluene sulfonic acid. The resulting methyl ether of Formula 65 is reacted with trimethoxyboron, and the resulting boronic acid compound (analogous to the compounds of Formula 24 in Reaction Scheme 2) is subjected to the same sequence of reactions as the boronic acid compound of Formula 24 in Reaction Scheme 2. The resulting 2,4-dienoic acid derivatives wherein the chromene nucleus still retains the methoxy protecting group in the 2-position are shown in Formula 66. The compounds of Formula 66 are oxidized with pyridinium chlorochromate (PCC) to provide the corresponding chromene-2-one derivatives or their thio analogs Formula 67.

The above described reaction sequence can also be employed, with such modifications that will become readily apparent to those skilled in synthetic organic chemistry, to the synthesis of analogous dihydronaphthalene compounds of the invention within the scope of Formula 1 where the two $R_2$ groups jointly form an oxo group.

The syntheses of the specific preferred compounds shown by Formulas 18A, 19A and 20A are shown in Reaction Schemes 9, 10, and 11, respectively, and a detailed description of these synthetic processes is provided in the experimental section.

Reaction Scheme 9
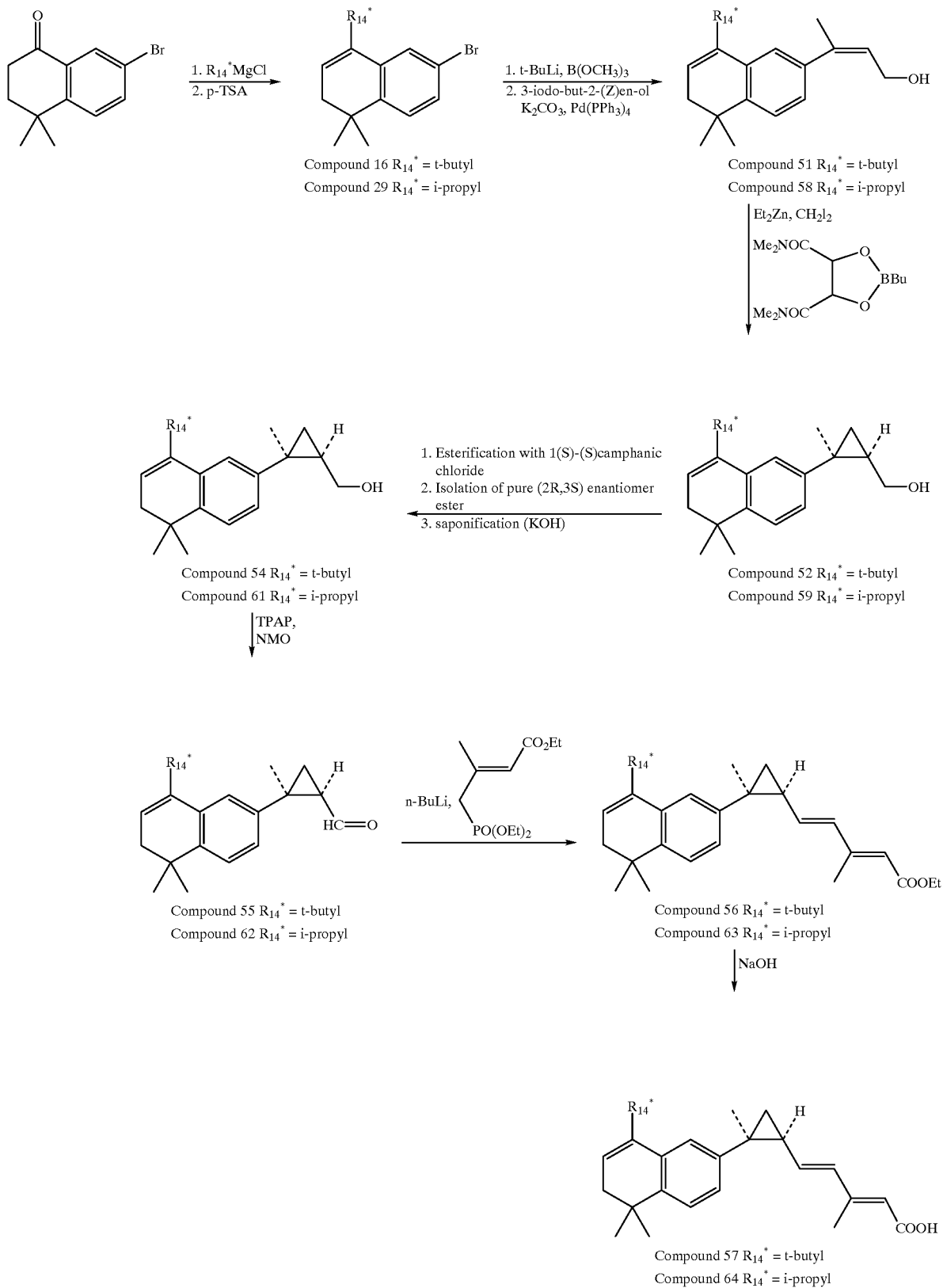

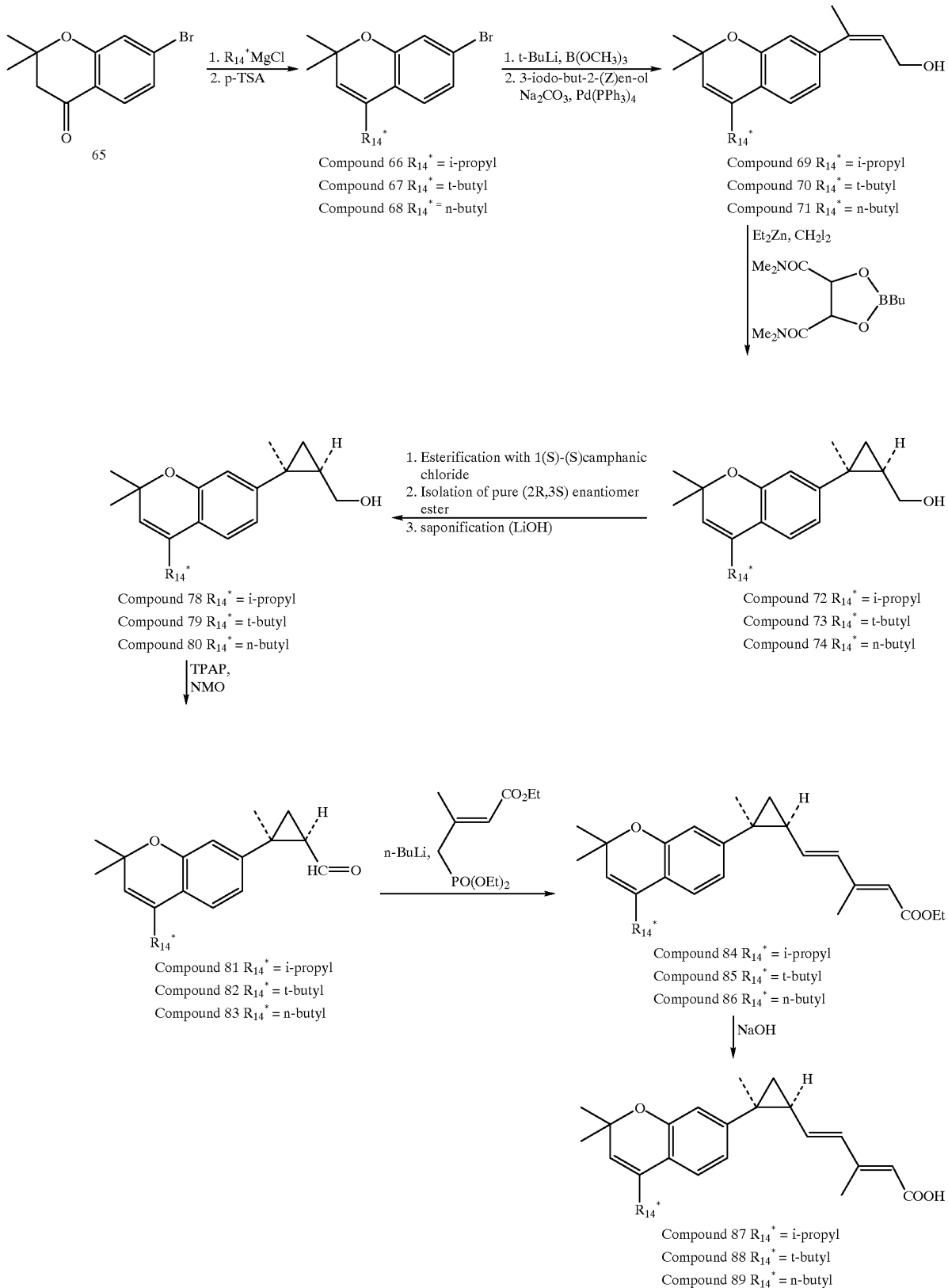

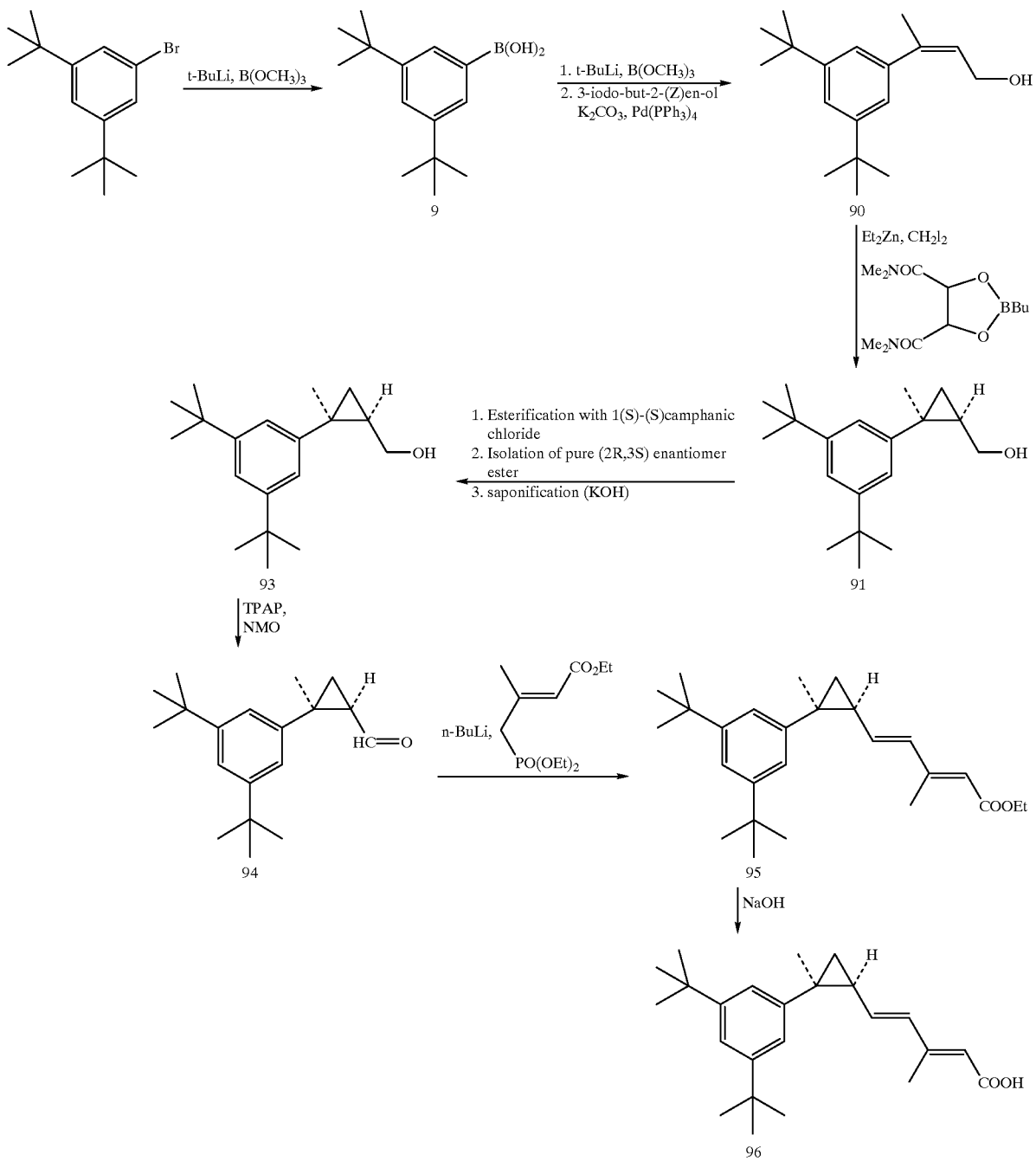

Reaction Scheme 11

SPECIFIC EMBODIMENTS

3-Iodo-pent-2(Z)-en-1-ol (Compound 1)

A solution of ethyl pent-2-ynoate (2.0 g, 15.9 mmol), acetic acid (15 mL) and sodium iodide (3.1 g, 20.7 mmol) was heated for 36 hours at 95° C. The reaction was cooled to ambient temperature and major portion of the solvent was removed under reduced pressure. The crude mixture was diluted with ether (100 mL), washed with water (20 mL), aq. sodium thiosulfate (20 mL), brine (20 mL), dried and the solvent was removed under reduced pressure to afford ethyl 3-iodo-pent-2(Z)enoate.

To a cold (−78° C.) solution of ethyl 3-iodo-pent-2(Z) enoate (3.1 g, prepared as described above) in dichloromethane (15 mL), was added diisobutylaluminum hydride (1M solution in dichloromethane, 27 mL, 27 mmol). The resulting mixture was gradually warmed to −10° C., and quenched by adding methanol (2 mL), water (10 mL) and 10% HCl (10 mL). The mixture was washed with water, 10% sodium carbonate, brine, dried with $MgSO_4$ and the solvent was distilled off to afford the title compound as a colorless oil.

¹H NMR (300 MHz, CDCl₃): d 1.10 (t, J=7.3 Hz, 3H), 2.55 (q, J=7.3 Hz, 2H), 4.21 (d, J=5.5 Hz, 2H), 5.84 (t, J=5.5 Hz, 1H).

(3,5-Diisopropylphenyl)boronic acid (Compound 2)

3,5-Diisopropyl bromobenzene was prepared by the procedure reported in Le Noble, W. J. et al. J. Org. Chem. 36, (1971) 193–196. To a cold (−78° C.) solution of 3,5-diisopropyl bromobenzene (2.4 g, 10 mmol) in tetrahydrofuran (THF) (20 mL) was added t-BuLi (1.7M solution in pentane, 12.9 mL, 22 mmol) dropwise. The mixture was stirred for 1 hour between −78° C. and −20° C. Then the reaction mixture was cooled to −78° C. and trimethylborate (2.3 g, 22 mmol) was added dropwise via a syringe. The mixture was stirred and gradually warmed to ambient temperature over 1 hour and quenched with aqueous ammonium chloride solution. The mixture was extracted with ethyl acetate (3×30 mL), the combined organic layers were washed with brine, dried and the solvent removed by evaporation. The resulting residue, crude product was used in the next step without further purification.

3-(3,5-Diisopropylphenyl)-pent-2(Z)-en-1-ol (Compound 3)

Argon gas was bubbled for 5 minutes into a solution of 3,5-diisopropylphenylboronate (Compound 2, 2.4 g crude), toluene (80 mL), methanol (8 mL), K₂CO₃ (3 g) in water (10 mL) and 3-iodo-pent-2(Z)-en-1-ol (Compound 1). Then Pd(PPh3)₄ (66 mg) was added and the mixture was heated to 95° C. for 16 hours. Thereafter the reaction mixture was cooled to ambient temperature and washed with brine and dried with MgSO₄, and the solvent was removed by evaporation. The residual product was purified by column chromatography (silica gel, hexane:EtAc 9:1) to obtain the title compound as a pale yellow oil.

¹HNMR (CDCl₃): 1.03 (t, J=7.1 Hz, 3H), 1.25 (d, J=7.0 Hz, 12H), 2.40 (q, 7.1 Hz, 2H), 2.88 (s, J=7.0 Hz, 2H), 4.08 (d, J=6.6 Hz, 2H), 5.65 (t, J=6.6, 1H), 6.79 (d, J=1.5 Hz, 2H), 6.99 (brs, 1H).

(−)-2(R),3(S)-Methano-3-(3,5-diisopropylphenyl)-pentan-1-ol (Compound 4)

To a cold (−50° C.) mixture of 3-(3,5-diisopropylphenyl)-pent-2(Z)-en-1-ol (Compound 3, 600 mg, 2.4 mmol), 1,3-dioxa-2-butyl-4,5-dicarbo-N,N-dimethylamide-2-borolane (1.75 g, 6.4 mmol), (derived from D-(−)-N,N-tetramethyltartaramide and n-butylboronic acid, for preparation of this reagent see; J. Org. Chem. 1995, 60, 1081), molecular sieves (1.8 g), dichloromethane (15 mL), was added freshly prepared Zn(CH₂I)2. DME complex in dichloromethane (1.8M solution, 64 mmols, for preparation see; J. Org. Chem. 1995, 60, 1081), via canula dropwise (15 min). The mixture was stirred at 20° C. for 16 hours and then quenched by adding ammonium chloride solution. The mixture was extracted with dichloromethane, the combined organic layers were washed with ammonium chloride, brine, dried and the solvent was removed by evaporation. Purification by chromatography gave the title compound as a colorless oil.

[a]_D^{20° C.}=−9.9°; c=0.9 g/100 mL; solvent-dichloromethane; ¹HNMR (CDCl₃): d 0.72–0.82 (m, 5H), 1.23 (d, J=7.0 Hz, 12H), 1.88–2.00 (m, 1H), 2.66 (s, J=7.0 Hz, 2H), 3.26 (d, J=7.1 Hz, 2H), 6.91 (brs, 1H), 6.95 (d, J=1.9 Hz, 2H).

(−)-2(R),3(S)-Methano-3-(3,5-diisopropylphenyl)-pentanal (Compound 5)

To a solution of (−)-2(R),3(S)-methano-3-(3,5-diisopropylphenyl)-pentan-1-ol (Compound 4, 180 mg, 0.7 mmol), in dichloromethane (8 mL), acetonitrile (0.5 mL) was added N-methylmorpholine-N-oxide (234 mg, 2 mmol), molecular sieves (500 mg) and tetrapropylammonium perruthenate (5 mg). The mixture was stirred for 1 hour and thereafter it was passed through a column of silicagel eluted with hexane and ethylacetate (9:1). Collected fractions containing product were combined and the solvent was distilled off to afford the title compound as a colorless oil. The product was used in the next step without further purification.

¹HNMR (CDCl₃): d 0.82 (t, J=7.1 Hz, 3H), 1.23 (d, J=7.0 Hz, 12H), 1.35–1.45 (m, 2H), 1.75–1.97 (m, 3H), 2.83 (s, J=7.0 Hz, 2H), 6.91 (brs, 3H), 8.38 (d, J=7.4 Hz, 1H).

Ethyl-7-[3,5-diisopropylphenyl]-6(S),7(S)-methano-3-methyl-2(E),4(E)-nonadienoate (Compound 6)

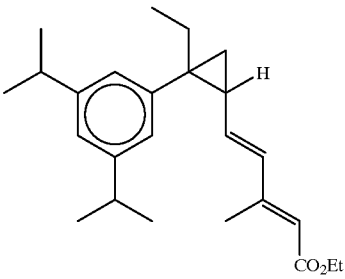

To a solution of diethyl(E)-3-ethoxycarbonyl-2-methylallylphosphonate (950 mg, 3.6 mmol) in THF (12 ml), 1,3-dimethyl-3,4,5,6-tetrahydro-2(1H)-pyrimidinone (2.7 ml) at −78° C. was added n-BuLi (2.3 ml, 3.6 mmol) dropwise. The mixture was stirred for five minutes. Then (−)-2(R),3(S)-methano-3-(3,5-diisopropylphenyl)-pentanal (Compound 5, 187 mg, 0.72 mmol) in THF (2+2 ml) was added dropwise. The mixture was stirred and gradually the reaction temperature was allowed to rise to −10° C. At that time thin layer chromatography indicated that the reaction was complete, water was added to the reaction mixture and the mixture was extracted with ethyl acetate. The combined organic layers were washed with water, brine, then dried (MgSO₄) and the solvent was removed by evaporation. Silicagel column chromatography (3% ethyl acetate in hexane) gave a mixture of two isomers, the title compound and the 13-cis isomer. The title compound was isolated as a colorless oil by high pressure liquid chromatography (HPLC, Partisil-10 semi preparative column, 1% ethyl acetate in hexane).

¹H NMR (300 MHz, CDCl₃): d 0.83 (t, J=7.5 Hz, 3H), 1.03 (t, J=4.9 Hz, 1H), 1.15–1.20 (m, 1H), 1.21 (d, J=7.5 Hz, 12H), 1.26 (t, J=7.2 Hz, 3H), 1.30–1.42 (m, 1H), 1.65–1.80 (m, 2H), 1.98 (s, 3H), 2.84 (m, 2H), 4.13 (q, J=7.2 Hz, 2H), 5.24 (dd, J=9.9 Hz, 15.6 Hz, 1H), 5.62 (s, 1H), 6.19 (d, J=15.6 Hz, 1H), 6.86 (s, 2H), 6.89 (s, H).

(+) 7-[3,5-Diisopropylphenyl]-6(S),7(S)-methano-3-methyl-2(E),4(E)-nonadienoic acid (Compound 7)

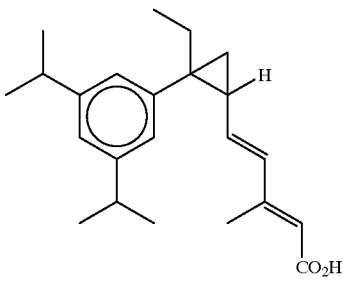

To a solution of ethyl-7-[3,5-diisopropylphenyl]-6(S),7(S)-methano-3-methyl-2(E),4(E)-nonadienoate (Compound 6, 235 mg, 0.64 mmol) in THF (4.1 ml) and methanol (8.2 ml) was added NaOH (1M solution, 3.4 ml). The mixture was heated to 75° C. for 15 hours. At that time thin layer chromatography indicated that the reaction was complete. The solvents, THF and methanol were removed under reduced pressure and the residue was diluted with ethyl acetate. The mixture was acidified with 10% HCl to pH 2. The aqueous and organic layers were separated and the organic layer was washed with water and brine and therafter dried with $MgSO_4$. The solvent was removed by evaporation. The title compound (white solid) was isolated from the residue by silicagel chromatography.

Optical Rotation $[\alpha]_D^{20°\ C.} = +25.7°$, solvent dichloromethane, c=0.0025 g/mL, l=1;

$^1$H NMR (300 MHz, $CDCl_3$): d 0.86 (t, J=7.2 Hz, 3H), 1.07 (t, J=5.0 Hz, 1H), 1.15–1.23 (m, 1H), 1.21 (d, J=7.2 Hz, 12H), 1.35–1.45 (m, 1H), 1.68–1.80 (m, 2H), 1.98 (s, 3H), 2.75–2.90 (m, 2H), 5.33 (dd, J=10.0, 15.5 Hz, 1H), 5.65 (s, 1H), 6.21 (d, J=15.5 Hz, 1H), 6.86 (s, 2H), 6.89 (s, 1H).

3,5-di-tert-butylphenylboronic acid (Compound 9)

To a cold (−78° C.) solution of 3,5-tert-butyl bromobenzene (available from Lancaster Co., 2.1 g, 8.2 mmol) in tetrahydrofuran (THF) (20 mL) was added t-BuLi (1.7M solution in pentane, 9.7 mL, 16.4 mmol) dropwise. The mixture was stirred for 1 hour between −78° C. and −20° C. The reaction was cooled to −78° C. and trimethylborate (1.7 g, 16.4 mmol) was added via syringe dropwise. The mixture was stirred and gradually warmed to ambient temp. over 1 hour and quenched with aqueous ammonium chloride solution. The mixture was extracted with ethylacetate (3×30 mL), the combined organic layer was washed with brine, dried and the solvent was removed. The crude product was used in the next step without further purification.

3-(3,5-Di-tert-butylphenyl)-hex-2(Z)-en-1-ol (Compound 10)

Employing the procedure used for the preparation of 3-(3,5-diisopropylphenyl)-pent-2(Z)-en-1-ol (Compound 3), 3,5-di-tert-butylphenylboronic acid (Compound 9) was converted to the title compound using 3-iodo-hex-2(Z)-en-ol (Compound 15) as the coupling agent.

$^1$HNMR ($CDCl_3$): δ 0.90 (t, J=7.1 Hz, 3H), 1.33 (s, 18H), 1.33–1.45 (m, 2H), 2.37 (t, J=7.1 Hz, 2H), 4.08 (d, J=6.7 Hz, 2H), 5.66 (t, J=6.6, 1H), 6.94 (d, J=1.5 Hz, 2H), 7.32 (brs, 1H).

(−)-2(R),3(S)-Methano-3-(3,5-di-tert-butylphenyl)-hexan-1-ol (Compound 11)

Employing the procedure used for the preparation of (−)-2(R),3(S)-methano-3-(3,5-diisopropylphenyl)-pentan-1-ol (Compound 4), 3-(3,5-di-tert-butylphenyl)-hex-2(Z)-en-1-ol (Compound 10) was converted to the title compound.

$[\alpha]_D^{20°\ C.} = -48.5°$; c=0.55 g/100 mL; solvent-dichloromethane;

The % yield was determined to be >95%.

$^1$HNMR ($CDCl_3$): δ 0.78–0.90 (m, 5H), 1.32 (s, 18H), 1.20–1.34 (m, 6H), 1.85 (m, 1H), 3.35 (brs, 2H), 7.12 (d, J=1.8 Hz, 2H), 7.24 (d, J=1.8 Hz, 1H).

(−)-2(R),3(S)-Methano-3-(3,5-di-tert-butylphenyl)-hexanal (Compound 12)

By employing the procedure used for the preparation of (−)-2(R),3(S)-methano-3-(3,5-diisopropylphenyl)-pentanal (Compound 5), (−)-2(R),3(S)-Methano-3-(3,5-di-tert-butylphenyl)-hexan-1-ol (Compound 11) was converted into the title compound.

$[\alpha]_D^{20°\ C.} = -20.5°$; c=0.42 g/100 mL; solvent-dichloromethane;

$^1$HNMR ($CDCl_3$): δ 0.84 (t, J=7.1 Hz, 3H), 1.23 (s, 18H), 1.25–1.45 (m, 4H), 1.75–1.97 (m, 3H), 7.00 (d, J=1.7 Hz, 2H), 7.27 (d, J=1.7 Hz, 1H), 8.36 (d, J=7.4 Hz, 1H).

(+) Ethyl-7-[3,5-di-tert-butylphenyl]-6(S),7(S)-methano-3-methyl-2(E),4(E)-decadienoate (Compound 13)

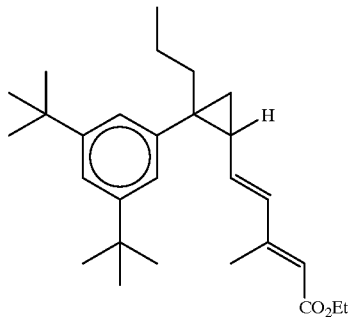

Employing the procedure used for the preparation of ethyl-7-[3,5-diisopropylphenyl]-6(S),7(S)-methano-3-methyl-2(E),4(E)-nonadienoate (Compound 6), (−)-2(R),3(S)-methano-3-(3,5-di-tert-butylphenyl)-hexanal (Compound 12) was converted into the title compound.

$[\alpha]_D^{20°\ C.} = +70.5°$; c=0.24 g/100 mL; solvent-dichloromethane;

$^1$H NMR (300 MHz, $CDCl_3$): δ 0.84 (t, J=7.5 Hz, 3H), 1.05 (t, J=4.9 Hz, 1H), 1.21 (dd, J=4.5, 8.3 Hz, 1H), 1.28 (t, J=7.5 Hz, 3H), 1.30 (s, 18H), 1.30–1.40 (m, 3H), 1.64–1.76 (m, 2H), 2.00 (s, 3H), 4.14 (q, J=7.2 Hz, 2H), 5.24 (dd, J=9.9 Hz, 15.6 Hz, 1H), 5.64 (s, 1H), 6.20 (d, J=15.6 Hz, 1H), 7.03 (d, J=1.8 Hz, 2H), 7.23 (d, J=1.8 Hz, 1H).

(+) 7-[3,5-Di-tert-butylphenyl]-6(S),7(S)-methano-3-methyl-2(E),4(E)-decadienoic acid (Compound 14)

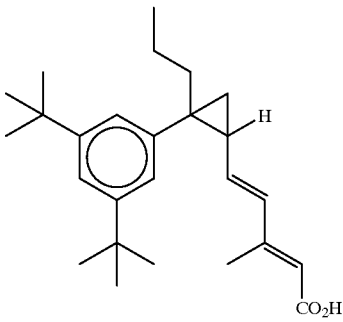

Employing the procedure used for the preparation of (+) 7-[3,5-diisopropylphenyl]-6(S),7(S)-methano-3-methyl-2(E),4(E)-nonadienoic acid (Compound 7), (+) ethyl-7-[3,5-di-tert-butylphenyl]-6(S),7(S)-methano-3-methyl-2(E),4(E)-decadienoate (Compound 13) was converted into the title compound.

Optical Rotation $[\alpha]^{20°}{}^{C}{}_{D}=+80.4°$, solvent is dichloromethane, c=0.0035 g/mL, 1=1;

$^1$H NMR (300 MHz, CDCl$_3$): δ 0.87 (t, J=7.2 Hz, 3H), 1.23 (t, J=5.0 Hz, 1H), 1.20–1.45 (m, 4H), 1.31 (s, 18H), 1.65–1.80 (m, 2H), 2.00 (s, 3H), 5.31 (dd, J=10.0, 15.5 Hz, 1H), 5.66 (s, 1H), 6.23 (d, J=15.5 Hz, 1H), 7.03 (d, J=1.7 Hz, 2H), 7.24 (d, J=1.7 Hz, 1H).

3-Iodo-hex-2(Z)-en-1-ol (Compound 15)

Employing the procedure used for the preparation of 3-iodo-pent-2(Z)-en-(Compound 1), ethyl-hex-2-ynoate was converted to 3-iodo-hex-2(Z)-en-1-ol.

$^1$H NMR (300 MHz, CDCl$_3$): δ 1.10 (t, J=7.3 Hz, 3H), 2.55 (q, J=7.3 Hz, 2H), 4.21 (d, J=5.5 Hz, 2H), 5.84 (t, J=5.5 Hz, 1H).

1-tert-Butyl-4,4-dimethyl-3,4-dihydro-naphthalen-7-boronic acid (Compound 17)

Employing the procedure used for the preparation of 3,5-diisopropylphenylboronic acid (Compound 2), 1-tert-butyl-4,4-dimethyl-3,4-dihydro-7-bromonaphthalene (Compound 16) was converted to the title compound. The resulting crude product was used in the next step without further purification. 1-tert-butyl-4,4-dimethyl-3,4-dihydro-7-bromonaphthalene (Compound 16) can be obtained in accordance with the disclosure of U.S. Pat. No. 5,741,896, incorporated herein by reference.

3-(1-tert-Butyl-4,4-dimethyl-3,4-dihydro-naphthalen-7-yl)-hex-2(Z)-en-1-ol (Compound 18)

Employing the procedure used for the preparation of 3-(3,5-di-tert-butylphenyl)-hex-2(Z)-en-1-ol (Compound 10), 1-tert-butyl-4,4-dimethyl-3,4-dihydro-naphthalen-7-boronic acid (Compound 17) was converted into the title compound.

$^1$HNMR (CDCl$_3$): δ 0.88 (t, J=8.0 Hz, 3H), 1.21 (s, 6H), 1.33 (s, 9H), 1.39 (m, 2H), 2.14 (d, J=5.0 Hz, 2H), 2.36 (t, J=6.8 Hz, 2H), 4.11 (t, J=6.6 Hz, 2H), 5.66 (t, J=6.6 Hz, 1H), 5.95 (t, J=5.0 Hz, 1H), 6.93 (dd, J=1.8, 7.9 Hz, 1H), 7.25 (d, J=7.9 Hz, 1H), 7.39 (d, J=1.8 Hz, 1H).

(−) 2(R),3(S)-Methano-3-(1-tert-butyl-4,4-dimethyl-3,4-dihydro-naphthalen-7-yl)-hexan-1-ol (Compound 19)

Employing the procedure used for the preparation of (−)-2(R),3(S)-methano-3-(3,5-diisopropylphenyl)-pentan-1-ol (Compound 4), 3-(1-tert-butyl-4,4-dimethyl-3,4-dihydro-naphthalen-7-yl)-hex-2(Z)-en-1-ol (Compound 18) was converted into the title compound.

Optical Rotation $[\alpha]^{20°}{}^{C}{}_{D}=-26.25°$, solvent is dichloromethane, c=0.0045 g/mL, 1=1;

$^1$HNMR (CDCl$_3$): δ 0.82 (t, J=7.0 Hz, 3H), 0.77–0.84 (m, 2H), 1.19 (s, 6H), 1.34 (s, 9H), 1.18–1.38 (m, 4H), 1.84–1.95 (m, 1H), 2.11 (d, J=7.0 Hz, 2H), 3.28 (brq, 2H), 5.93 (t, J=7.0 Hz, 1H), 7.06 (dd, J=1.8, 8.0 Hz, 1H), 7.20 (d, J=8.0 Hz, 1H), 7.53 (d, J=1.8 Hz, 1H).

2(R),3(S)-Methano-3-(1-tert-butyl-4,4-dimethyl-3,4-dihydro-naphthalen-7-yl)-hexanal (Compound 20)

By employing the procedure used for the preparation of (−)-2(R),3(S)-methano-3-(3,5-diisopropylphenyl)-pentanal (Compound 5), (−) 2(R),3(S)-methano-3-(1-tert-butyl-4,4-dimethyl-3,4-dihydro-naphthalen-7-yl)-hexan-1-ol (Compound 19) was converted into the title compound.

Ethyl-6(S),7(S)-methano-3-(1-tert-butyl-4,4-dimethyl-3,4-dihydro-naphthalen-7-yl)-deca-2(E),4(E)-dienoate (Compound 21)

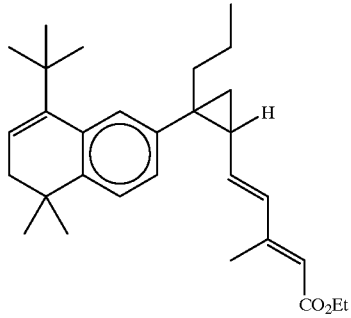

Employing the procedure used for the preparation of ethyl-7-[3,5-diisopropylphenyl]-6(S),7(S)-methano-3-methyl-2(E),4(E)-nonadienoate (Compound 6), 2(R),3(S)-methano-3-(1-tert-butyl-4,4-dimethyl-3,4-dihydro-naphthalen-7-yl)-hexanal 20 was converted into the title compound.

$^1$HNMR (CDCl$_3$): δ 0.84 (t, J=6.9 Hz, 3H), 1.06 (t, J=5.0 Hz, 1H), 1.17 (s, 3H), 1.21 (s, 3H), 1.27 (t, J=7.1 Hz, 3H), 1.29 (s, 9H), 1.24–1.39 (m, 4H), 1.62–1.78 (m, 2H), 1.94 (d, J=1.2 Hz, 3H), 2.04 (s, 3H), 2.05–2.15 (m, 2H), 4.15 (q, J=7.1 Hz, 2H), 5.23 (dd, J=10.0, 15.5 Hz, 1H), 5.60 (s, 1H), 5.91 (t, J=5.0 Hz, 1H), 6.18 (d, J=15.5 Hz, 1H), 7.00 (dd, J=1.8, 8.1 Hz, 1H), 7.21 (d, J=8.1 Hz, 1H), 7.45 (d, J=1.8 Hz, 1H).

(+) 6(S),7(S)-Methano-3-(1-tert-butyl-4,4-dimethyl-3,4-dihydro-naphthalen-7-yl)-deca-2(E)4(E)-dienoic acid (Compound 22)

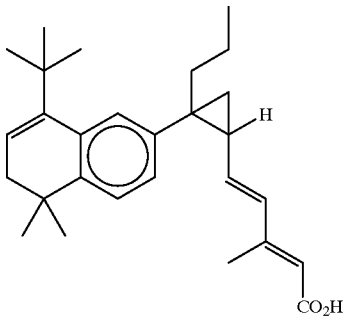

Employing the procedure used for the preparation of (+) 7-[3,5-diisopropylphenyl]-6(S),7(S)-methano-3-methyl-2(E),4(E)-nonadienoic acid Compound 7, ethyl-6(S),7(S)-methano-3-(1-tert-butyl-4,4-dimethyl-3,4-dihydro-naphthalen-7-yl)-deca-2(E),4(E)-dienoate 21, was converted into the title compound.

Optical Rotation $[\alpha]^{20°}{}^{C}{}_{D}$=+14.2°, solvent is dichloromethane;

$^1$HNMR (CDCl$_3$): δ 0.86 (t, J=6.9 Hz, 3H), 1.10 (t, J=4.4 Hz, 1H), 1.18 (s, 3H), 1.23 (s, 3H), 1.21–1.40 (m, 4H), 1.30 (s, 9H), 1.70–1.81 (m, 2H), 1.96 (s, 3H), 2.11–2.15 (m, 2H), 5.30 (dd, J=10.0, 15.5 Hz, 1H), 5.65 (s, 1H), 5.93 (t, J=4.8 Hz, 1H), 6.23 (d, J=15.5 Hz, 1H), 7.03 (dd, J=1.5, 7.8 Hz, 1H), 7.44 (d, J=1.5 Hz, 1H).

7-Bromo-2,2-4-trimethyl-2H-chromene (Compound 23)

A 3.0 M solution of MeMgBr in ether (14 mL, 42.9 mmol) was added slowly to a solution of cerium chloride (10.6 g, 42.9 mmol) in 30 mL of anhydrous THF at 0° C. The mixture was stirred for 2 hours at room temperature. The mixture was cooled to 0° C. and a solution of 7-bromo-2,2-dimethyl-chroman-4-one (available in accordance with J. Med. Chem. 33 1990, 3028–3034, incorporated herein by reference) in THF (20 mL) was added. The reaction mixture was stirred for 20 hours at room temperature. The reaction was quenched with 1% H$_2$SO$_4$, at 0° C. and extracted with ether (3×50 mL). The organic layer was washed with water (2×100 mL) and brine (2×100 mL), dried with MgSO$_4$ and the solvent was removed by distillation. The residue was then refluxed with 20 mL of 20% H$_2$SO$_4$ for 14 hours. The reaction mixture was extracted with ether (3×20 mL), the organic layer was washed with water, brine, dried and the solvent was removed by distillation. The title compound was isolated as an oil after chromatography.

$^1$HNMR (CDCl$_3$): δ 1.38 (s, 6H), 1.97 (d, J=1.5 Hz, 3H), 5.41 (d, J=1.5 Hz, 1H), 6.94–6.99 (m, 3H).

3-(2,2-4-Trimethyl-2H-chromen-7-yl)-but-2(Z)-en-1-ol (Compound 24)

Employing the procedure used for the preparation of 3-(3,5-di-tert-butylphenyl)-hex-2(Z)-en-1-ol (Compound 10), 7-bromo-2,2-4-trimethyl-2H-chromene (Compound 23) was converted into the title compound.

$^1$HNMR (CDCl$_3$): δ 1.38 (s, 6H), 1.97 (s, 3H), 2.05 (s, 3H), 4.11 (t, J=4.5 Hz, 2H), 5.48 (s, 1H), 5.67 (t, J=4.5 Hz, 1H), 6.50 (s, 1H), 6.58 (d, J=7.8 Hz, 1H), 7.09 (d, J=7.8 Hz, 1H).

2(R),3(S)-Methano-3-(2,2-4-trimethyl-2H-chromen-7-yl)-butan-1-ol (Compound 25)

Employing the procedure used for the preparation of (−)-2(R),3(S)-methano-3-(3,5-diisopropylphenyl)-pentan-1-ol (Compound 4), 3-(2,2-4-trimethyl-2H-chromen-7-yl)-but-2(Z)-en-1-ol (Compound 24) was converted into the title compound.

$^1$HNMR (CDCl$_3$): δ 0.73 (dd, J=4.9, 8.4 Hz, 1H), 0.87 (t, J=5.1 Hz, 1H), 1.37 (s, 6H), 1.38 (s, 3H), 1.97 (d, J=1.6 Hz, 1H), 3.15–3.34 (m, 2H), 5.35 (s, 1H), 6.73 (d, J=1.8 Hz, 1H), 6.82 (dd, J=1.8, 7.8 Hz, 1H), 7.05 (d, J=7.8 Hz, 1H).

2(R),3(S)-Methano-3-(2,2-4-trimethyl-2H-chromen-7-yl)-butanal (Compound 26)

By employing the procedure used for the preparation of (−)-2(R),3(S)-methano-3-(3,5-diisopropylphenyl)-pentanal (Compound 5), 2(R),3(S)-methano-3-(2,2-4-trimethyl-2H-chromen-7-yl)-butan-1-ol (Compound 25) was converted into the title compound.

$^1$HNMR (CDCl$_3$): δ 1.36 (s, 3H), 1.38 (s, 3H), 1.43 (s, 3H), 1.75–1.93 (m, 3H), 1.95 (d, J=1.5 Hz, 3H), 5.37 (d, J=1.5 Hz, 1H), 6.74 (d, J=1.8 Hz, 1H), 6.80 (dd, J=1.8, 7.8 Hz, 1H), 7.04 (d, J=7.8 Hz, 1H), 8.42 (d, J=6.8 Hz, 1H).

Ethyl-6(S),7(S)-methano-3-(2,2-4-trimethyl-2H-chromen-7-yl)-octa-2(E),4(E)-dienoate (Compound 27)

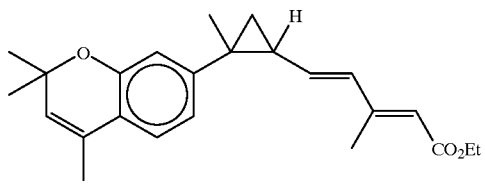

Employing the procedure used for the preparation of ethyl-7-[3,5-diisopropylphenyl]-6(S),7(S)-methano-3-methyl-2(E),4(E)-nonadienoate (Compound 6), 2(R),3(S)-methano-3-(2,2-4-trimethyl-2H-chromen-7-yl)-butanal (Compound 26) was converted into the title compound.

$^1$HNMR (CDCl$_3$): δ 1.14–1.17 (m, 2H), 1.26 (t, J=7.0 Hz, 3H), 1.35 (s, 3H), 1.40 (s, 3H), 1.41 (s, 3H), 1.68–1.78 (m, 1H), 1.99 (brs, 6H), 4.10 (q, J=7.0 Hz, 2H), 5.23 (dd, J=11.0, 15.5 Hz, 1H), 5.38 (d, J=2.0 Hz, 1H), 5.62 (s, 1H), 6.18 (d, J=15.5 Hz, 1H), 6.70 (d, J=1.8 Hz, 1H), 6.76 (dd, J=1.8, 7.8 Hz, 1H), 7.05 (d, J=7.8 Hz, 1H).

6(S),7(S)-Methano-3-(2,2-4trimethyl-2H-chromen-7-yl)-octa-2(E),4(E)-dienoic acid 28

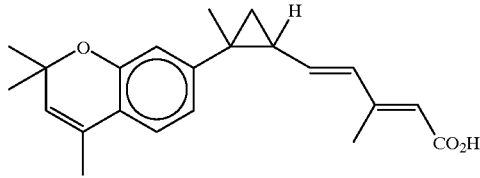

Employing the procedure used for the preparation of (+) 7-[3,5-diisopropylphenyl]-6(S),7(S)-methano-3-methyl-2(E),4(E)-nonadienoic acid (Compound 7), ethyl-6(S),7(S)-methano-3-(2,2-4-trimethyl-2H-chromen-7-yl)-octa-2(E),4(E)-dienoate (Compound 27), was converted into the title compound.

¹HNMR (CDCl₃): δ 1.12 (brs, 1H), 1.14 (brs, 1H), 1.33 (s, 3H), 1.39 (s, 6H), 1.65–1.74 (m, 1H), 1.97 (s, 6H), 5.24 (dd, J=11.0, 15.5 Hz, 1H), 5.36 (s, 1H), 5.62 (s, 1H), 6.18 (d, J=15.5 Hz, 1H), 6.68 (s, 1 H), 6.73 (dd, J=1.5, 8.0 Hz, 1H), 7.03 (d, J=8.0 Hz, 1H).

4,4-Dimethyl-1-isopropyl-7-bromo-3,4-dihydronaphthalene (Compound 29)

Employing the procedure used for the preparation of 7-bromo-2,2-4-trimethyl-2H-chromene (Compound 23), 4,4-dimethyl-7-bromo-3,4-dihydro-2(H)-naphalen-1-one was converted into the title compound.

¹HNMR (CDCl₃): δ 1.15 (d, J=6.7 Hz, 6H), 1.21 (s, 6H), 2.17 (d, J=4.6 Hz, 2H), 2.89 (sept, J=6.7 Hz, 1H), 5.82 (t, J=4.6 Hz, 1H), 7.17 (d, J=8.3 Hz, 1H), 7.30 (dd, J=2.1, 8.3 Hz, 1H), 7.43 (d, J=2.1 Hz, 1H).

3-(1-iso-Propyl-4,4-dimethyl-3,4-dihydro-naphthalen-7-yl)-hex-2(Z)-en-1-ol (Compound 30)

Employing the procedure used for the preparation of 3-(3,5-di-tert-butylphenyl)-hex-2(Z)-en-1-ol (Compound 10), 4,4-dimethyl-1-iso-propyl-7-bromo-3,4-dihydronaphthalene (Compound 29) was converted into the title compound.

¹HNMR (CDCl₃): δ 0.88 (t, J=7.5 Hz, 3H), 1.15 (d, J=6.9 Hz, 6H), 1.23 (s, 6H), 1.31–1.45 (m, 2H), 2.17 (d, J=4.4 Hz, 2H), 2.35 (t, J=6.9 Hz, 2H), 2.92 (sept, J=6.9 Hz, 1H), 4.08 (t, J=6.0 Hz, 2H), 5.66 (t, J=6.0 Hz, 1H), 5.78 (t, J=4.4 Hz, 1H), 6.95 (dd, J=1.7, 7.8 Hz, 1H), 7.06 (d, J=1.7 Hz, 1H), 7.26 (d, J=7.8 Hz, 1H).

(−) 2(R),3(S)-Methano-3-(1-iso-propyl-4,4-dimethyl-3,4-dihydro-naphthalen-7-yl)-hexan-1-ol (Compound 31)

Employing the procedure used for the preparation of (−)-2(R),3(S)-methano-3-(3,5-diisopropylphenyl)-pentan-1-ol (Compound 4), 3-(1-iso-propyl-4,4-dimethyl-3,4-dihydro-naphthalen-7-yl)-hex-2(Z)-en-1-ol (Compound 30) was converted into the title compound.

Optical Rotation $[\alpha]^{20°}{}^{C\cdot}{}_{D}$=−26.67°, solvent is dichloromethane;

¹HNMR (CDCl₃): δ 0.75–0.85 (m, 5H), 1.12–1.34 (m, 13H), 1.85–1.94 (m, 1H), 2.15 (d, J=4.4 Hz, 2H), 2.96 (sept, J=6.9 Hz, 1H), 3.26 (t, J=7.1 Hz, 2H), 5.72 (t, J=4.4 Hz, 1H), 7.09 (dd, J=1.7, 7.9 Hz, 1H), 7.20 (d, J=7.9 Hz, 1H), 7.26 (d, J=1.7 Hz, 1H).

(+) 2(R),3(S)-Methano-3-(1-iso-propyl-4,4-dimethyl-3,4-dihydro-naphthalen-7-yl)-hexanal (Compound 32)

By employing the procedure used for the preparation of (−)-2(R),3(S)-methano-3-(3,5-diisopropylphenyl)-pentanal (Compound 5), (−) 2(R),3(S)-methano-3-(1-iso-propyl-4,4-dimethyl-3,4-dihydro-naphthalen-7-yl)-hexan-1-ol (Compound 31) was converted into the title compound.

Optical Rotation $[\alpha]^{20°}{}^{C\cdot}{}_{D}$=+8.7°, solvent is dichloromethane.

¹HNMR (CDCl₃): δ 0.80–0.90 (m, 5H), 1.15–1.40 (m, 14H), 1.43–1.47 (m, 1H), 1.80–1.95 (m, 3H), 2.17 (d, J=4.4 Hz, 2H), 2.94 (sept. J=6.9 Hz, 1H), 5.78 (t, J=4.4 Hz, 1H), 7.10 (dd, J=1.8, 8.0 Hz, 1H), 7.23 (d, J=8.0 Hz, 1H), 7.27 (brs, 1H), 8.44 (d, J=7.6 Hz, 1H).

Ethyl-6(S),7(S)-methano-3-(1-iso-propyl-4,4-dimethyl-3,4-dihydro-naphthalen-7-yl)-deca-2(E),4(E)-dienoate (Compound 33)

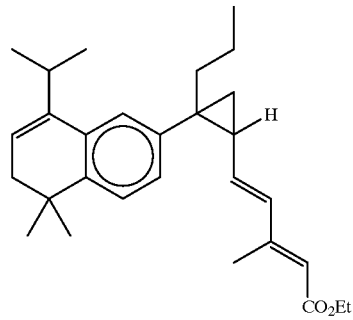

Employing the procedure used for the preparation of ethyl-7-[3,5-diisopropylphenyl]-6(S),7(S)-methano-3-methyl-2(E),4(E)-nonadienoate (Compound 6), 2(R),3(S)-methano-3-(1-iso-propyl-4,4-dimethyl-3,4-dihydro-naphthalen-7-yl)-hexanal (Compound 32) was converted into the title compound.

Optical Rotation $[\alpha]^{20°}{}^{C\cdot}{}_{D}$=+96.30°, solvent is dichloromethane.

¹HNMR (CDCl₃): δ 0.84 (t, J=6.9 Hz, 3H), 1.08 (d, J=6.9 Hz, 3H), 1.15 (d, J=6.9 Hz, 3H), 1.09 (s, 3H), 1.18–1.32 (m, 5H), 1.25 (s, 3H), 1.27 (t, J=7.2 Hz, 3H), 1.70–1.82 (m, 2H), 1.95 (s, 3H), 2.15 (t, J=4.4 Hz, 2H), 2.90 (sept. J=6.9 Hz, 1H), 4.14 (q, J=7.2 Hz, 2H), 5.21 (dd, J=11.0, 15.5 Hz, 1H), 5.61 (s, 1H), 5.74 (t, J=4.4 Hz, 1H), 6.17 (d, J=15.5 Hz, 1H), 7.00 (dd, J=1.8, 7.9 Hz, 1H), 7.16 (d, J=1.8 Hz, 1H), 7.19 (d, J=7.9 Hz, 1H).

(+) 6(S),7(S)-Methano-3-(1-iso-propyl-4,4-dimethyl-3,4-dihydro-naphthalen-7-yl)-deca-2(E),4(E)-dienoic acid (Compound 34)

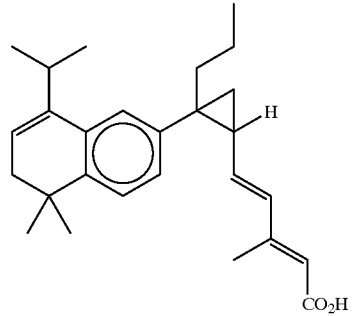

Employing the procedure used for the preparation of (+) 7-[3,5-diisopropylphenyl]-6(S),7(S)-methano-3-methyl-2(E),4(E)-nonadienoic acid (Compound 7), (+) ethyl-6(S),7(S)-methano-3-(1-iso-propyl-4,4-dimethyl-3,4-dihydro-naphthalen-7-yl)-deca-2(E),4(E)-dienoate (Compound 33), was converted into the title compound.

Optical Rotation $[\alpha]^{20°}{}^{C\cdot}{}_{D}$=+46.24°, solvent is dichloromethane;

¹HNMR (CDCl₃): δ 0.84 (t, J=6.9 Hz, 3H), 1.08 (d, J=6.9 Hz, 3H), 1.15 (d, J=6.9 Hz, 3H), 1.09 (s, 3H), 1.18–1.32 (m, 5H), 1.25 (s, 3H), 1.70–1.82 (m, 2H), 1.95 (s, 3H), 2.15 (t, J=4.4 Hz, 2H), 2.90 (sept. J=6.9 Hz, 1H), 4.14 (q, J=7.2 Hz, 2H), 5.21 (dd, J=11.0, 15.5 Hz, 1H), 5.61 (s, 1H), 5.74 (t, J=4.4 Hz, 1H), 6.17 (d, J=15.5 Hz, 1H), 7.00 (dd, J=1.8, 7.9 Hz, 1H), 7.16 (d, J=1.8 Hz, 1H), 7.19 (d, J=7.9 Hz, 1H).

3-Iodo-O-triisopropylsilyl-but-2(Z)-ene-ol (Compound 36)

A stirred, cooled (ice bath) solution of 3-iodo-but-2(z)-ene-ol (Compound 35, 1.0 g, 5 mmol) in 10 mL of anhydrous dichloromethane was treated sequentially with 2,6-lutidine (0.88 mL, 7.5 mmol) and tri-iso-propylsilyltrifluoromethanesulfonate (1.36 mL, 5 mmol) under argon. (Compound 35 is obtainable in analogy to the synthesis of 3-iodo-pent-2(Z)-en-1-ol (Compound 1)). After stirring at room temperature for 1 hour, the reaction mixture was diluted with 10 mL of hexane and purified by flash column chromatography over silica gel (230–400 mesh) using 2.5% ethyl acetate in hexane as the eluent to afford the title compound as a colorless oil (1.62 g, 91%).

$^1$H-NMR (300 MHz, CDCl$_3$): d 1.05–1.15 (m, 21H), 2.51 (d, J=1.5 Hz, 3H), 4.25 (dd, J=3.6, 5.2 Hz, 2H), 5.73 (dt, J=1.7, 5.0 Hz, 1H).

4-(1-Adamantyl)phenyltrifluoromethanesulfonate (Compound 37)

A stirred, cooled (0° C.) solution of 4-(1-adamantyl) phenol (3.2 g, 14 mmol, obtainable in accordance with the chemical literature) and triethylamine (3.3 mL, 22.4 mmol) in 40 mL of anhydrous dichloromethane was treated with 2-[N,N-bis(trifluoromethanesulfonyl)amino]-5-chloropyridine (5.6 g, 14.2 mmol). The resulting solution was warmed to room temperature over 0.5 hour, then diluted with 20 mL of dichloromethane and washed with 30 mL of 3M HCl followed by 30 mL of brine. The organic phase was dried over anhydrous sodium sulfate and evaporated in vacuo to yield an orange solid which on flash column chromatography over silica gel (230–400 mesh) using 5% ethyl acetate in hexane as the eluent afforded the title compound as a white solid (3.72 g, 73%).

$^1$H-NMR (300 MHz, CDCl$_3$): d 1.78 (dd, J=10.0, 19.9 Hz, 6H), 1.91 (d, J=2.4 Hz, 6H), 2.12 (s, 3H), 7.21 (dd, J=2.3, 8.9 Hz, 2H), 7.43 (dd, J=8.9, 2.2 Hz, 2H).

3-(4-Adamantan-1-yl-phenyl)-1-O-triisopropylsilyl-but-2(Z)-ene-ol (Compound 38)

3-iodo-O-triisopropylsilyl-but-2(Z)-ene-ol (Compound 36, 1.22 g, 3.44 mmol)) was converted to O-triisopropylsilyl-but-2(Z)-ene-ol-3-boronic acid in analogy to the preparation of boronic acid derivatives described above, and was used without any purification. Its proton nmr spectrum revealed that there was a considerable amount (~60%) of rearranged product and that the desired product was formed in a small amount. A solution of a mixture of the crude boronic acid derivative, 4-(1-adamantyl) phenyltrifluoromethanesulfonate (Compound 37, 0.36 g, 1 mmol), lithium chloride (0.29 g, 7 mmol), sodium carbonate (0.42 g, 4 mmol) and tetrakis(triphenylphosphine)palladium (0) (0.078 g) in a combination of 2 mL of water, 5 mL of methanol and 10 mL of toluene was degassed with argon for 10 minutes and refluxed under argon for 24 hours. The volatile solvents were removed by evaporation in vacuo and the residue was diluted with 20 mL of water and extracted with diethyl ether (2×25 mL). The combined organic extracts were dried over anhydrous sodium sulfate and the solvent was evaporated to provide a yellow residual oil which on flash column chromatography on silica gel (230–400 mesh) using 3% ethyl acetate in hexane as the eluent afforded the title compound (0.275 g, 62 yield % based on Compound 37) as a yellow oil.

$^1$H-NMR (300 MHz, CDCl$_3$): d 1.02–1.13 (m, 21H), 1.75–1.82 (m, 6H), 1.91–1.93 (m, 6H), 2.08 (s, 6H), 4.18 (d, J 5.5 Hz, 2H), 5.66 (unresolved t, 1H), 7.14 (d, J=8.0 Hz, 2H), 7.31 (d, J=8.2 Hz, 1H).

3-(4-Adamantan-1yl-phenyl)-but-2(Z)-ene-ol (Compound 39)

3-(4-Adamantan-1-yl-phenyl)-1-O-triisopropylsilyl-but-2(Z)-ene-ol (Compound 38, 0.27 g, 0.62 mmol) was dissolved in 10 mL of 1:1 methanol tetrahydrofuran and treated with 3 mL of 1 N HCl. After stirring at room temperature for 0.5 hours, the volatile solvents were removed by evaporation in vacuo and the residue was diluted with water (15 mL) and extracted with diethyl ether (2×20 mL). The combined organic extracts were dried over anhydrous sodium sulfate and evaporated in vacuo to provide a residual oil. Flash column chromatography on silica gel (230–400 mesh) using 20% ethyl acetate in hexane as the eluent afforded the title compound (0.082 g, 49%) as an off-white solid.

$^1$H-NMR (300 MHz, CDCl$_3$): d 1.59 (s, 1H), 1.74–1.84 (m, 6H), 1.94 (d, J=2.8 Hz, 6H), 2.09–2.12 (m, 6H), 4.10 (d, J=7.0 Hz, 2H), 5.69 (dt, J=1.4, 7.0 Hz, 1H), 7.14 (dd, J=8.3, 2.0 Hz, 2H), 7.34 (dd, J=8.3, 2.0 Hz, 1H).

3-[4-(1-Adamantan-1-yl-phenyl)]-2,3-methano-butylalcohol (Compound 40)

3-(4-adamantan-1yl-phenyl)-but-2(Z)-ene-ol (Compound 39, 0.32 g, 1.2 mmol) was converted into the title compound (viscous oil, 0.32 g, 94%), enriched in the 2S,3S isomer, in analogy to the cyclopropylation reactions described above.

$^1$H-NMR (300 MHz, CDCl$_3$): d 0.78 (dd, J=4.8, 8.4 Hz, 1H), 0.89 (t, J=5.0 Hz, 1H), 1.25–1.38 (m, 1H), 1.40 (s, 3H), 1.72–1.82 (m, 6H), 1.90 (d, J=2.6 Hz, 6H), 2.09 (s, 3H), 3.17–3.26 (m, 1H), 3.28–3.32 (m, 1H), 7.24–7.31 (m, 4H).

(1S)-Camphanate ester of (2S,3S)-3-[4-(1-adamantan-1-yl-phenyl)-2,3-methano-butylalcohol (Compound 41)

3-[4-(1-Adamantan-1-yl-phenyl)]-2,3-methano-butylalcohol (enriched in the 2S,3S isomer (Compound 40, 0.32 g, 1.1 mmol) was converted to the title compound with (1S)-camphanic chloride, in anhydrous dichloromethane, in the presence of triethylamine by stirring overnight at room temperature under a protective argon blanket. The product obtained by evaporation of the solvents and extraction of the residue was recrystallized from hot 1:1 ethyl acetate: hexane (0.35 g, 65%).

$^1$H-NMR (300 MHz, CDCl$_3$): d 0.87 (dd, J=5.0, 8.4 Hz, 1H), 0.93–0.99 (m, 1H), 0.95 (s, 3H), 1.04 (s, 3H), 1.12 (s, 3H), 1.30–1.41 (m, 1H), 1.39 (s, 3H), 1.65–1.82 (m, 7H), 1.85–2.10 (m, 2H), 1.89 (d, J=2.44 Hz, 6H), 2.09 (s, 3H), 2.33–2.42 (m, 1H), 3.77 (dd, J=7.5, 11.5 Hz, 1H), 3.91 (dd, J=7.6, 11.5 Hz, 1H), 7.21–7.29 (m, 4H).

(2S,3S)-3-[4-(1-Adamantan-1-yl-phenyl)]-2,3-methano-butylalcohol (Compound 40)

(1S)-Camphanate ester of (2S,3S)-3-[4-(1-adamantan-1-yl-phenyl)]-2,3-methano-butylalcohol (Compound 41, 0.35 g, 0.75 mmol) was converted into the optically pure title compound by saponification of the ester with lithium hydroxide in a mixture of methanol and tetrahydrofuran, followed by evaporation of the volatile solvents, extraction of the residue with diethyl ether, washing, drying (MgSO$_4$) and evaporation of solvents to give the product as a viscous oil (0.2 g, 94%).

¹H-NMR (300 MHz, CDCl₃): d 0.78 (dd, J=4.8, 8.4 Hz, 1H), 0.89 (t, J=5.0 Hz, 1H), 1.25–1.38 (m, 1H), 1.40 (s, 3H), 1.72–1.82 (m, 6H), 1.90 (d, J=2.6 Hz, 6H), 2.09 (s, 3H), 3.17–3.26 (m, 1H), 3.28–3.32 (m, 1H), 7.24–7.31 (m, 4H).

(2S,3S)-3-[4-(1-Adamantan-1-yl-phenyl]-2,3-methano-1-oxo-butane (Compound 42)

(2S,3S)-3-[4-(1-Adamantan-1-yl-phenyl)]-2,3-methano-butylalcohol (Compound 40, 0.2 g, 0.7 mmol) was converted to the title compound (0.19 g, 97%) in analogy to the oxidation reactions described above.

¹H-NMR (300 MHz, CDCl₃): d 1.41 (dd, J 4.8,7.6 Hz, 1H), 1.46 (s, 3H), 1.68–1.84 (m, 7H), 1.8501.98 (m, 7H), 2.09 (s, 3H), 7.28 (ABq, J=12 Hz, 4H), 8.41 (d, J=7.1 Hz, 1H).

(6S,7S)-7-[4-(Admantan-1-yl-phenyl)]-6,7-methano-3-methyl-octa-2E,4E-dienoic acid ethyl ester (Compound 43)

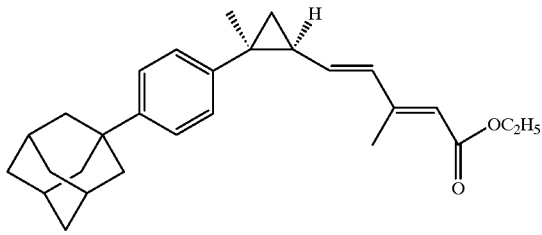

(2S,3S)-3-[4-(1-Adamantan-1-yl-phenyl)]-2,3-methano-1-oxo-butane (Compound 42, 0.19 g, 0.68 mmol) was converted to the title compound (0.25 g, 91%) in analogy to the Horner Emmons reactions described above.

¹H-NMR (300 MHz, CDCl₃): d 1.16–1.19 (m, 2H), 1.27 (t, J=7.1 Hz, 3H), 1.42 (s, 3H), 1.68–1.84 (m, 8H), 1.91 (d, J=2.8 Hz, 6H), 1.96 (s, 3H), 2.09 (s, 3H), 4.14 (q, J=7.1 Hz, 2H), 5.11 (dd, J=10.0, 15.4 Hz, 1H), 5.62 (s, 1H), 6.17 (d, J=15.5 Hz, 1H), 7.19 (dd, J=2.0, 8.4 Hz, 2H), 7.27 (dd, J=1.9, 8.4 Hz, 2H).

(6S,7S)-7-[4-(Adamantan-1-yl-phenyl)]-6,7-methano-3-methyl-octa-2E,4E-dienoic acid (Compound 44)

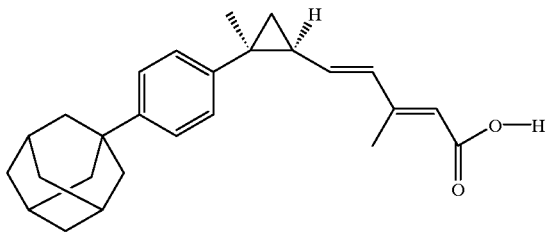

(6S,7S)-7-[4-(Adamantan-1-yl-phenyl)]-6,7-methano-3-methyl-octa-2E,4E-dienoic acid ethyl ester (Compound 43, 0.18 g, 0.44 mmol) was converted to the title compound by saponification as described above (0.038 g, 22%) after recrystallization from hot 1:7 isopropanol:hexane).

¹H-NMR (300 MHz, CDCl₃): d 1.20 (d, J=7.0 Hz, 2H), 1.44 (s, 3H), 1.68–1.84 (m, 8H), 1.91 (d, J=2.48 Hz, 6H), 1.97 (s, 3H), 2.10 (s, 3H), 5.23 (dd, J=10.1, 15.5 Hz, 1H), 5.64 (s, 1H), 6.44 (d, J=15.6 Hz, 1H), 7.19 (dd, J=2.0, 8.4 Hz, 2H), 7.29 (dd, J=2.0, 8.4 Hz, 2H).

1-t-Butyl-1-hydroxy 4,4-dimethyl-7-bromo-1,2,3,4-tetrahydronaphthalene

To a cold (−30° C.) solution of 4,4-dimethyl-7-bromo-3,4-dihydronaphthalen-2(H)-1-one (5 g, 19.8 mmol), 1,3-dimethyl-3,4,5,6-tetrahydro-2(1H)-pyrimidinone DMPU (17 mL), THF (50 mL) was added t-BuMgCl (1M solution in THF, 81 mL), then cooling was removed and the reaction mixture was stirred at ambient temperature for 20 h. The reaction mixture was cooled to −78° C. and water (20 mL), saturated NH₄Cl (20 mL) and 10% HCl (20 mL) were added sequentially. The mixture was warmed to ambient temperature, diluted with EtOAc (300 mL), washed with brine, dried and the solvent was dried (MgSO₄) and removed by evaporation to yield 6 g of crude material comprising a mixture of product and starting material. The crude material was used in the next step without purification.

1-t-butyl-4,4-dimethyl-7-bromo-3,4-dihydronaphthalene (Compound 16)

A mixture of the crude 1-t-butyl-1-hydroxy 4,4-dimethyl-7-bromo-1,2,3,4-tetrahydronaphthalene , MeOH (30 mL) and p-TSA (150 mg) were heated for 17 h at 70° C. Reaction mixture was cooled to ambient temperature and solid K₂CO₃ was added and the MeOH was removed by evaporation. The residue was diluted with ether. The ether layer was washed with water and brine and the ether was dried (MgSO₄) and removed by evaporation. Purification by silica gel chromatography yielded 1.65 g (28%, in two steps) the title compound as a clear oil.

¹H NMR (300 MHz, CDCl₃) δ 1.20 (s, 6H), 1.33 (s, 9H), 2.13 (d, 2H, J=5.0 Hz), 5.98 (t, 1H, J=4.9 Hz), 7.16 (d, 1H, J=7.8 Hz), 7.28 (d, 1H, J=7.9 Hz), 7.75 (s, 1H).

3-(1-t-Butyl-4,4-dimethyl-3,4-dihydronaphthalen-7-yl)-but-2(Z)-en-1-ol (Compound 51)

To a cold (−78° C.) solution of 1-t-butyl-4,4-dimethyl-7-bromo-3,4-dihydronaphthalene (Compound 16, 934 mgs, 3.4 mmol) in THF (30 mL) was added t-BuLi (2.03 equivalent) drop-wise. The mixture was stirred for 1 hour and B(OMe)₃ (2.03 equivalent) was added drop-wise. The mixture was warmed gradually (over 2 hours) to room temperature and stirred at ambient temperature for 15 min. NH₄Cl (20 mL) was added to the reaction mixture and the mixture was stirred for 10 min. The mixture was diluted with 150 mL EtOAc and the organic layer was washed with 10% HCl, water and brine. The solvent was dried (MgSO₄) and removed by evaporation to yield 769 mg crude product, which was used in the next step without further purification.

Argon gas was bubbled for 6 minutes into a solution of the crude borate (0.769 g), 3-iodo-but-2-(Z)en-1-ol (0.67 g), K₂CO₃ (3.8 g) in water (10 mL), MeOH (4 mL) and toluene (40 mL). Then Pd(PPh₃)₄ (70 mg) was added and argon gas was bubbled into the mixture for another 2 min. Then the mixture was heated at 95° C. for 12 hours under argon. The mixture was then cooled to ambient temperature and diluted with ether. The organic layer was washed with water and brine. The solvent was dried (MgSO₄) and removed by evaporation. The crude product was purified by silica gel column chromatography to yield 441 mg (46%, in two steps) of the title compound.

¹H NMR (300 MHz, CDCl₃) δ 1.22 (S, 6H), 1.35 (S, 9H), 2.08 (S, 3H), 2.13 (d, 2H, J=5.0 Hz), 4.12 (m, 2H), 5.67 (m, 1H), 5.96 (t, 1H, J=4.9 Hz), 6.98 (d, 1H, J=7.8 Hz), 7.26 (d, 1H, J=7.8 Hz), 7.44 (s, 1H).

3-(1-t-Butyl-4,4-dimethyl-3,4-dihydronaphthalen-7-yl)-(2R,3S)-2,3-methano-butan-1-ol (Compound 52)

1). Preparation of Et₂Zn in CH₂Cl₂ solution: cannulate about 10 ml Et₂Zn (neat) into an anhydrous CH₂Cl₂ (100 mL sealed bottle, pre-weighed). The bottle was weighed after the addition of Et₂Zn and molarity calculated (0.82M).

2). (CH₂I)₂Zn DME Preparation: To a dried flask under argon was added Et₂Zn in CH₂Cl₂ (0.82M, 38 mL). The solution was cooled to −10° C. and dimethoxyethane DME (3.2 mL) was added. The resulting mixture was cooled to −20° C. then CH₂I₂ (2.5 mL) was added via a syringe pump over 25 min.

3). Into another flask containing 3-(1-t-butyl-4,4-dimethyl-3,4-dihydronaphthalen-7-yl)-but-2(Z)-en-1-ol (Compound 51, 441 mg, 1.5 mmol) were added under argon mol. sieves (1.5 g), D(−)borolidine-tartaramide (839 mg, 3.1 mmol) followed by anhydrous CH₂Cl₂ (15 mL). The mixture was cooled to −78° C. and into this mixture (−20° C.) (CH₂I)₂Zn DME solution was cannulated. The mixture was stirred at −25° C. for 18 h then at −5° C. for 4 h. For work-up the reaction was quenched by adding NH₄Cl (sat.) and the mixture was extracted with ether (3×50 mL). The combined organic layers were washed with water and brine. The solvent was dried (MgSO₄) and removed by evaporation Purification by column chromatography gave 422 mg (91%) clear oil.

¹H NMR (300 MHz, CDCl₃) δ 0.75–0.82 (m, 1H), 0.83–0.90 (m, 1H), 1.20 (s, 6H), 1.2–1.3 (m, 1H), 1.35 (s, 9H), 1.40 (s, 3H), 2.11 (d, 2H, J=5.0 Hz), 3.28 (m, 2H), 5.94 (t, 1H, J=4.9 Hz), 7.11 (d, 1H, J=7.8 Hz), 7.22 (d, 1H, J=7.8 Hz), 7.59 (s, 1H).

4,7,7-Trimethyl-3-oxo-2-oxa-bicyclo[2,2,1]heptane-1-carboxylic acid 3-(1-t-butyl-4,4-dimethyl-3,4-dihydronaphthalen-7-yl)-(2R,3S)-2,3-methano-butylester (Compound 53) and its diastereomer A mixture of 3-(1-t-butyl-4,4-dimethyl-3,4-dihydronaphthalen-7-yl)-(2R,3S)-2,3-methano-butan-1-ol (Compound 52, 422 mg, 1.4 mmol), CH₂Cl₂ (8 mL), 1(s)-(s)camphanic chloride (1.2 g), triethylamine (7 mL), and DMAP (50 mg) was heated to 55° C. for 16 h. The reaction mixture was cooled to room temperature, diluted with ether, washed with water, NaHCO₃ (sat.) and brine. The solvent was dried (MgSO₄) and removed by evaporation. Purification by silica gel column chromatography gave 580 mg (87%) white solid. The two diastereomers were isolated by HPLC (normal phase, 6% EtOAc/Hexane) to give desired diastereomer, Compound 53.

¹H NMR (300 MHz, CDCl₃) δ 0.85–0.92 (m, 2H), 0.9–1.0 (m, 1H), 0.94 (s, 3H), 1.02 (s, 3H), 1.11 (s, 3H), 1.18 (s, 3H), 1.19 (s, 3H), 1.35 (s, 9H), 1.40 (s, 3H), 1.6–1.75 (m, 1H), 1.83–2.03 (m, 2H), 2.11 (d, 2H, J=5.0 Hz), 2.3–2.4 (m, 1H), 3.67 (dd, 1H, J=6.7, 11.5 Hz), 4.11 (dd, 1H, J=6.7, 11.5 Hz), 5.94 (t, 1H, J=4.9 Hz), 7.08 (d, 1H, J=7.8 Hz), 7.20 (d, 1H, J=7.8 Hz), 7.54 (s, 1H).

3-(1-t-Butyl-4,4-dimethyl-3,4-dihydronaphthalen-7-yl)-(2R,3S)-2,3-methano-butan-1-ol (Compound 54)

To a solution of camphanic ester (Compound 53, 280 mg) in THF (10 mL), MeOH (7 mL) was added KOH (1M solution in H₂O) (2.1 mL). The mixture was heated at 750 for two hours, cooled to ambient temperature and the THF and MeOH solvents were removed under reduced pressure. The residue was diluted with water and extracted with ether. The combined ether layers were washed with water and brine. The solvent was dried (MgSO₄) and removed by evaporation to give 170 mg (97%) of the title compound.

3-(1-t-Butyl-4,4-dimethyl-3,4-dihydronaphthalen-7-yl)-(2R,3S)-2,3-methano-butanal (Compound 55)

To 3-(1-t-butyl-4,4-dimethyl-3,4-dihydronaphthalen-7-yl)-(2R,3S)-2,3-methano-butan-1-ol (Compound 54, 170 mg) were added mol. sieves (400 mg), NMO (2.0 eq), TPAP (10 mg) followed by CH₂Cl₂ (5 mL) and CH₃CN (0.6 mL). The mixture was stirred at ambient temperature under argon for 2 h. The mixture was purified by column chromatography to yield 150 mg (89%) of the title compound as clear oil.

¹H NMR (300 MHz, CDCl₃) δ 0.88 (m, 1H), 1.19 (s, 6H), 1.34 (s, 9H), 1.48 (s, 3H), 1.8–2.0 (m, 2H), 2.11 (d, 2H, J=5.0 Hz), 5.96 (t, 1H, J=4.9 Hz), 7.12 (d, 1H, J=7.8 Hz), 7.23 (d, 1H, J=7.8 Hz), 7.59 (s, 1H), 8.45 (d, 1H, J=7.2 Hz).

Ethyl 7-[(1-t-butyl-4,4-dimethyl-3,4-dihydronaphthalen-7-yl](6S,7S)-6,7-methano-3,7-dimethyl-hepta-2E,4E-dienooate (Compound 56)

To a solution of diethyl-(E)-3-ethoxycarbonyl-2-methylallylphosphonate (736 mg) in THF (12 mL) at −78° C. was added n-BuLi (1.6M, 1.7 mL) drop-wise. After five minutes, 3-(1-t-butyl-4,4-dimethyl-3,4-dihydronaphthalen-7-yl)-(2R,3S)-2,3-methano-butanal (Compound 55, 150 mg) in THF (2+2 mL) was added dropwise. The reaction was warmed gradually to −10° C. Water was added to the reaction mixture and extracted with ethyl acetate. The combined organic layers were washed with water and brine. The solvent was dried (MgSO₄) and removed by evaporation. Purification by silica gel column chromatography gave 200 mg product including a minor component (approximately 5%) having the cis isomeric structure in the newly formed double bond. The title compound (trans) was obtained by by purification by HPLC (175 mg, 85%).

¹H NMR (300 MHz, CDCl₃) δ 1.18 (s, 3H), 1.23 (s, 3H), 1.24 (t, 3H, J=7.2 Hz), 1.1–1.3 (m, 2H), 1.32 (s, 9H), 1.44 (s, 3H), 1.7–1.8 (m, 1H), 1.96 (s, 3H), 2H, J=5.0 Hz), 4.14 (q, 2H, J=7.2 Hz), 5.24 (dd, 1H, J=10.0, 15.4 Hz), 5.62 (s, 1H), 5.93 (t, 1H, J=4.9 Hz), 6.20 (d, 1H, J=15.7 Hz), 7.07 (d, 1H, J=7.8 Hz), 7.23 (d, 1H, J=7.8 Hz), 7.52 (s, 1H).

7-[(1-t-Butyl-4,4-dimethyl-3,4-dihydronaphthalen-7-yl](6S,7S)-6,7-methano-3,7-dimethyl-hepta-2E, 4E-dienoic acid (Compound 57)

To a solution of ethyl 7 (1-t-butyl-4,4-dimethyl-3,4-dihydronaphthalen-7-yl](6S,7S)-6,7-methano-3,7-dimethyl-hepta-2E,4E-dienooate (Compound 56, 175 mg, 0.43 mmol) in THF (2.7 mL), methanol (5.4 mL) was added NaOH (1M solution, 2.3 mL). The mixture was heated to 75° C. for 15 hours. The solvents THF and methanol were removed under reduced vacuum. The residue was diluted with ethyl acetate, acidified with 10% HCl (pH=2). The organic layer was washed with water and brine. The solvent was dried (MgSO₄) and removed by evaporation. Flash column chromatography gave the title compound as a white solid 130 mg.

¹H NMR (300 MHz, CDCl₃) δ 1.1–1.3 (m, 2H), 1.16 (s, 3H), 1.21 (s, 3H), 1.29 (s, 9H), 1.43 (s, 3H), 1.7–1.8 (m, 1H), 1.94 (s, 3H), 2.12 (d, 2H, J=5.0 Hz), 5.28 (dd, 1H, J=10.2, 15.6 Hz), 5.62 (s, 1H), 5.92 (t, 1H, J=4.9 Hz), 6.22 (d, 1H, J=15.6 Hz), 7.06 (d, 1H, J=7.8 Hz), 7.22 (d, 1H, J=7.8 Hz), 7.50 (s, 1H).

3-(1-Iso-propyl-4,4-dimethyl-3,4-dihydronaphthalen-7-yl)-but-2(Z)-en-1-ol (Compound 58)

To a cold (−78° C.) solution of 4,4-dimethyl-1-isopropyl-7-bromo-3,4-dihydronaphthalene (Compound 29, 902 mg, 3.2 mmol) in THF was added t-BuLi (2.03 eq) dropwise. The mixture was stirred for 1 hour and B(OMe)₃ (2.03 eq) was added drop-wise. The mixture was warmed gradually (over 2 hours) to ambient temperature and stirred at ambient temperature for 15 min. NH$_4$Cl (20 mL) was added to the reaction mixture and the mixture was stirred for 10 min. The mixture was diluted with 150 mL EtOAc and the organic layer was washed with 10% HCl, water and brine (30 mL each). The solvent was dried MgSO$_4$ and removed by evaporation to yield 651 mg crude product, which was used in the next step without further purification.

Argon gas was bubbled for 6 minutes into a solution of the crude borate (0.651 g), 3-iodo-but-2-(Z)en-1-ol (0.53 g), K$_2$CO$_3$ (2.4 g) in water (6.4 mL), MeOH (4 mL) and toluene (40 mL). Then Pd(PPh$_3$)$_4$ (70 mg) was added and argon was bubbled into the solution for another 2 min. Then the mixture was heated at 95° C. for 12 hours under argon. The mixture was then cooled to ambient temperature and diluted with ether. The organic layer was washed with water and brine. The solvent was dried MgSO$_4$ and was removed by evaporation. The crude product was purified by silica gel column chromatography to yield in two steps the title compound 281 mg (33%).

$^1$H NMR (300 MHz, CDCl$_3$) δ 1.16 (d, 6H, J=7.0 Hz), 1.24 (s, 6H), 2.10 (s, 3H), 2.18 (d, 2H, J=4.4 Hz), 2.94 (m, 1H), 4.13 (m, 2H), 5.70 (m, 1H), 5.79 (t, 1H, J=4.6 Hz), 7.01 (d, 1H, J=7.8 Hz), 7.13 (s, 1H), 7.28 (d, 1H, J=8.0 Hz).

3-(1-Isopropyl-4,4-dimethyl-3,4-dihydronaphthalen-7-yl)-(2R,3S)-2,3-methano-butan-1-ol and its enantiomer (Compound 59)

1). Preparation of Et$_2$Zn in CH$_2$Cl$_2$ solution: cannulate about 10 ml Et$_2$Zn (neat) into an anhydrous CH$_2$Cl$_2$ (100 ml sealed bottle, pre-weighed). The bottle was weighed after the addition of Et$_2$Zn and molarity calculated (1.3M).

2). (CH$_2$I)$_2$Zn DME Preparation: To a dried flask under argon was added Et$_2$Zn in CH$_2$Cl$_2$ (1.3M, 8.8 mL). The solution was cooled to −10° C. and DME (1.2 mL) was added. The resulting mixture was cooled to −20° C. then CH$_2$I$_2$ (0.94 mL) was added via syringe pump over 25 min.

3). Into another flask containing 3-(1-iso-propyl-4,4-dimethyl-3,4-dihydronaphthalen-7-yl)-but-2(Z)-en-1-ol (Compound 58, 281 mg, 1.04 mmol) were added under argon mol. sieves (1.5 g), D(−)borolidine-tartaramide (562 mg, 2.08 mmol) followed by anhydrous CH$_2$Cl$_2$ (15 mL). The mixture was cooled to −78° C. and into this mixture (−20° C.) (CH$_2$I)$_2$Zn DME solution was cannulated. The mixture was stirred at −25° C. for 18 h then at −5° C. for 4 h.

For work-up the reaction was quenched by adding NH$_4$Cl (sat.) and extracted with ether (3×50 mL). The combined organic layers were washed with water and brine. Th solvent was dried and removed by evaporation. Purification by column chromatography gave the title compound as a clear oil 201 mg (68%).

$^1$H NMR (300 MHz, CDCl$_3$) 0.79–0.82 (m, 1H), 0.83–0.89 (m, 1H), 1.18 (d, 6H, J=6.7 Hz), 1.24 (s, 6H), 1.2–1.3 (m, 1H), 1.42 (s, 3H), 2.18 (d, 2H, J=4.4 Hz), 3.00 (m, 1H), 3.29 (m, 2H), 5.79 (t, 1H, J=4.4 Hz), 7.14 (d, 1H, J=7.8 Hz), 7.24 (d, 1H, J=7.8 Hz), 7.28 (s, 1H).

4,7,7-Trimethyl-3-oxo-2-oxa-bicyclo[2,2,1]heptane-1-carboxylic acid 3-(1-isopropyl-4,4-dimethyl-3,4-dihydronaphthalen-7-yl)-(2R,3S)-2,3-methano-butyl-ester (Compound 60) and its diastereomer A mixture of 3-(1-isopropyl-4,4-dimethyl-3,4-dihydronaphthalen-7-yl)-(2R,3S)-2,3-methano-butan-1-ol and its enantiomer (Compound 59, 201 mg, 1.4 mmol), CH$_2$Cl$_2$ (4 mL), 1(s)-(s)camphanic chloride (486 mg), triethylamine (4 mL), and DMAP (25 mg) was heated to 55° C. for 16 h. The reaction mixture was diluted with ether, washed with water, NaHCO$_3$ (sat.), and brine. The solvent was dried (MgSO$_4$) and removed by evaporation. Purification by silica gel column chromatography gave 200 mg (61%) white solid. The two diastereomers were isolated by HPLC (Normal phase, 6% EtOAc/Hexane) separation to give the desired diastereomer (Compound 60)

$^1$H NMR (300 MHz, CDCl$_3$) δ 0.94 (s, 3H), 0.85–1.00 (m, 2H), 1.01 (s, 3H), 1.10 (s, 3H), 1.15 (d, 6H, J=6.6 Hz), 1.19 (s, 6H), 1.3–1.5 (m, 1H), 1.39 (s, 3H), 1.65–1.71 (m, 1H), 1.84–1.99 (m, 2H), 2.14 (d, 2H, J=4.7 Hz), 2.30–2.35 (m, 1H), 2.98 (m, 1H), 3.74 (dd, 1H, J=7.7, 11.4 Hz), 3.99 (dd, 1H, J=7.7, 11.4 Hz), 5.75 (t, 1H, J=4.4 Hz), 7.09 (d, 1H, J=7.8 Hz), 7.20 (d, 1H, J=7.9 Hz), 7.23 (s, 1H).

3-(1-Isopropyl-4,4-dimethyl-3,4-dihydronaphthalen-7-yl)-(2R,3S)-2,3-methano-butan-1-ol (Compound 61)

To a solution of camphanic ester (Compound 60, 80 mg) in THF (3 mL) and MeOH (2 mL) was added KOH (1M solution in H$_2$O) (0.6 mL). The mixture was heated to 75° for two hours, cooled to ambient temperature and the solvents THF and MeOH were removed under reduced pressure. The residue was diluted with water and extracted with ether. Combined ether layers were washed with water and brine. The solvent was dried (MgSO$_4$) and removed by evaporation to give the title compound (46 mg, 96%).

3-(1-Isopropyl-4,4-dimethyl-3,4-dihydronaphthalen-7-yl)-(2R,3S)-2,3-methano-butanol (Compound 62)

To 3-(1-isopropyl-4,4-dimethyl-3,4-dihydronaphthalen-7-yl)-(2R,3S)-2,3-methano-butan-1-ol (Compound 61, 46 mg) was added mol. sieves (500 mg), NMO (2.5 eq), TPAP (10 mg) followed by CH$_2$Cl$_2$ (5 mL) and CH$_3$CN (0.6 mL). The mixture was stirred at ambient temperature under argon for 1.5 h. The mixture was purified by column chromatography to yield the title compound as a clear oil (30 mg, 69%).

$^1$H NMR (300 MHz, CDCl$_3$) δ 0.8–1.0 (m, 1H), 1.14 (s, 6H), 1.46 (s, 3H), 1.20 (d 6H, J=6.7 Hz), 1.8–2.0 (m, 2H), 2.15 (d, 2H, J=4.6 Hz), 2.94 (m, 1H), 5.96 (t, 1H, J=4.7 Hz), 7.14 (d, 1H, J=6.1 Hz), 7.22 (d, 1H, J=6.1 Hz), 7.25 (S, 1H), 8.42 (d, 1H, J=7.2 Hz).

Ethyl 7-(1-isopropyl-4,4-dimethyl-3,4-dihydronaphthalen-7-yl](6S,7S)-6,7-methano-3,7-dimethyl-hepta-2E,4E-dienooate (Compound 63)

To a solution of diethyl-(E)-3-ethoxycarbonyl-2-methylallylphosphonate (154 mg) in THF (12 mL) at −78° C. was added n-BuLi (1.6M, 0.36 mL) drop-wise, and after five minutes (Compound 62, 30 mg) in THF (2+2 mL) was added drop-wise. The reaction mixture was warmed gradually to −10° C. Water was added to the reaction mixture and the mixture extracted with ethyl acetate. The combined organic layers were washed with water and brine. The solvent was dried (MgSO$_4$) and was removed by evaporation. Purification by silica gel column chromatography gave 38 mg product contaminated with minor amount of the 13-cis isomer. The product was purifieded by HPLC separation, to provide the title compound (34 mg, 82%).

$^1$H NMR (300 MHz, CDCl$_3$) δ 1.1–1.3 (m, 2H), 1.17 (s, 6H), 1.24 (d, 6H, J=6.7 Hz), 1.26 (t, 3H, J=7.1 Hz), 1.42 (s, 3H), 1.70–1.75 (m 1H), 1.96 (s, 3H), 2.17 (d, 2H, J=4.7 Hz), 2.94 (m, 1H), 4.14 (q, 2H, J=7.1 Hz), 5.22 (dd, 1H, J=10.0, 15.5 Hz), 5.62 (s, 1H), 5.76 (t, 1H, J=4.7 Hz), 6.20 (d, 1H, J=15.5 Hz), 7.08 (d, 1H, J=7.9 Hz), 7.21 (s, 1H), 7.25 (d, 1H, J=8.1 Hz).

7(1-Isoproply-4,4-dimethyl-3,4-dihydronaphthalen-7-yl](6S,7S)-6,7-methano-3,7-dimethyl-hepta-2E, 4E-dienoic acid (Compound 64)

To a solution of ethyl 7-(1-isopropyl-4,4-dimethyl-3,4-dihydronaphthalen-7-yl](6S,7S)-6,7-methano-3,7-dimethyl-hepta-2E,4E-dienooate (Compound 63, 34 mg) in THF (2 mL), methanol (4 mL) was added NaOH (1M solution, 1 mL). The mixture was heated to 75° C. for 15 hours. The solvents THF and methanol were removed under vacuum. The residue was diluted with ethyl acetate, acidified with 10% HCl (pH=2). The organic layer was washed with water and brine. The solvent was dried and removed by evaporation. Flash column chromatography gave the title compound as a white solid (19 mg, 60%).

$^1$HNMR (300 MHz, CDCl$_3$) δ 1.1–1.3 (m, 2H), 1.19 (s, 6H), 1.26 (d, 6H, J=6.7 Hz), 1.44 (s, 3H), 1.7–1.8 (m 1H), 1.97 (s, 3H), 2.18 (d, 2H, J=4.7 Hz), 2.94 (m, 1H), 5.29 (dd, 1H, J=10.0, 15.5 Hz), 5.65 (s, 1H), 5.77 (t, 1H, J=4.7 Hz), 6.24 (d, 1H, J=15.5 Hz), 7.10 (d, 1H, J=7.8 Hz), 7.21 (s, 1H), 7.24 (d, 1H, J=7.8 Hz).

7-bromo-2,2-dimethyl-chroman-4-one (Compound 65)

Approximately 15 g of polyphosphoric acid was added to a mixture of 3,3-dimethylarylic acid (5.0 g, 54.9 mmol) and 3-bromophenol (10.4 g, 60.4 mmol). The mixture was stirred at 95° C. under argon for 4 hours. After cooling to 0° C. with an ice bath, the slurry was dissolved in 200 mL of ice/water and extracted with diethyl ether (3×100 mL). The organic phase was separated, washed with KOH aqueous solution (5N, 50 mL) and brine (50 mL). The extract was then dried (Mg$_2$SO$_4$), filtered, and concentrated in vacuo.

The residue was purified by column chromatography on silica gel (5% EtOAc:hexane) to yield the title compound as a brown solid: (2.80 g, 22% yield), $^1$H-NMR (300 MHz, CDCl$_3$): δ 1.45 (s, 6H), 2.71 (s, 2H), 7.13 (m, 2H), 7.72 (d, 1H, J=8.3 Hz).

7-Bromo-4-isopropyl-2,2-dimethyl-2H-chromene (Compound 66)

A 2.0 M solution of isopropyl magnesium chloride in diethyl ether (15.5 mL, 31 mmol) was added slowly to a solution of 7-bromo-2,2-dimethyl-chroman-4-one (Compound 65, 1.58 g, 6.2 mmol) and 1,3-dimethyl-3,4,5,6-tetrahydro 2(1H) pyrimidone (DMPU) (7.5 mL, 30 mmol) in 30 mL THF at −30° C. The reaction mixture was warmed to room temperature and stirred for 15 hours. The reaction was then quenched with water (20 mL), saturated NH$_4$Cl (aq) (15 mL) and 10% HCl (20 mL) at −78° C. The mixture was warmed to room temperature, was extracted with ethyl acetate (3×30 mL), the combined extracts were washed with water and brine, dried (MgSO$_4$), filtered, and concentrated in vacuo. The residue was then refluxed in 40 mL methanol with p-toluenesulfonic acid (160 mg) for 20 hours. The reaction mixture was made basic by addition of solid K$_2$CO$_3$, the solvent was removed and the residue was dissolved in diethyl ether (50 mL). The ether solution was washed with water (2×50 mL) and brine (50 mL), dried (MgSO$_4$), filtered and concentrated in vacuo. The resulting crude product was purified by column chromatography on silica gel (hexane) to give the title compound as a clear oil: (650 mg, 37%).

$^1$H-NMR (300 MHz, CDCl$_3$): δ 1.12 (d, 6H, J=6.7 Hz), 1.40 (s, 6H), 2.80 (m, 1H, J=1.1 Hz), 5.40 (s, 1H), 7.0 (m, 3H).

7-Bromo-4-t-butyl-2,2-dimethyl-2H-chromene (Compound 67)

7-bromo-2,2-dimethyl-chroman-4-one (Compound 65, 1.8 g, 7 mmol) was treated by the procedure described immediately above (using t-butylmagnesium chloride) to produce the title compound as a clear oil: (500 mg, 25%).

$^1$H-NMR (300 MHz, CDCl$_3$): δ 1.27 (s, 9H), 1.34 (s, 6H),), 5.49 (s, 1H), 6.95 (s, 1H), 6.98 (s, 1H), 7.38 (d, 1H, J=8.2 Hz).

7-Bromo-4-n-butyl-2,2-dimethyl-2H-chromene (Compound 68)

7-bromo-2,2-dimethyl-chroman-4-one (Compound 65, 1.58 g, 6.20 mmol) was treated by the procedure described above (using n-butyl magnesium chloride) for the preparation of Compound 66 to produce the title compound as a clear oil: (1.07 g, 59%).

$^1$H-NMR (300 MHz, CDCl$_3$): δ 0.91 (t, 3H), 1.28 ~1.41 (m, 10H), 2.28 (t, 2H, J=7.70 Hz), 5.40 (s, 1H), 7.0 (m, 3H).

3-(4-(isopropyl-2,2-dimethyl-2H-chromen-7-yl)-but-2-en-1-ol) (Compound 69)

A 1.7 M solution of t-BuLi in pentane (2.7 mL, 4.6 mmol) was added dropwise into a solution of 7-bromo-4-isopropyl-2,2-dimethyl-2H-chromene (Compound 66, 650 mg, 2.3 mmol) in 10 ml of anhydrous THF at −78° C. After stirring under argon for 1 hour, trimethylborate (0.52 mL, 4.6 mmol) was added to the reaction mixture and the mixture was slowly warmed up to room temperature. The reaction was quenched with saturated NH$_4$Cl (aq) (10 mL), and extracted with ethyl acetate (2×25 mL). The extract was washed with 10% HCl (15 mL), and brine (15 mL), dried (MgSO$_4$), filtered and concentrated in vacuo. The residue was dissolved in degassed methanol (5 mL), water (5 mL) and toluene (10 mL) and 3-iodobut-2(Z)-en-1-ol (1.02 g, 4.8 mmol), Na$_2$CO$_3$ (1.50 g, 14.5 mmol), and Pd(0) (PPh$_3$)$_4$ (catalyze, 48 mg) were added to the solution. The mixture was then heated at 95° C. for 20 hours. After cooling to room temperature, the mixture was extracted with diethyl ether (30 mL), washed with water (2×30 mL) and brine (30 mL), dried (MgSO$_4$), filtered and concentrated in vacuo. The crude product was purified by column chromatography on silica gel (5% 15% EtOAc:hexane) to yield the title compounds as a brown oil: (176 mg, 26%).

$^1$H-NMR (300 MHz, CDCl$_3$): δ 1.12 (d, 6H, J=6.7 Hz), 1.40 (s, 6H), 2.06 (s, 3H), 2.80 (m, 1H, J=1.1 Hz), 4.1 (t, 2H, J=6.0 Hz), 5.40 (s, 1H), 5.67 (t, 1H, J=6.0 Hz), 6.65 (d, 1H, J=1.8 Hz), 6.69 (dd, 1H, J=1.8, 7.9 Hz), 7.19 (d, 1H, J=8.0 Hz).

3-(4-(t-butyl-2,2-dimethyl-2H-chromen-7-yl)-but-2(Z)-en-1-ol) (Compound 70)

Bromo-4-t-butyl-2,2-dimethyl-2H-chromene (Compound 67, 500 mg, 1.69 mmol) was treated by the procedure described above for the production of Compound 69, to yield the title compound as a brown oil: (242 mg, 50%).

$^1$H-NMR (300 MHz, CDCl$_3$): δ 1.30 (s, 9H), 1.36 (s, 6H), 2.04 (s, 3H), 4.13 (t, 2H, J=6.0 Hz), 5.48 (s, 1H), 5.65 (t, 1H, J=6.0 Hz), 6.65 (s, 1H), 6.70 (s, 1H), 7.48 (d, 1H, J=8.0 Hz).

3-(4-(n-butyl-2,2-dimethyl-2H-chromen-7-yl)-but-2(Z)-en-1-ol) (Compound 71)

Bromo-4-n-butyl-2,2-dimethyl-2H-chromene (Compound 68, 570 mg, 1.93 mmol) was treated by the procedure described above for the production of Compound 69, to yield the title compound as a brown oil: (288 mg, 52%).

$^1$H-NMR (300 MHz, CDCl$_3$): δ 0.93 (t, 3H, J=7.14 Hz), 1.30~1.58 (m, 10H), 2.06 (s, 3H), 2.33 (t, 2H, J=7.7 Hz), 4.12 (t, 2H, J=6.0 Hz), 5.40 (s, 1H), 5.67 (t, 1H, J=6.0 Hz), 6.63 (d, 1H, J=1.7 Hz), 6.70 (d, 1H, J=7.9 Hz), 7.12 (d, 1H, J=7.9 Hz).

2-[(4-Isopropyl-2,2-dimethyl-2H-chromene-7-yl)]-(2R,3S) 2,3-methano-butan-1-ol (Compound 72)

To a solution of 1.15M Et$_2$Zn in CH$_2$Cl$_2$ (10 mL, 11.6 mmol) and DME (1.2 mL, 11.6 mmol) at −40° C. was added CH$_2$I$_2$ (6.21 g, 23.3 mmol) drop-wise and under argon. The solution was then cannulated directly to a mixture of (−)-D-tartaramide derived dioxaborolane (500 mg, 1.83 mmol), 3-(4-(isopropyl-2,2-dimethyl-2H-chromen-7-yl)-but-2(Z)-en-1-ol) (Compound 69, 180 mg, 0.58 mmol), and 4 Å molecular sieves (60 mg) in 10 mL CH$_2$Cl$_2$ at −40° C. The resulting mixture was stirred at −25° C. for 3 days, quenched with saturated NH$_4$Cl (aq) (20 mL) and extracted with CH$_2$Cl$_2$ (3×20 mL). The extract was washed with water, brine, and dried (MgSO$_4$), filtered and concentrated in vacuo. The residue was then chromatographed on silica gel (20% EtOAc:hexane) to afford the title compound as a colorless oil: (175 mg, 94%).

2-[(4-t-butyl-2,2-dimethyl-2H-chromene-7-yl)]-(2R, 3S) 2,3-methano-butan-1-ol (Compound 73)

3-(4-(t-butyl-2,2-dimethyl-2H-chromen-7-yl)-but-2(Z)-en-1-ol) (Compound 70, 224 mg, 0.75 mmol) was treated by the procedure described above for the production of Compound 72, to yield the title compound as a colorless oil (217 mg, 92%).

2-[(4-n-butyl-2,2-dimethyl-2H-chromene-7-yl)]-(2R,3S) 2,3-methano-butan-1-ol (Compound 74)

3-(4-(n-butyl-2,2-dimethyl-2H-chromen-7-yl)-but-2(Z)-en-1-ol) (Compound 71, 288 mg, 1.01 mmol) was treated by the procedure described above for the production of Compound 72, to yield the title compound as a light yellow oil (179 mg, 59%).

4,7,7-Trimethyl-3-oxo-2-oxa-bicyclo[2,2,1]heptane-1-carboxylic acid 2-(4-isopropyl-2,2-dimethyl-2H-chromen-7-yl)-(2R,3S)-2,3-methano-butan-1-ol ester (Compound 75) and [2-(4-isopropyl-2,2-dimethyl-2H-chromene-7-yl)-(2R,3S) 2-methano-butan-1-ol (Compound 78)

To a solution of 2-[(4-isopropyl-2,2-dimethyl-2H-chromene-7-yl)]-(2S,3S) 2,3-methano-butan-1-ol (Compound 72, 170 mg, 0.58 mmol) and (−)-camphanic acid chloride (253 mg, 1.17 mmol) in CH$_2$Cl$_2$ (5 mL) was added TEA (0.24 mL, 1.75 mmol) at room temperature under argon. The resulting mixture was stirred at room temperature for 15 hours, then diluted with CH$_2$Cl$_2$, washed with H$_2$O and brine, and dried (MgSO$_4$) and concentrated in vacuo. The crude product was purified successively by column chromatography on silica gel (20% EtOAc:hexane), and recrystalization (hexane) to give the optically pure camphanic ester Compound 75 as a white solid: (250 mg 92%).

The camphanic ester Compound 75 was then hydrolyzed with 5N aqueous LiOH (10 mL) in 1:1 THF 1 MeOH (20 mL) for 3 hours at room temperature. The solvents were removed by evaporation, the crude product residue was diluted with water, extracted with diethyl ether, and the ether extract was dried (MgSO$_4$), filtered and concentrated in vacuo. The residue was purified by column chromatography on silica gel (15% EtOAc:hexane) to give optically pure [2-(4-isopropyl-2,2-dimethyl-2H-chromene-7-yl)-(2R,3S) 2,3-methano-butan-1-ol (Compound 78) as a colorless oil (126 mg, 93%).

$^1$H-NMR (300 MHz, CDCl$_3$): δ 0.71 (dd, 1H, J=4.9, 8.5 Hz), 0.87 (t, 1H, J=5.1 Hz), 1.11 (d, 3H, J=1.8 Hz), 1.13 (d, 3H, J=1.9 Hz), 1.25 (m, 1H), 1.36 (d, 6H, J=2.0 Hz), 1.38 (s, 3H), 2.80 (m, 1H, J=1.1 Hz), 3.25 (m, 2H), 5.40 (s, 1H), 6.74 (d, 1H, J=1.8 Hz), 6.83 (dd, 1H, J=1.8, 7.9 Hz), 7.13 (d, 1H, J=8.0 Hz).

4,7,7-Trimethyl-3-oxo-2-oxa-bicyclo[2,2,1]heptane-1-carboxylic acid 2-(4-t-butyl-2,2-dimethyl-2H-chromen-7-yl)-(2R,3S)-2,3-methano-butan-1-ol ester (Compound 76) and 2-[(4-t-Butyl-2,2-dimethyl-2H-chromene-7-yl)]-(2R,3S) 2,3-methano-butan-1-ol (Compound 79)

2-[(4-t-Butyl-2,2-dimethyl-2H-chromene-7-yl)]-(2R,3S) 2,3-methano-butan-1-ol (Compound 73, 217 mg, 0.69 mmol) was used in the procedure described above for the preparation of Compounds 75 to yield 4,7,7-trimethyl-3-oxo-2-oxa-bicyclo[2,2,1]heptane-1-carboxylic acid 2-(4-t-butyl-2,2-dimethyl-2H-chromen-7-yl)-(2S,3S)-2,3-methano-butan-1-ol ester (Compound 76) as a white solid: (236 mg, 71%). Compound 76 was then hydrolyzed to yield optically pure 2-[(4-t-butyl-2,2-dimethyl-2H-chromene-7-yl)]-(2R,3S) 2,3-methano-butan-1-ol (Compound 79) as a colorless oil: (144 mg, 93%). $^1$H-NMR (300 MHz, CDCl$_3$): δ 0.73 (dd, 1H, J=3.7, 8.6 Hz), 0.87 (t, 1H, J=5.1 Hz), 1.11 (d, 3H, J=1.8 Hz), 1.28 (s, 9H), 1.35 (m, 10H), 3.26 (m, 2H), 5.44 (s, 1H), 6.77 (dd, 1H, J=1.9, 4.9 Hz), 6.81 (d, 1H, J=2.1 Hz), 7.44 (d, 1H, J=8.1 Hz).

4,7,7-Trimethyl-3-oxo-2-oxa-bicyclo[2,2,1]heptane-1-carboxylic acid 2-(4-n-butyl-2,2-dimethyl-2H-chromen-7-yl)-(2R,3S)-2,3-methano-butan-1-ol ester (Compound 77) and 2-[(4-n-Butyl-2,2-dimethyl-2H-chromene-7-yl)]-(2R,3S) 2,3-methano-butan-1-ol (Compound 80)

2-[(4-n-butyl-2,2-dimethyl-2H-chromene-7-yl)]-(2R,3S) 2,3-methano-butan-1-ol (Compound 74, 179 mg, 0.60 mmol) was used in the procedure described above for the preparation of Compounds 75, except for using HPLC (10% EtOAc:Hexane) for purification in this instance, to yield 4,7,7-trimethyl-3-oxo-2-oxa-bicyclo[2,2,1]heptane-1-carboxylic acid 2-(4-n-butyl-2,2-dimethyl-2H-chromen-7-yl)-(2R,3S)-2-methano-butan-1-ol ester (Compound 77) as a white solid: (163 mg, 57%). Compound 77 was then hydrolyzed to yield optically pure 2-[(4-n-butyl-2,2-dimethyl-2H-chromene-7-yl)]-(2R,3S) 2,3-methano-butan-1-ol (Compound 80) as a colorless oil: (101 mg, 98%).

$^1$H-NMR (300 MHz, CDCl$_3$): δ 0.75 (dd, 1H, J=3.8, 8.5 Hz), 0.87–0.93 (m, 4H), 1.28~1.5 (m, 5H), 1.36 (s, 6H), 1.38 (s, 3H), 2.31 (t, 2H, J=7.7 Hz), 3.23 (m, 2H), 5.33 (s, 1H), 6.73 (d, 1H, J=1.7 Hz), 6.79 (dd, 1H, J=1.8, 7.9 Hz), 7.06 (d, 1H, J=7.9 Hz).

2-(4-Isopropyl-2,2-dimethyl-2H-chromen-7-yl)-(2R, 3S)-2,3-methano-butanal (Compound 81)

To a mixture of [2-(4-isopropyl-2,2-dimethyl-2H-chromene-7-yl)-(2R,3S) 2,3-methano-butan-1-ol (Compound 78,125 mg, 0.42 mmol), CH$_3$CN (1 mL) in $CH_2Cl_2$ (10 mL) was added N-methyl morpholane N-oxide (NMO) (98 mg, 0.83 mmol), 4 Å molecular sieves (50 mg) and tetrapropylammonium perruthenium (TPAP) (6 mg). After stirring at room temperature for 1 hour, the solution was concentrated in vacuo and the residue was purified by silica gel column chromatography (5% EtOAc:hexane) to yield the title compound as a colorless oil (112 mg, 90%).

$^1$H-NMR (300 MHz, $CDCl_3$): δ 1.10 (d, 3H, J=3.0 Hz), 1.12 (d, 3H, J=3.0 Hz), 1.36 (s, 3H), 1.38 (s, 3H), 1.5 (m, 1H), 1.86 (m, 2H), 2.80 (m, 1H, J=1.1 Hz), 5.40 (s, 1H), 6.77 (d, 1H, J=1.8 Hz), 6.83 (dd, 1H, J=1.8, 7.9 Hz), 7.13 (d, 1H, J=8.0 Hz), 8.41 (d, 1H, J=7.1 Hz).

2-(4-t-butyl-2,2-dimethyl-2H-chromen-7-yl)-(2R, 3S)-2,3-methano-butanal (Compound 82)

[2-(4-t-butyl-2,2-dimethyl-2H-chromene-7-yl)-(2R,3S) 2-methano-butan-1-ol (Compound 79, 140 mg, 0.55 mmol) was used in the procedure described above for the preparation of Compound 81 to yield the title compound as a colorless oil (115 mg, 83%).

$^1$H-NMR (300 MHz, $CDCl_3$): δ 1.28 (s, 9H), 1.33 (s, 3H), 1.36 (s, 3H), 1.43 (m, 4H), 1.86 (m, 2H), 5.46 (s, 1H), 6.78 (d, 1H, J=4.8 Hz), 6.81 (s, 1H), 7.44 (d, 1H, J=8.7 Hz), 8.41 (d, 1H, J=8.1 Hz).

2-(4-n-butyl-2,2-dimethyl-2H-chromen-7-yl)-(2R, 3S)-2,3-methano-butanal (Compound 83)

[2-(4-n-butyl-2,2-dimethyl-2H-chromene-7-yl)-(2R,3S) 2,3-methano-butan-1-ol (Compound 80, 101 mg, 0.34 mmol) was used in the procedure described above for the preparation of Compound 81 to yield the title compound as a colorless oil: (88 mg, 88%).

$^1$H-NMR (300 MHz, $CDCl_3$): δ 0.91 (t, 3H, J=7.2 Hz), 1.2~1.53 (m, 5H), 1.35 (s, 3H), 1.38 (s, 3H), 1.43 (s, 3H), 1.85 (m, 2H), 2.32 (t, 2H, J=7.9 Hz), 5.34 (s, 1H), 6.75 (d, 1H, J=1.7 Hz), 6.79 (dd, 1H, J=7.8 Hz), 7.06 (d, 1H, J=7.8 Hz), 8.41 (d, 1 H, J=7.1 Hz).

Ethyl 7-[4-isopropyl-2,2-dimethyl-2H-chromen-7-yl)]-(6S,7S)-6,7-methano-3,7-dimethyl-hepta-2E,4E-dienoate (Compound 84)

A solution of 1.6M n-BuLi in hexane (0.95 mL, 1.503 mmol) was added slowly to a mixture of diethyl (E)-3-ethoxycarbonyl-2-methylallylphosphonate (397 mg, 1.50 mmol), DMPU (5 mL) in THF (15 mL under argon at −78° C. After stirring for 30 min, a solution of 2-(4-isopropyl-2,2-dimethyl-2H-chromen-7-yl)-(2R,3S)-2,3-methano-butanal (Compound 81, 112 mg, 0.38 mmol) in THF (5 mL) was added, and the mixture was stirred for additional 4 hours at −78° C. The reaction mixture was then warmed to room temperature, and quenched with water (20 mL), and extracted with ether (2×50 mL). The extract was washed with water, brine, and dried ($MgSO_4$), filtered and concentrated in vacuo. The crude product was purified successively by column chromatography on silica gel (5% EtOAc:hexane) and HPLC (10% $H_2O:CH_3CN$) to afford the title compound as a white solid: (129 mg, 83%).

$^1$H-NMR (300 MHz, $CDCl_3$): δ 1.12 (m, 8H), 1.24 (t, 3H, J=7.1 Hz), 1.32 (s, 3H), 1.40 (s, 6H), 1.70 (m, 1H), 1.96 (s, 3H), 2.80 (m, 1H), 4.12 (q, 2H, J=7.1 Hz), 5.21 (dd, 1H, J=9.9, 15.5 Hz), 5.34 (s, 1H), 5.60 (s, 1H), 6.12 (d, 1H, J=15.5 Hz), 6.70 (d, 1H, J=1.8 Hz), 6.73 (dd, 1H, J=1.8, 7.9 Hz), 7.10 (d, 1H, J=8.0 Hz).

Ethyl 7-[4-t-butyl-2,2-dimethyl-2H-chromen-7-yl)]-(6S,7S)-6,7-methano-3,7-dimethyl-hepta-2E,4E-dienoate (Compound 85)

2-(4-t-Butyl-2,2-dimethyl-2H-chromen-7-yl)-(2R,3S)-2,3-methano-butanal (Compound 82, 115 mg, 0.37 mmol) was treated in the procedure described above to produce Compound 84, to yield the title compound as a white solid (130 mg, 83%).

$^1$H-NMR (300 MHz, $CDCl_3$): δ 1.14–1.19 (m, 2H), 1.24 (t, 3H, J=7.1 Hz), 1.28 (s, 9H), 1.29 (s, 3H), 1.38 (s, 3H), 1.39 (s, 3H), 1.70 (m, 1H), 1.96 (s, 3H), 4.12 (q, 2H, J=7.1 Hz), 5.21 (dd, 1H, J=10.0, 15.5 Hz), 5.44 (s, 1H), 5.60 (s, 1H), 6.12 (d, 1H, J=15.5 Hz), 6.72 (d, 1H, J=1.8 Hz), 6.73 (dd, 1H, J=1.8, 7.9 Hz), 7.43 (d, 1H, J=8.6 Hz).

Ethyl 7-[4-n-butyl-2,2-dimethyl-2H-chromen-7-yl)]-(6S,7S)-6,7-methano-3,7-dimethyl-hepta-2E,4E-dienoate (Compound 86)

2-(4-n-Butyl-2,2-dimethyl-2H-chromen-7-yl)-(2R,3S)-2,3-methano-butanal (Compound 83, 88 mg, 0.30 mmol) was treated in the procedure described above to produce Compound 84, to yield the title compound as a white solid (90 mg, 74%).

$^1$H-NMR (300 MHz, $CDCl_3$): δ 0.91 (t, 3H, J=7.2 Hz), 1.12 (dd, 2H, J=2.3, 7.8 Hz), 1.24 (t, 3H, J=7.1 Hz), 1.32 (s, 3H), 1.38 (s, 3H), 1.39 (s, 3H), 1.54 (m, 4H), 1.7 (m, 1H), 1.96 (s, 3H), 2.32 (t, 2H, J=7.9 Hz), 4.12 (q, 2H, J=7.2 Hz), 5.19 (dd, 1H, J=10.1, 15.5 Hz), 5.34 (s, 1H), 5.60 (s, 1H), 6.13 (d, 1H, J=15.5 Hz), 6.68 (d, 1H, J=1.7 Hz), 6.72 (dd, 1H, J=1.7, 7.8 Hz), 7.05 (d, 1H, J=7.9 Hz).

7-[4-Isopropyl-2,2-dimethyl-2H-chromen-7-yl)]-(6S, 7S)-6,7-methano-3,7-dimethyl-hepta-2E,4E-dienoic acid (Compound 87)

Ethyl 7-[4-isopropyl-2,2-dimethyl-2H-chromen-7-yl)]-(6S,7S)-6,7-methano-3,7-dimethyl-hepta-2E,4E-dienoate (Compound 84, 128 mg, 0.44 mmol) was dissolved in methanol (10 mL) and THF (10 mL), and treated with 1N NaOH (aq) (10 mL). The solution was heated to 55° C. for 14 hours and concentrated in vacuo. The residue was dissolved in water (10 mL), and acidified with 20% aqueous HCl. The product was extracted with ether (3×30 mL), the extract was washed with water and brine, and dried ($MgSO_4$), filtered, and concentrated in vacuo. The residue was recrystalized by 20% EtOAc:hexane to yield the title compound as a white solid: (107 mg, 90%).

$^1$H-NMR (300 MHz, $CDCl_3$): δ 1.12 (m, 8H), 1.32 (s, 3H), 1.40 (s, 6H), 1.70 (m, 1H), 1.96 (s, 3H), 2.80 (m, 1H, J=1.1 Hz), 5.21 (dd, 1H, J 9.9, 15.5 Hz), 5.34 (s, 1H), 5.60 (s, 1H), 6.12 (d, 1H, J=15.0 Hz), 6.70 (d, 1H, J=1.8 Hz), 6.73 (d, 1H, J=1.8, 7.9 Hz), 7.10 (d, 1H, J=8.0 Hz).

7-[4-t-Butyl-2,2-dimethyl-2H-chromen-7-yl)]-(6S, 7S)-6,7-methano-3,7-dimethyl-hepta-2E,4E-dienoic acid (Compound 88)

Ethyl 7-[4-t-butyl-2,2-dimethyl-2H-chromen-7-yl)]-(6S, 7S)-6,7-methano-3,7-dimethyl-hepta-2E,4E-dienoate (Compound 85, 130 mg, 0.32 mmol) was used in the procedure described above to obtain Compound 87, to produce the title compound as a white solid (93 mg, 77%).

$^1$H-NMR (300 MHz, $CDCl_3$): δ 1.14–1.19 (m, 2H), 1.28 (s, 9H), 1.29 (s, 3H), 1.38 (s, 3H), 1.39 (s, 3H), 1.70 (m, 1H), 1.96 (s, 3H), 5.21 (dd, 1H, J=10.0, 15.5 Hz), 5.44 (s, 1H), 5.60 (s, 1H), 6.12 (d, 1H, J=15.5 Hz), 6.72 (d, 1H, J=1.8 Hz), 6.73 (dd, 1H, J=1.8, 7.9 Hz), 7.43 (d, 1H, J=8.6 Hz).

7-[4-n-Butyl-2,2-dimethyl-2H-chromen-7-yl)-]-(6S, 7S)-6,7-methano-3,7-dimethyl-hepta-2E,4E-dienoic acid (Compound 89)

Ethyl 7-[4-n-butyl-2,2-dimethyl-2H-chromen- 7-yl)]-(6S, 7S)-6,7-methano-3,7-dimethyl-hepta-2E,4E-dienoate (Compound 86, 90 mg, 0.22 mmol) was used in the procedure described above to obtain Compound 87, to produce the title compound as a white solid: (78 mg, 93%).

$^1$H-NMR (300 MHz, CDCl$_3$): δ 0.91 (t, 3H, J=7.2 Hz), 1.12 (dd, 2H, J=2.3, 7.8 Hz), 1.32 (s, 3H), 1.38 (s, 3H), 1.39 (s, 3H), 1.48 (m, 4H), 1.7 (m, 1H), 1.96 (s, 3H), 2.32 (t, 2H, J=7.9 Hz), 5.19 (dd, 1H, J=10.0, 15.5 Hz), 5.34 (s, 1H), 5.60 (s, 1H), 6.13 (d, 1H, J=15.5 Hz), 6.68 (d, 1H, J=1.7 Hz), 6.72 (dd, 1H, J=1.7, 7.8 Hz), 7.05 (d, 1H, J=7.9 Hz).

3-(3,5-Di-t-butylphenyl)-but-2(Z)-en-1-ol (Compound 90)

A cold (−78° C.) solution 3,5-di-t-butyl-bromobenzene ((2.46 g, 9.2 mmol) and THF (30 mL) was reacted with t-BuLi (20.2 mmols) in pentane. After 30 mins stirring between −78° C. and −10° C., trimethyl borate (1.5 g, 15 mmol) was added to the reaction and allowed the reaction to warm to ambient temperature. Aq. Ammoniumchloride was added, the mixture extracted with ethylacetate (3×30 mL) and the combined organic layers were washed with brine, dried with MgSO4 and the solvent was removed by evaporation. Argon gas was bubbled for 6 minutes into a solution of crude borate (0.753 g), 3-iodo-but-2-(Z)en-1-ol (0.76 g) and K$_2$CO$_3$ (1.9 g) in water (5 mL), MeOH (3 mL) and toluene (30 mL). Then Pd(PPh$_3$)$_4$ (70 mg) was added argon gas was bubbled into the mixture for another 2 min. The mixture was heated at 95° C. for 12 hours under argon. The mixture was then cooled to ambient temperature and diluted with ether. The organic layer was washed with water and brine, dried and concentrated. The crude product was purified by silica gel column chromatography to yield 527 mg of the clean product.

$^1$H NMR (300 MHz, CDCl$_3$) δ 1.32 (s, 18H), 2.11 (s, 3H), 4.10 (m, 2H), 5.69 (m, 1H), 7.00 (d, 2H, J=1.9 Hz), 7.33 (t, 1H, J=1.8 Hz).

3-(3,5-di-t-butyl-phenyl)-2(R),3(S)-2,3-methano-butan-1-ol (Compound 91)

1). Preparation of Et$_2$Zn in CH$_2$Cl$_2$ solution: cannulate about 10 ml Et$_2$Zn (neat) into an anhydrous CH$_2$Cl$_2$ (100 mL sealed bottle, pre-weighed). The bottle was weighed after the addition of Et$_2$Zn and molarity calculated (0.93M).

2). (CH$_2$I)$_2$Zn DME Preparation: To a dried flask under argon was added Et$_2$Zn in CH$_2$Cl$_2$ (0.93M, 22.8 mL). The solution was cooled to −10° C. and DME (2.3 mL) was added. The resulting mixture was cooled to −20° C. then CH$_2$I$_2$ (1.7 mL) was added via syringe pump over 25 min.

3). Into another flask containing 3-(3,5-di-t-butylphenyl)-but-2(Z)-en-1-ol (Compound 90, 500 mg, 1.9 mmol) were added under argon mol. sieves (1.5 g), D(−)boronlidine-tartaramide (1.04 g, 3.8 mmol) followed by anhydrous CH$_2$Cl$_2$ (30 mL). The mixture was cooled to −78° C. and into this mixture (−20° C.) (CH$_2$I)$_2$Zn DME solution was cannulated. The mixture was stirred at −25° C. for 18 h then at −5° C. for 4 h.

For workup the reaction was quenched by adding NH$_4$Cl (sat.) and extracted with ether (3×50 mL). The combined organic layers were washed with water and brine. The solvent was dried (MgSO$_4$) and was removed by evaporation. Purification by column chromatography gave the title compound as a clear oil (518 mg, 99%).

$^1$H NMR (300 MHz, CDCl$_3$) δ 0.75–0.80 (m, 1H), 0.85–0.87 (m, 1H), 1.22–1.25 (m, 1H), 1.33 (s, 18H), 1.41 (s, 3H), 3.22 (m, 2H), 7.17 (d, 2H, J=1.8 Hz), 7.26 (t, 1H, J=1.7 Hz).

4,7,7-Trimethyl-3-oxo-2-oxa-bicyclo[2,2,1]heptane-1-carboxylic acid 3 (3,5-di-t-butylphenyl)-2(R),3(S)-2,3-methano-butan-1-ol ester (Compound 92) and its diastereomer A mixture of 1-3-(3,5-di-t-butyl-phenyl)-2(R),3(S)-2,3-methano-butan-1-ol (Compound 91, 518 mg, 1.9 mmol), CH$_2$Cl$_2$ (8 mL), 1(s)-(s)camphanic chloride (1.29 g, 6.0 mmol), triethylamine (7 mL), and DMAP (50 mg) was heated to 55° C. for 16 h. The reaction mixture was diluted with ether, washed with water, NaHCO$_3$ (sat.) and brine. The solvent was dried (MgSO$_4$) and was removed by evaporation. Purification by silica gel column chromatography gave a white solid. The two diastereomers were isolated by HPLC (Normal phase, 6% EtOAc/Hexane) to give 328 mg (38%) of the desired diastereomer (Compound 92).

$^1$H NMR (300 MHz, CDCl$_3$) δ 0.8–1.0 (m, 2H), 0.97 (s, 3H), 1.04 (s, 3H), 1.12 (s, 3H), 1.2–1.39 (m, 1H), 1.32 (s, 18H), 1.39 (s, 3H), 1.63–1.73 (m, 1H), 1.83–2.03 (m, 2H), 2.32–2.45 (m, 1H), 3.67 (dd, 1H, J=7.9, 11.4 Hz), 4.08 (dd, 1H, J=6.7, 11.5 Hz), 7.12 (d, 2H, J=1.7 Hz), 7.26 (t, 1H, J=1.7 Hz).

3-(3,5-di-t-Butyl-phenyl)-2(R),3(S)-2,3-methano-butan-1-ol (Compound 93)

To a solution of camphanic ester (Compound 92, 328 mg) in THF (6 mL) and MeOH (4 mL) was added KOH (1M solution in H$_2$O) (2.5 mL). The mixture was heated to 75° for two hours, then cooled to ambient temperature and the solvents THF and MeOH were removed under reduced pressure. The residue was diluted with water and was extracted with ether. The combined ether layers were washed with water and brine. The solvent was dried (MgSO$_4$) and was removed by evaporation The solvent was dried (MgSO$_4$) and was removed by evaporation to give 178 mg (89%) product.

3-(3,5-di-t-Butyl-phenyl)-2(R),3(S)-2,3-methano-butanol (Compound 94)

To 3-(3,5-di-t-butyl-phenyl)-2(R),3(S)-2,3-methano-butan-1-ol (Compound 93, 178 mg) were added mol. sieves (600 mg), NMO (2.5 eq), TPAP (10 mg) followed by CH$_2$Cl$_2$ (5 mL) and CH$_3$CN (0.6 mL). The mixture was stirred at ambient temperature under argon for 2 h. Then the solvent was removed by evaporation. The mixture was purified by column chromatography to yield the title compound as a clear oil (164 mg, 93%).

$^1$H NMR (300 MHz, CDCl$_3$) δ 0.88 (m, 1H), 1.31 (s, 18H), 1.48 (S, 3H), 1.84–1.96 (m, 2H), 7.16 (d, 2H, J=1.7 Hz), 7.28 (t, 1H, J=1.7 Hz), 8.36 (d, 1H, J=7.2 Hz).

Ethyl-7-(3,5-di-t-butylphenyl)-(6S,7S)-6,7-methano-3,7-dimethyl-hepta-2E,4E-dienoate (Compound 95)

To a solution of diethyl-(E)-3-ethoxycarbonyl-2-methylallylphosphonate (833 mg) in THF (10 mL) at −78° C. was added n-BuLi (1.6M, 2.0 mL) dropwise, and after five minutes 3-(3,5-di-t-butyl-phenyl)-2(R),3(S)-2,3-methano-butanol (Compound 94, 156 mg) in THF (2+2 mL) was added dropwise. The reaction was warned gradually to −10° C. Water was added to the reaction mixture and extracted with ethyl acetate. The combined organic layers were washed with water and brine. The solvent was dried (MgSO$_4$) and was removed by evaporation. Purification of the residue by silica gel column chromatography gave 130 mg product contaminated with the 13-cis isomer. The product was purified by HPLC separation to afford the title compound (110 mg, 51%).

¹H NMR (300 MHz, CDCl₃) δ 1.1–1.2 (m, 1H), 1.2–1.4 (m, 4H), 1.32 (s, 18H), 1.46 (s, 3H), 1.7–1.8 (m, 1H), 2.00 (s, 3H), 4.16 (q, 2H, J=7.1 Hz), 5.24 (dd, 1H, J=10.2, 15.7 Hz), 5.66 (s, 1H), 6.23 (d, 1H, J=15.7 Hz), 7.11 (d, 2H,=1.7 Hz), 7.28 (t, 1H, J=1.6 Hz).

7-(3,5-di-t-Butylphenyl)-(6S,7S)-6,7-methano-3,7-dimethyl-hepta-2E,4E-dienoic acid (Compound 96)

To a solution of ethyl-7-(3,5-di-t-butylphenyl)-(6S,7S)-6,7-methano-3,7-dimethyl-hepta-2E,4E-dienoate (Compound 95, 110 mg, 0.28 mmol) in THF (2 mL) and methanol (4 mL) was added NaOH (1M solution, 1.6 mL). The mixture was heated to 75° C. for 15 hours. THF and methanol were removed under reduced vacuum. The residue was diluted with ethyl acetate and was acidified with 10% HCl (pH=2). The organic layer was washed with water and brine. The solvent was dried (MgSO₄) and was removed by evaporation. Flash column chromatography gave 87 mg (85%) white solid.

¹HNMR (300 MHz, CDCl₃) δ 1.1–1.2 (m, 1H), 1.2–1.3 (m, 1H), 1.32 (s, 18H), 1.45 (s, 3H), 1.7–1.8 (m, 1H), 1.99 (s, 3H), 5.29 (dd, 1H, J=10.2, 15.7 Hz), 5.66 (s, 1H), 6.24 (d, 1H, J=15.7 Hz), 7.10 (d, 2H, J=1.7 Hz), 7.28 (t, 1H, J=1.6 Hz)

What is claimed is:

1. A compound of the formula

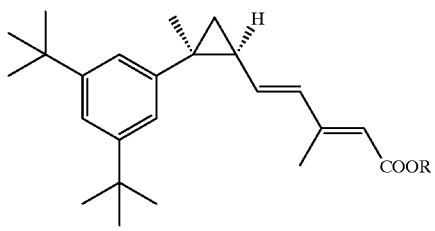

where R is H, lower alkyl of 1 to 6 carbons, or a pharmaceutically acceptable salt of said compound.

2. A compound in accordance with claim 1 where R is ethyl.

3. A compound in accordance with claim 1 where R is H, or a pharmaceutically acceptable salt of said compound.

4. A compound of the formula

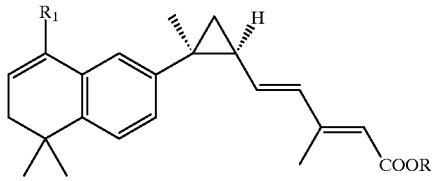

where R is H, lower alkyl of 1 to 6 carbons, and $R_1$ is iso-propyl or tertiary-butyl, or a pharmaceutically acceptable salt of said compound.

5. A compound in accordance with claim 4 where $R_1$ is iso-propyl.

6. A compound in accordance with claim 5 where R is ethyl.

7. A compound in accordance with claim 5 where R is H or a pharmaceutically acceptable salt of said compound.

8. A compound in accordance with claim 4 where $R_1$ is tertiary-butyl.

9. A compound in accordance with claim 8 where R is ethyl.

10. A compound in accordance with claim 8 where R is H or a pharmaceutically acceptable salt of said compound.

11. A compound of the formula

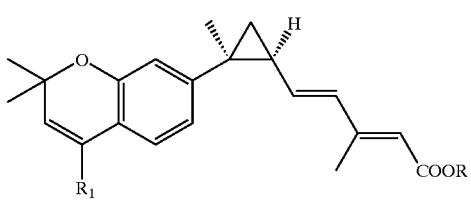

where R is H, lower alkyl of 1 to 6 carbons, and $R_1$ is iso-propyl, n-butyl or tertiary-butyl, or a pharmaceutically acceptable salt of said compound.

12. A compound in accordance with claim 11 where $R_1$ is iso-propyl.

13. A compound in accordance with claim 12 where R is ethyl.

14. A compound in accordance with claim 12 where R is H or a pharmaceutically acceptable salt of said compound.

15. A compound in accordance with claim 11 where $R_1$ is n-butyl.

16. A compound in accordance with claim 15 where R is ethyl.

17. A compound in accordance with claim 15 where R is H or a pharmaceutically acceptable salt of said compound.

18. A compound in accordance with claim 11 where $R_1$ is tertiary-butyl.

19. A compound in accordance with claim 18 where R is ethyl.

20. A compound in accordance with claim 18 where R is H or a pharmaceutically acceptable salt of said compound.

* * * * *

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

Column 2,
Line 12, "receptorsexist" should be -- receptors exist --.

Column 4,
Line 48, "O" should be -- o --.

Column 5,
Line 10, "$CONR_{9R10}$" should be -- $CONR_9R_{10}$ --.

Column 6,
Line 58, "omithine" should be -- ornithine --.

Column 8,
Line 19, "PAR" should be -- RAR --.
Line 29, "115" should be -- 1/5 --.

Column 9,
Line 18, Table 1, Compound 14, "09" should be -- 0.9 --.

Column 11,
Line 42, "patients" should be -- patient's --.

Column 12,
Line 42, "Acetals and…" should begin a new paragraph.

Column 13,
Line 18, insert -- Reaction Scheme 1 --.
Line 25, Reaction Scheme 1a, Formula 7 → Formula 9, below the arrow, "Pd(O) should be -- Pd(0) --.
Line 25, Reaction Scheme 1c, Formula 7 → Formula 15, below the arrow, "Pd(O) should be -- Pd(0) --.

Column 14,
Line 33, "4position" should be -- 4-position --.

Column 17,
Line 19, "faryl" should be -- furyl --.

Column 20,
Line 6, Reaction Scheme 2, below the arrow, "Pd(O) should be -- Pd(0) --.

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

Column 21,
Line 38, both occurrences of "C." should be -- C --.
Lines 63 and 67, "C." should be -- C --.

Column 22,
Line 24, "C" should be -- C --.
Line 53, "perrnthenate" should be -- perruthenate --.

Column 23,
Line 4, "C." should be -- C --.

Column 24,
Line 47, Reaction Scheme 4, below the arrow, "Pd(O)" should be -- Pd(0) --.

Column 27,
Line 25, Reaction Scheme 5, below the arrow, "Pd(O)" should be -- Pd(0) --.

Column 29,
Line 35, Reaction Scheme 6, below the arrow, "Pd(O)" should be -- Pd(0) --.

Column 31,
Line 35, Reaction Scheme 7, below the arrow, "Pd(O)" should be -- Pd(0) --.
Line 60, Reaction Scheme 7, above the arrow,

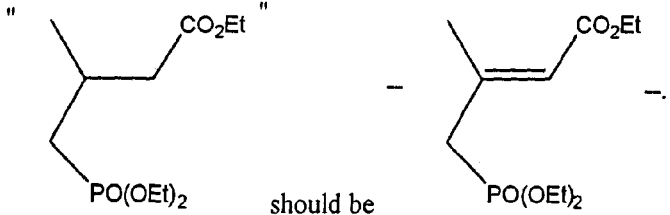

Column 33,
Line 38, Reaction Scheme 8, above the arrow, "NaI" should be -- NaI --.
Line 40, Reaction Scheme 8,

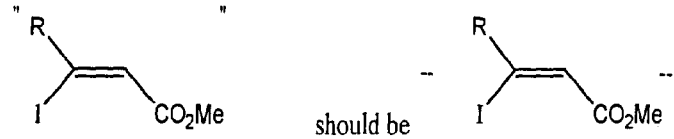

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

Column 33 cont'd,
Line 45, Reaction Scheme 8,

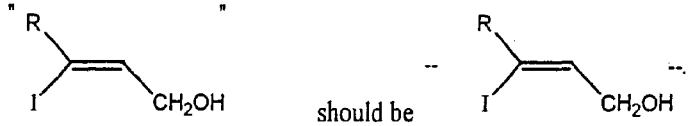

Line 54, Reaction Scheme 8, below the arrow, "Pd(O)" should be -- Pd(0) --.
Lines 56-59, Reaction Scheme 8, below the arrow,

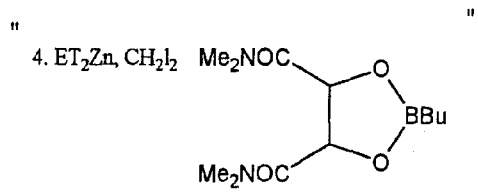

should be

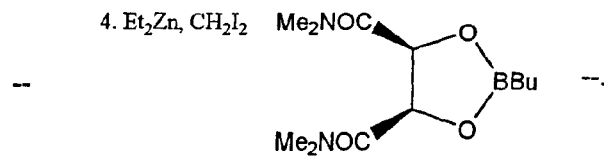

Column 34,
Line 43, "aspara" should be -- as para --.

Column 36,
Line 14, Reaction Scheme 9, right of the arrow, "$CH_2l_2$" should be -- $CH_2I_2$ --.

Column 38,
Line 15, Reaction Scheme 10, right of the arrow, "$CH_2l_2$" should be -- $CH_2I_2$ --.

Column 40,
Line 13, Reaction Scheme 11, right of the arrow, "$CH_2l_2$" should be -- $CH_2I_2$ --.
Lines 57 and 61, "C." should be -- C --.

Column 41,
Lines 8, 13, 28, 41 and, 51, "C." should be -- C --.
Line 12, first occurrence of "C." should be -- C --.
Line 58, "$^{C.}$" should be -- $^C$ --.

UNITED STATES PATENT AND TRADEMARK OFFICE
CERTIFICATE OF CORRECTION

PATENT NO.    : 6,403,638 B1  
DATED         : June 11, 2002  
INVENTOR(S)   : Vuligonda et al.

Page 4 of 9

It is certified that error appears in the above-identified patent and that said Letters Patent is hereby corrected as shown below:

Column 42,  
Lines 25-27,  "
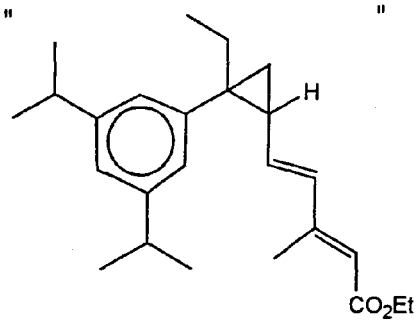
"    should be

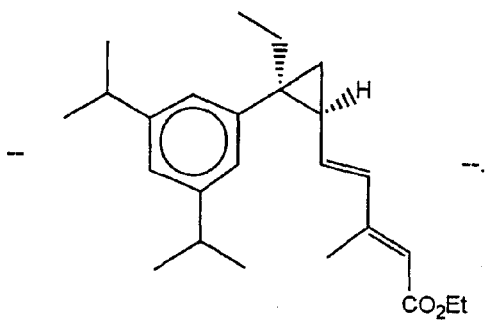

Line 42, "C." should be -- C --.

Column 43,  
Lines 5-7,  "
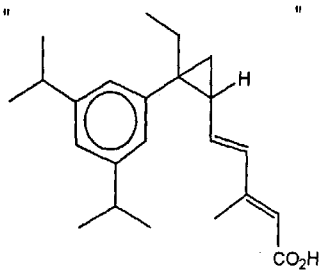
"    should be
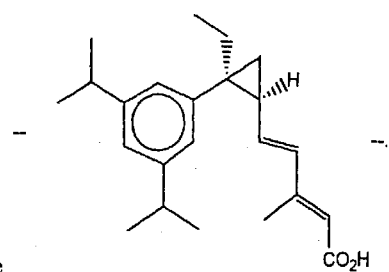

Lines 20, 38 and 43, "C." should be -- C --.  
Line 30, "$^{C.}$" should be -- $^C$ --.  
Line 42, the first occurrence of "C." should be -- C --.

Column 44,  
Lines 4 and 25, "$^{C.}$" should be -- $^C$ --.

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

<u>Column 44 cont'd,</u>
Lines 40-41,

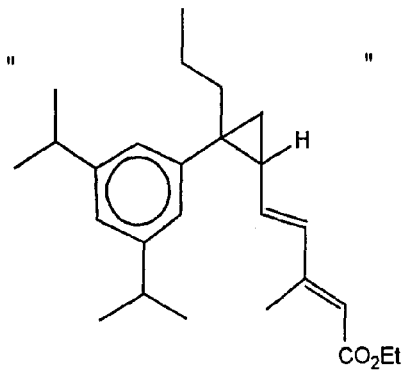  should be  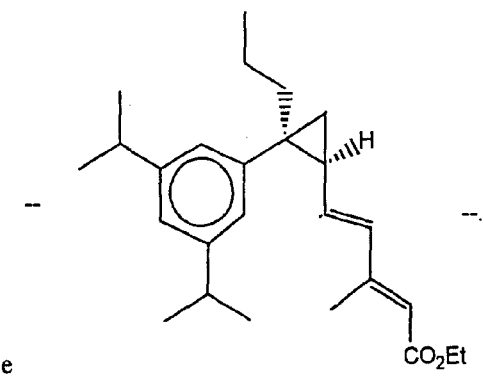

Line 59, "D" should be -- D --.
Line 59, "$^{C.}$" should be -- $^{C}$ --.

<u>Column 45,</u>
Lines 8-10,

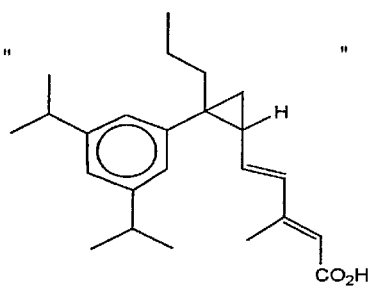  should be

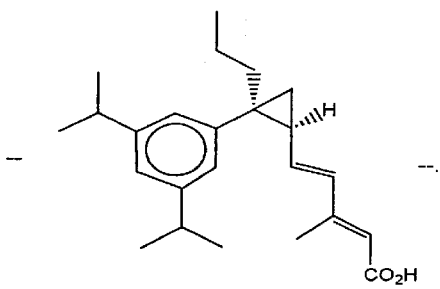

Line 25, "$^{C.}$" should be -- $^{C}$ --.

<u>Column 46,</u>
Line 7, "$^{C.}$" should be -- $^{C}$ --.

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

Column 46 cont'd,
Lines 40-41,

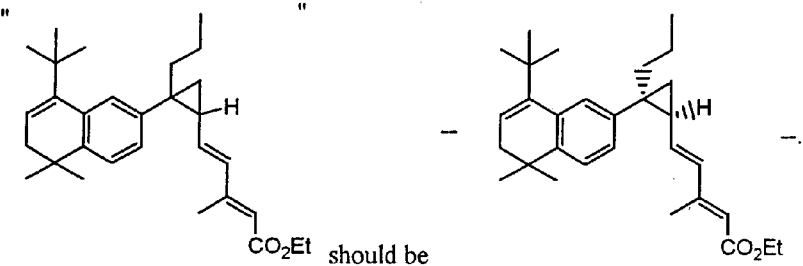

Column 47,
Lines 8-10,

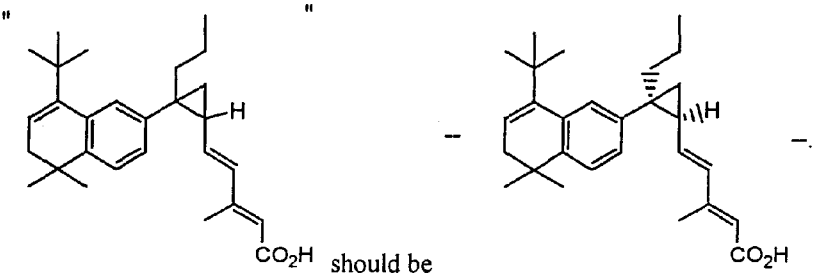

Line 25, "$^{C.}$" should be -- $^{C}$ --.
Lines 41 and 46, "C. " should be -- C --.

Column 48,
Line 30,

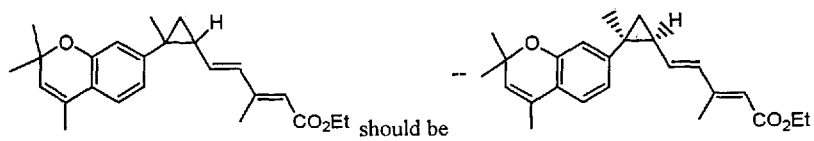

Lines 54-55,

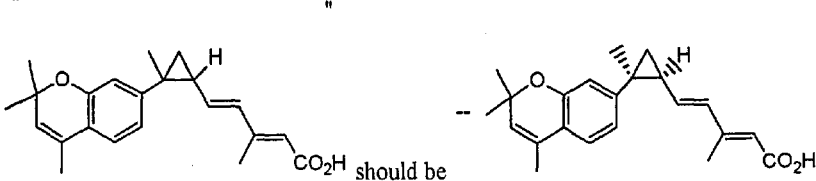

UNITED STATES PATENT AND TRADEMARK OFFICE
CERTIFICATE OF CORRECTION

PATENT NO. : 6,403,638 B1  Page 7 of 9
DATED : June 11, 2002
INVENTOR(S) : Vuligonda et al.

It is certified that error appears in the above-identified patent and that said Letters Patent is hereby corrected as shown below:

Column 49,
Lines 44 and 61, "$^{C.}$" should be -- $^C$ --.

Column 50,
Lines 8-10,

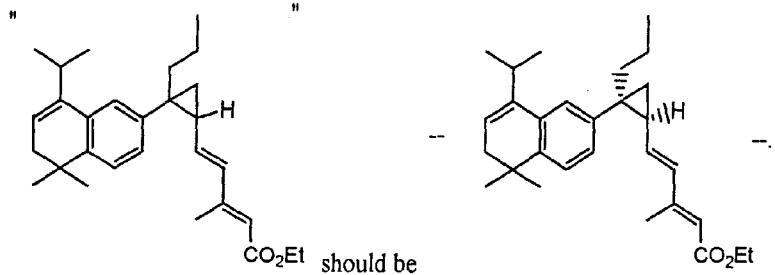

Line 25, "$^{C.}$" should be -- $^C$ --.
Lines 44-45,

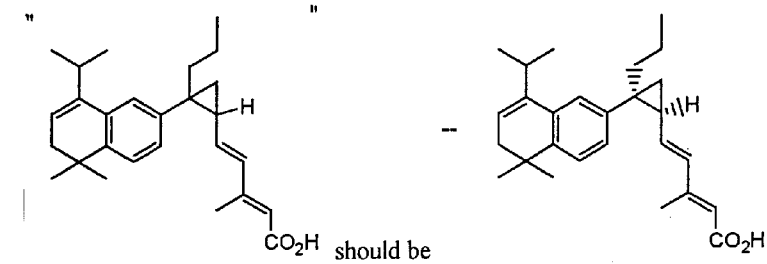

Line 61, "$^{C.}$" should be -- $^C$ --.

Column 51,
Line 24, "C." should be -- C --.

Column 52,
Line 3, "J 5.5" should be -- J = 5.5 --.
Line 10, insert -- : -- before "tetrahydrofuran".

Column 53,
Line 12, "J 4.8" should be -- J = 4.8 --.

Column 54,
Lines 3, 9, 34 and 52, "C." should be -- C --.

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

Column 55,
Lines 5, 7 and 36, "C." should be -- C --.
Lines 14 and 16, both occurrences of "C." should be -- C --.
Line 56, "750" should be -- 75° --.

Column 56,
Lines 17, 44 and 63, "C." should be -- C --.
Line 32, after "1.96 (s, 3H)," insert -- 2.13 (d, --.

Column 57,
Lines 14, 36 and 37, "C." should be -- C --.
Line 35, delete "." after "added".
Lines 44-46, all four occurrences of "C." should be -- C --.

Column 58,
Lines 3 and 53, "C." should be -- C --.

Column 59,
Line 5, "Isoproply" should be -- Isopropyl --.
Line 12, "C." should be -- C --.
Lines 32-33, both occurrences of "C." should be -- C --.

Column 60,
Line 41, "C." should be -- C --.
Line 46, "5% 15%" should be -- 5% ~ 15% --.

Column 61,
Lines 14 and 21, "C." should be -- C --.

Column 64,
Line 35, "C." should be -- C --.

Column 65,
Lines 14 and 28, "C." should be -- C --.
Lines 17 and 46-47, both occurrences of "C." should be -- C --.
Lines 54-57, all four occurrences of "C." should be -- C --.

UNITED STATES PATENT AND TRADEMARK OFFICE
CERTIFICATE OF CORRECTION

PATENT NO. : 6,403,638 B1
DATED : June 11, 2002
INVENTOR(S) : Vuligonda et al.

It is certified that error appears in the above-identified patent and that said Letters Patent is hereby corrected as shown below:

Column 66,
Lines 10 and 56, "C." should be -- C --.

Column 67,
Line 13, "C." should be -- C --.

Signed and Sealed this

Eighth Day of April, 2003

JAMES E. ROGAN
*Director of the United States Patent and Trademark Office*